(12) United States Patent
Kalish et al.

(10) Patent No.: US 9,932,303 B2
(45) Date of Patent: Apr. 3, 2018

(54) N-HYDROXYMETHANESULFONAMIDE NITROXYL DONORS

(71) Applicant: Cardioxyl Pharmaceuticals, Inc., Chapel Hill, NC (US)

(72) Inventors: Vincent Jacob Kalish, Annapolis, MD (US); Frederick Arthur Brookfield, Abingdon (GB); Stephen Martin Courtney, Abingdon (GB); Lisa Marie Frost, Abingdon (GB)

(73) Assignee: Cardioxyl Pharmaceuticals, Inc., Chapel Hill, NC (US)

( * ) Notice: Subject to any disclaimer, the term of this patent is extended or adjusted under 35 U.S.C. 154(b) by 90 days.

(21) Appl. No.: 14/926,512

(22) Filed: Oct. 29, 2015

(65) Prior Publication Data

US 2016/0046569 A1 Feb. 18, 2016

Related U.S. Application Data

(63) Continuation of application No. PCT/US2015/011792, filed on Jan. 16, 2015.

(60) Provisional application No. 61/928,956, filed on Jan. 17, 2014.

(51) Int. Cl.
| | |
|---|---|
| *C07C 311/48* | (2006.01) |
| *A61K 31/18* | (2006.01) |
| *A61K 31/185* | (2006.01) |
| *C07D 261/20* | (2006.01) |
| *C07D 307/79* | (2006.01) |
| *C07D 333/18* | (2006.01) |
| *C07D 239/26* | (2006.01) |
| *C07D 213/34* | (2006.01) |
| *C07D 305/08* | (2006.01) |
| *C07D 307/38* | (2006.01) |
| *C07D 307/81* | (2006.01) |
| *A61K 9/00* | (2006.01) |
| *A61K 31/277* | (2006.01) |
| *A61K 31/337* | (2006.01) |
| *A61K 31/343* | (2006.01) |
| *A61K 31/381* | (2006.01) |
| *A61K 31/423* | (2006.01) |
| *A61K 31/4402* | (2006.01) |
| *A61K 31/4406* | (2006.01) |
| *A61K 31/4409* | (2006.01) |
| *A61K 31/505* | (2006.01) |
| *A61K 31/724* | (2006.01) |

(52) U.S. Cl.
CPC .......... *C07C 311/48* (2013.01); *A61K 9/0019* (2013.01); *A61K 9/0053* (2013.01); *A61K 31/185* (2013.01); *A61K 31/277* (2013.01); *A61K 31/337* (2013.01); *A61K 31/343* (2013.01); *A61K 31/381* (2013.01); *A61K 31/423* (2013.01); *A61K 31/4402* (2013.01); *A61K 31/4406* (2013.01); *A61K 31/4409* (2013.01); *A61K 31/505* (2013.01); *A61K 31/724* (2013.01); *C07D 213/34* (2013.01); *C07D 239/26* (2013.01); *C07D 261/20* (2013.01); *C07D 305/08* (2013.01); *C07D 307/38* (2013.01); *C07D 307/79* (2013.01); *C07D 307/81* (2013.01); *C07D 333/18* (2013.01); *C07C 2601/02* (2017.05)

(58) Field of Classification Search
CPC combination set(s) only.
See application file for complete search history.

(56) References Cited

U.S. PATENT DOCUMENTS

| | | | |
|---|---|---|---|
| 3,751,255 | A | 8/1973 | Wilson et al. |
| 4,369,174 | A | 1/1983 | Nagai et al. |
| 4,539,321 | A | 9/1985 | Campbell |
| 4,663,351 | A | 5/1987 | Diamond |
| 4,798,824 | A | 1/1989 | Belzer et al. |
| 4,842,866 | A | 6/1989 | Horder et al. |
| 5,217,720 | A | 6/1993 | Sekigawa et al. |
| 6,525,081 | B1 | 2/2003 | Matsumoto et al. |
| 6,569,457 | B2 | 5/2003 | Ullah et al. |
| 6,638,534 | B1 | 10/2003 | Ishibashi et al. |
| 6,936,639 | B2 | 8/2005 | Wink et al. |
| 7,648,997 | B2 | 1/2010 | Kshirsagar et al. |
| 7,696,373 | B2 | 4/2010 | King |
| 7,863,262 | B2 | 1/2011 | Wink et al. |
| 7,989,652 | B2 | 8/2011 | King |
| 8,030,356 | B2 | 10/2011 | Toscano et al. |
| 8,227,639 | B2 | 7/2012 | Toscano et al. |
| 8,268,890 | B2 | 9/2012 | Wink et al. |

(Continued)

FOREIGN PATENT DOCUMENTS

| | | |
|---|---|---|
| EP | 2190814 | 6/2010 |
| IL | 204434 | 10/2010 |

(Continued)

OTHER PUBLICATIONS

Stella et al. "Cyclodextrins" Toxicol. Pathol. 2008, 36, 30-42.*
Chemical Abstract Service STN Registry Database No. 1225524-77-5 [entered STN: May 28, 2010].*
Chemical Abstract Service STN Registry Database No. 1225529-38-3 [entered STN: May 28, 2010].*
Tsuchiya et al. "Syntheses and Thermal Rearrangements of N-Imino-1,2,5,6-tetrahydropyridinium and N-Imino-Δ3-pyrolidinium Ylides" Chem. Pharm. Bull. 1978, 26, 2880-2885.*
Mohammed et al. "The Preparation of Sulfonamides by Reduction of N-Hydroxysulfonamides" Synthesis 1972, 10, 574-575.*

(Continued)

*Primary Examiner* — Amanda L Aguirre
(74) *Attorney, Agent, or Firm* — Byrne Poh LLP; Nina R. Horan

(57) ABSTRACT

The disclosed subject matter provides N-hydroxymethanesulfonamide compounds, pharmaceutical compositions and kits comprising such compounds, and methods of using such compounds or pharmaceutical compositions. In particular, the disclosed subject matter provides methods of using such compounds or pharmaceutical compositions for treating heart failure.

77 Claims, No Drawings

(56) References Cited

U.S. PATENT DOCUMENTS

| | | |
|---|---|---|
| 8,269,034 B2 | 9/2012 | King |
| 8,318,705 B2 | 11/2012 | Frost et al. |
| 8,598,192 B2 | 12/2013 | Kshirsagar et al. |
| 8,674,132 B2 | 3/2014 | Toscano et al. |
| 8,791,134 B2 | 7/2014 | Frost et al. |
| RE45,314 E | 12/2014 | Toscano et al. |
| 8,987,326 B2 | 3/2015 | Kalish et al. |
| 9,018,411 B2 | 4/2015 | Toscano et al. |
| 9,115,064 B2 | 8/2015 | Toscano et al. |
| 9,156,804 B2 | 10/2015 | Kalish et al. |
| 9,181,213 B2 | 11/2015 | Toscano et al. |
| 9,221,780 B2 | 12/2015 | Toscano et al. |
| 9,458,127 B2 | 10/2016 | Toscano et al. |
| 9,464,061 B2 | 10/2016 | Toscano et al. |
| 2004/0038947 A1 | 2/2004 | Wink et al. |
| 2005/0153966 A1 | 7/2005 | Gangloff et al. |
| 2005/0192254 A1 | 9/2005 | Wink et al. |
| 2007/0299107 A1 | 12/2007 | Toscano et al. |
| 2009/0163487 A1 | 6/2009 | Toscano et al. |
| 2009/0186045 A1 | 7/2009 | Ray et al. |
| 2009/0281067 A1 | 11/2009 | Toscano et al. |
| 2009/0298795 A1 | 12/2009 | Paolocci et al. |
| 2011/0081427 A1 | 4/2011 | Wink et al. |
| 2011/0144067 A1 | 6/2011 | Toscano et al. |
| 2011/0160200 A1 | 6/2011 | Mazhari et al. |
| 2011/0306614 A1 | 12/2011 | Toscano et al. |
| 2012/0004259 A1 | 8/2012 | Wink et al. |
| 2012/0201907 A1 | 8/2012 | Wink et al. |
| 2014/0194416 A1 | 7/2014 | Toscano et al. |
| 2014/0235636 A1 | 8/2014 | Toscano et al. |
| 2014/0336137 A1 | 11/2014 | Frost et al. |
| 2015/0004259 A1 | 1/2015 | Wink et al. |
| 2015/0141378 A1 | 5/2015 | Toscano et al. |
| 2015/0197502 A1 | 7/2015 | Toscano et al. |
| 2015/0291519 A1 | 10/2015 | Toscano et al. |
| 2015/0336880 A1 | 11/2015 | Toscano et al. |
| 2015/0344437 A1 | 12/2015 | Kalish et al. |
| 2015/0366977 A1 | 12/2015 | Kalish et al. |
| 2016/0002156 A1 | 1/2016 | Toscano et al. |
| 2016/0031807 A1 | 2/2016 | Kalish et al. |
| 2016/0046570 A1 | 2/2016 | Toscano et al. |
| 2016/0052862 A1 | 2/2016 | Frost et al. |
| 2016/0081951 A1 | 3/2016 | Mazhari et al. |
| 2016/0115148 A1 | 4/2016 | Toscano et al. |
| 2016/0166604 A1 | 6/2016 | Paolocci et al. |
| 2016/0228460 A1 | 8/2016 | Wink et al. |

FOREIGN PATENT DOCUMENTS

| | | |
|---|---|---|
| IL | 193839 | 4/2015 |
| JP | H01-221371 | 9/1989 |
| JP | H01-221372 | 9/1989 |
| JP | H04-046169 | 6/1990 |
| JP | H04-321671 | 11/1992 |
| JP | H06-168275 | 11/1992 |
| JP | 2010-142729 | 5/1998 |
| JP | H10-142729 | 5/1998 |
| JP | 2002-072459 | 3/2002 |
| JP | 2004-536820 | 12/2004 |
| SU | 186456 | 1/1966 |
| WO | WO/2001-010827 | 2/2001 |
| WO | WO/2002-100810 | 12/2002 |
| WO | WO/2005-018556 | 3/2005 |
| WO | WO/2005-048945 | 6/2005 |
| WO | WO/2005-074598 | 8/2005 |
| WO | WO/2006-086188 | 8/2006 |
| WO | WO/2007-002444 | 1/2007 |
| WO | WO/2007-109175 | 9/2007 |
| WO | WO/2007-120839 | 10/2007 |
| WO | WO/2009-042970 | 4/2009 |
| WO | WO/2013-059194 | 4/2013 |
| WO | WO/2014-070919 | 5/2014 |
| WO | WO/2014-113700 | 7/2014 |
| WO | WO/2015-109210 | 7/2015 |

OTHER PUBLICATIONS

Andrewes, C.H. et al., "Experimental Chemotherapy of Typhus: Anti-Rickettsial Action of p-Sulphonamidobenzamidine and Related Compounds", In Proceedings of the Royal Society of London B Biological Sciences, vol. 133, No. 1, Jan. 1946, pp. 20-62.

Angell, A. et al., "Research on Some Hydroxamic Acids", In Gazzetta Chimica Italiana, vol. 33, No. 2, 1902, pp. 296-311.

Backx, P.H. et al., "The Relationship between Contractile Force and Intracellular [Ca2+] in Intact Rat Cardiac Trabeculae", In the Journal of General Physiology, vol. 105, No. 1, Jan. 1995, pp. 1-19.

Baerlocher, F.J. et al., "New and More Potent Antifungal Disulfides", In the Australian Journal of Chemistry, vol. 53, No. 1, May 2000, pp. 1-5.

Baumgarth, M. et al., "(2-Methyl-5-(methylsulfonyl)benzoyl)guanidine Na'/H+ Antiporter Inhibitors", In the Journal of Medicinal Chemistry, vol. 40, No. 13, Jun. 1997, pp. 2017-2034.

Bonner, F.T. and Ko, Y., "Kinetic, Isotopic, and Nitrogen-15 NMR Study of N-hydroxybenzenesulfonamide Decomposition: an Nitrosyl Hydride (HNO) Source Reaction", In Inorganic Chemistry, vol. 31, No. 12, Jun. 1, 1992, pp. 2514-2519.

Bouzamondo, A. et al., "Beta-Blocker Treatment in Heart Failure", In Fundamental & Clinical Pharmacology, vol. 15, No. 2, Apr. 2001, pp. 95-109.

Bristow, M.R. et al., "Inotropes and Beta-Blockers: Is there a Need for New Guidelines?", In the Journal of Cardiac Failure, vol. 7, No. 2, Suppl. 1, Jun. 2001, pp. 8-12.

Bristow, M.R., "β-Adrenergic Receptor Blockade in Chronic Heart Failure", In Circulation, vol. 101, No. 5, Feb. 2000, pp. 558-569.

Brynes, S. et al., "Potential Antitumor Agents via Inhibitors of L-Asparagine Synthetase: Substituted Sulfonamides and Sulfonyl Hydrazides Related to Glutamine", In the Journal of Pharmaceutical Sciences, vol. 67, No. 11, Nov. 1977, pp. 1550-1553.

Brynes, S. et al., "Potential Inhibitors of L-Asparagine Biosynthesis. 4. Substituted Sulfonamide and Sulfonylhydrazide Analogues of L-Asparagine", In the Journal of Medicinal Chemistry, vol. 21, No. 1, Jan. 1978, pp. 45-49.

Crawford, J.H. et al., "Hypoxia, Red Blood Cells, and Nitrite Regulate NO-dependent Hypoxic Vasodilation", In Blood, vol. 107, No. 2, Jan. 2006, pp. 566-575.

Database CAPlus Abstract Accession No. 1994:645157, Chemical Abstracts Service, Columbus, OH, 1994, pp. 1.

Database CAPLUS, Chemical Abstracts Service, Columbus, OH, US, accession No. 2002:176265 (XP002509265), Mar. 2002, pp. 1.

Database CHEMCATS, Chemical Abstracts Service, Kiev, UK, accession No. 2033522701 (XP002509263), Jan. 2008, pp. 1.

Database CHEMCATS, Chemical Abstracts Service, Kiev, UK, accession No. 2033715491 (XP002509261), Jan. 2008, pp. 1.

Database CHEMCATS, Chemical Abstracts Service, San Diego, CA, US, accession No. 2037996565 (XP002509259), Jun. 2008, pp. 1.

Database REGISTRY, "RN 393519-92-1: 5-Quinolinesulfonamide, N-hydroxy-" Chemical Library, LaboTest, entered STN: Feb. 19, 2002, pp. 1.

Database REGISTRY, Chemical Abstracts Service, Columbus, OH, US, accession No. 790725-76-7 (XP002509264), Nov. 2004, pp. 1.

Database REGISTRY, Chemical Abstracts Service, Columbus, OH, US, accession No. 920663-30-5 (XP002509260), Feb. 2007, pp. 1.

Database REGISTRY, Chemical Abstracts Service, Columbus, OH, US, accession No. 930060-34-7 (XP002509262), Apr. 2007, pp. 1.

Extended Search Report dated Apr. 5, 2013 in European Patent Application No. 12195114.9.

Extended Search Report dated Apr. 5, 2013 in European Patent Application No. 12195118.0.

Extended Search Report dated Apr. 5, 2013 in European Patent Application No. 12195124.8.

Extended Search Report dated Apr. 5, 2013 in European Patent Application No. 12195128.9.

Extended Search Report dated Jul. 23, 2012 in European Patent Application No. 12155608.8.

(56) References Cited

OTHER PUBLICATIONS

Fukuto, J.M. et al., "The Physiological Chemistry and Biological Activity of Nitroxyl (HNO): The Neglected, Misunderstood, and Enigmatic Nitrogen Oxide", In Chemical Research in Toxicology, vol. 18, No. 5, May 2005, pp. 790-801.

Gao, W.D. et al., "Calcium Cycling and Contractile Activation in Intact Mouse Cardiac Muscle", In Journal of Physiology, vol. 507, No. 1, Feb. 1998, pp. 175-184.

Gao, W.D. et al., "Myofilament Ca2+ Sensitivity in Intact Versus Skinned Rat Ventricular Muscle", In Circulation Research, vol. 74, No. 3, Mar. 1994, pp. 408-415.

Gao, W.D. et al., "Relationship Between Intracellular Calcium and Contractile Force in Stunned Myocardium: Direct Evidence for Decreased Myofilament CA2+ Responsiveness and Altered Diastolic Function in Intact Ventricular Muscle", In Circulation Research, vol. 76, No. 6, Jun. 1995, pp. 1036-1048.

Hare, J.M. et al., "Nitric Oxide Inhibits the Positive Inotropic Response to Beta-Adrenergic Stimulation in Humans with Left Ventricular Dysfunction", In Circulation, vol. 92, No. 8, Oct. 1995, pp. 2198-2203.

Hare, J.M. et al., "Pertussis Toxin-Sensitive G Proteins Influence Nitric Oxide Synthase III Activity and Protein Levels in Rat Heart", In the Journal of Clinical Investigations, vol. 101, No. 6, Mar. 1998, pp. 1424-1431.

Hart, C.Y.T. et al., "Differential Effects of Natriuretic Peptides and NO On LV Function in Heart Failure and Normal Dogs", In the American Journal of Physiology—Heart and Circulatory Physiology, vol. 281, No. 1, Jul. 2001, pp. 146-154.

Ingall, T.J., "Preventing Ischemic Stroke", In Postgraduate Medicine, vol. 107, No. 6, May 2000, pp. 34-50.

International Preliminary Report on Patentability dated Jul. 28, 2016 in International Patent Application No. PCT/US2015/011792.

International Preliminary Report on Patentability dated Sep. 23, 2008 in International Patent Application No. PCT/US2007/006710.

International Search Report and Written Opinion dated Jan. 23, 2009 in International Patent Application No. PCT/US2008/078024.

International Search Report and Written Opinion dated Mar. 31, 2015 in International Patent Application No. PCT/US2015/011792.

International Search Report and Written Opinion dated Aug. 22, 2007 in International Patent Application No. PCT/US2007/006710.

Jackman, G.B. et al., "Studies in the Field of Diuretic Agents: Part VIII. Some Miscellaneous Derivatives", In the Journal of Pharmacy Pharmacology. vol. 15, Sep. 1963, pp. 202-211.

Johnson, S. et al., "Targeting Metallo-Proteins by Fragment-Based Lead Discovery", In Chemical Biology & Drug Design, vol. 78, No. 2, Aug. 2011, pp. 211-223.

Katori, T. et al., "Calcitonin Gene-Related Peptide in Vivo Positive Inotropy is Attributable to Regional Sympatho-Stimulation and is Blunted in Congestive Heart Failure", In Circulation Research, vol. 96, No. 2, Feb. 2005, pp. 234-243.

Lee, M.J.C. et al., "N-Hydroxybenzenecarboximidic Acid Derivatives: A New Class of Nitroxyl-Generating Prodrugs", In Nitric Oxide: Biology and Chemistry, vol. 5, No. 3, Jun. 2001, pp. 278-287.

Lowes, B.D. et al., "Inotropes in the Beta-Blocker Era", In Clinical Cardiology, vol. 23, No. S3, Mar. 2000, pp. III11-III16.

Ma, X.L. et al., "Opposite Effects of Nitric Oxide and Nitroxyl on Postischemic Myocardial Injury", In Proceedings of the National Academy of Sciences of the United States of America, vol. 96, No. 25, Dec. 1999, pp. 14617-14622.

Mincione, F. et al., "Carbonic Anhydrase Inhibitors: Inhibition of Isozymes I, II and IV with N-Hydroxysulfonamides—a Novel Class of Intraocular Pressure Lowering Agents", In the Journal of Enzyme Inhibition and Medicinal Chemistry, vol. 13, No. 4, Jan. 1998, pp. 267-284.

Miranda, K.M. et al., "Mechanism of Aerobic Decomposition of Angeli's Salt (Sodium Trioxodinitrate) at Physiological pH", In the Journal of the American Chemical Society, vol. 127, No. 2, Jan. 2005, pp. 722-731.

Nagasawa, H.T. et al., "Prodrugs of Nitroxyl as Potential Aldehyde Dehydrogenase Inhibitors vis-a-vis Vascular Smooth Muscle Relaxants", In Journal of Medicinal Chemistry, vol. 38, No. 11, May 1995, pp. 1865-1871.

Notice of Allowance dated Apr. 17, 2015 in U.S. Appl. No. 14/204,636.

Office Action dated Jan. 19, 2016 in Japanese Patent Application No. 2014-249100.

Office Action dated Jan. 26, 2016 in Korean Patent Application No. 10-2010-7007536.

Office Action dated Jan. 29, 2016 in Chinese Patent Application No. 201410778806.3.

Office Action dated Feb. 11, 2011 in Russian Patent Application No. 2008141151.

Office Action dated Feb. 26, 2015 in Korean Patent Application No. 10-2014-7034138.

Office Action dated Mar. 11, 2015 in Korean Patent Application No. 10-2010-7007536.

Office Action dated Mar. 13, 2015 in Korean Patent Application No. 10-2014-700661.

Office Action dated Apr. 9, 2013 in European Patent Application No. 12155608.8.

Office Action dated Apr. 10, 2013 in Canadian Patent Application No. 2,645,988.

Office Action dated Apr. 14, 2010 in New Zealand Patent Application No. 570971.

Office Action dated Apr. 14, 2015 in Chinese Patent Application No. 201310086960.X.

Office Action dated May 11, 2011 in Israeli Patent Application No. 193839.

Office Action dated May 12, 2010 in Chinese Patent Application No. 200780011079.6.

Office Action dated May 18, 2012 in Chinese Patent Application No. 200780011079.6.

Office Action dated May 19, 2016 in U.S. Appl. No. 14/262,223.

Office Action dated Jun. 4, 2013 in Japanese Patent Application No. 2009-500519.

Office Action dated Jun. 5, 2014 in Korean Patent Application No. 10-2014-7006611.

Office Action dated Jun. 6, 2016 in Canadian Patent Application No. 2,699,567.

Office Action dated Jun. 10, 2014 in Japanese Patent Application No. 2013-032658.

Office Action dated Jun. 14, 2011 in Australian Patent Application No. 2007227457.

Office Action dated Jun. 15, 2016 in Korean Patent Application No. 10-2010-7007536.

Office Action dated Jun. 16, 2016 in Israeli Patent Application No. 217739.

Office Action dated Jun. 20, 2016 in Korean Patent Application No. 10-2016-7010476.

Office Action dated Oct. 26, 2014 in Israeli Patent Application No. 204434.

Office Action dated Jul. 13, 2011 in Chinese Patent Application No. 200780011079.6.

Office Action dated Aug. 8, 2013 in European Patent Application No. 12155608.8.

Office Action dated Aug. 13, 2013 in Japanese Patent Application No. 2010-27222.

Office Action dated Aug. 21, 2012 in Japanese Patent Application No. 2009-500519.

Office Action dated Aug. 25, 2011 in New Zealand Patent Application No. 570971.

Office Action dated Sep. 1, 2015 in Canadian Patent Application No. 2,699,567.

Office Action dated Sep. 8, 2016 in Israeli Patent Application No. 238271.

Office Action dated Sep. 12, 2013 in Korean Patent Application No. 10-2008-7025245.

Office Action dated Sep. 22, 2011 in U.S. Appl. No. 12/239,705.

Office Action dated Sep. 24, 2012 in Israeli Patent Application No. 217739.

(56) References Cited

OTHER PUBLICATIONS

Office Action dated Sep. 26, 2014 in European Patent Application No. 12195124.8.
Office Action dated Sep. 30, 2016 in Korean Patent Application No. 10-2015-7020302.
Office Action dated Oct. 20, 2014 in Canadian Patent Application No. 2,699,567.
Office Action dated Oct. 21, 2011 in New Zealand Patent Application No. 595770.
Office Action dated Oct. 29, 2014 in New Zealand Patent Application No. 700984.
Office Action dated Nov. 20, 2015 in U.S. Appl. No. 14/262,223.
Office Action dated Nov. 22, 2010 in European Patent Application No. 07753345.3.
Office Action dated Nov. 23, 2010 in New Zealand Patent Applicaiton No. 584036.
Paolocci, N. et al., "CGMP-Independent Inotropic Effects of Nitric Oxide and Peroxynitrite Donors: Potential Role for Nitrosylation", In the American Journal of Physiology Heart and Circulatory Physiology, vol. 279, No. 4, Oct. 2000, pp. 111982-111988.
Paolocci, N. et al., "Positive Inotropic and Lusitropic Effects of HNO/NO– in Failing Hearts: Independence from Beta-Adrenergic Signaling", In Proceedings of the National Academy of Sciences, vol. 100, No. 9, Apr. 2003, pp. 5537-5542.
Rastaldo, R. et al., "Cytochrome P-450 Metabolite of Arachidonic Acid Mediates Bradykinin-induced Negative Inotropic Effect", In American Journal of Physiology Heart and Circulatory Physiology, vol. 280, No. 6, Jun. 2001, pp. H2823-H2832.
Rautio, J. et al., "Prodrugs: Design and Clinical Applications", In Nature Reviews Drug Discover, vol. 7, Feb. 2008, pp. 255-270.
Rehse, K. et al., "New NO Donors with Antithrombotic and Vasodilating Activities, Part 25, Hydroxylamine Derivatives", In Archiv der Pharmazie, vol. 331, Nov. 1998, pp. 365-367.
Scozzafava, A. and Supuran, C.T., "Additions and Corrections", In the Journal of Medicinal Chemistry, vol. 44, Mar. 8, 2001, pp. 1016.
Scozzafava, A. and Supuran, C.T., "Carbonic Anhydrase and Matrix Metalloproteinase Inhibitors: Sulfonylated Amino Acid Hydroxamates with MMP Inhibitory Properties Act as Efficient Inhibitors of CA Isozymes I, II, and IV, and N-Hydroxysulfonamides Inhibit . . . ", In the J. Med. Chem., vol. 43, No. 20, Oct. 2000, pp. 3677-3687.
Sha, X. et al., "Hydrolysis of Acyloxy Nitroso Compounds Yields Nitroxyl (HNO)", In Journal of the American Chemical Society, vol. 128, No. 30, Jul. 2006, pp. 9687-9692.
Singapore Search Report and Written Opinion dated Jan. 4, 2010 in Singapore Patent Application No. 200806554-2.
Singapore Search Report and Written Opinion dated Aug. 26, 2011 in Singapore Patent Application No. 201001904-1.
Slotwiner-Nie, P.K. et al., "Infectious Diarrhea in the Elderly", In Gastroenterology Clinics of North America, vol. 30, No. 3, Sep. 2001, pp. 625-635.
Spinale, F.G. et al., "Matrix Metalloproteinase Inhibition During the Development of Congestive Heart Failure", In Circulation Research, vol. 85, Jun. 9, 1999, pp. 364-376.
Suzuki, T. et al., "Novel Inhibitors of the Human Histone Deacetylases: Design, Synthesis, Enzyme Inhibition and Cancer Cell Growth Inhibition of SAHA-Based Non-hydroxomates", In the Journal of Medicinal Chemistry, vol. 48, No. 4, Jan. 25, 2005, pp. 1019-1032.
Takahira, R. et al., "Dexamethasone Attenuates Neutrophil Infiltration in the Rat Kidney in Ischemia/Reperfusion Injury: The Possible Role of Nitroxyl", In Free Radical Biology & Medicine, vol. 31, No. 6, Sep. 15, 2001, pp. 809-815.
Thevis, M. et al., "High Speed Determination of Beta-Receptor Blocking Agents in Human Urine by Liquid Chromatography/Tandem Mass Spectrometry", In Biomedical Chromatography, vol. 15, No. 6, Oct. 2001, pp. 393-402.

U.S. Appl. No. 11/815,203, filed Jan. 31, 2005.
U.S. Appl. No. 11/922,793, filed Jun. 23, 2006.
Uno, H. et al., "Studies on 3-Substituted 1,2-Benzisoxazole Derivatives, 6. Syntheses of 3-(Sulfamoylmethyl)-1,2-Benzisoxazole Derivatives and their Anticonvulsant Activies", In the Journal of Medicinal Chemistry, vol. 22, No. 2, Feb. 1979, pp. 180-183.
USPTO Official Gazette Notice of Reissue Applications Filed, Dec. 17, 2013, pp. 1-2.
Wrobel, J. et al., "Synthesis of (bis)Sulfonic Acid, (bis)Benzamides as Follicle-Stimulating Hormone (FSH) Antagonists", In Bioorganic & Medicinal Chemistry, vol. 10, No. 3, Mar. 2002, pp. 639-656.
Zamora, R. et al., "Oxidative Release of Nitric Oxide Accounts for Guanylyl Cyclase Stimulating, Vasodilator and Anti-Platelet Activity of Piloty's Acid: A Comparison with Angeli's Salt", In the Biochemistry Journal, vol. 312, No. 2, Dec. 1995, pp. 333-339.
Zani, F. et al., "Antimicrobial and Genotoxic Properties of Quinoline Derivatives", In Bollettino Chimico Farmaceutico, vol. 133, No. 5, May 1994, pp. 328-338.
Office Action dated Jan. 13, 2015 in Japanese Patent Application No. 2014-025070.
Office Action dated Jan. 2, 2015 in U.S. Appl. No. 14/204,636.
Office Action dated Oct. 6, 2014 in Canadian Patent Application No. 2,645,988.
Office Action dated Aug. 6, 2015 in European Patent Application No. 12195124.8.
Office Action dated Jun. 4, 2015 in Mexican Patent Application No. MX/a/2013/005760.
Office Action dated Jul. 8, 2015 in Canadian Patent Application No. 2,645,988.
Office Action dated Jul. 7, 2015 in Mexican Patent Application No. MX/a/2013/001662.
Office Action dated Jul. 23, 2015 in European Patent Application No. 08834117.7.
Office Action dated Sep. 17, 2015 in Chinese Patent Application No. 201410148070.1.
Office Action dated Jul. 29, 2015 in Indian Patent Application No. 2788/DELNP/2010.
Office Action dated Nov. 18, 2015 in Korean Patent Application No. 10-2015-7020302.
Office Action dated Mar. 3, 2016 in Mexican Patent Application No. MX/a/2013/001662.
Office Action dated Sep. 17, 2014 in European Patent Application No. 12195118.0.
Office Action dated Feb. 26, 2016 in Russian Patent Application No. 2011152369.
Office Action dated Feb. 29, 2016 in Canadian Patent Application No. 2,645,988.
Office Action dated Mar. 30, 2016 in Israeli Patent Application No. 204434.
Office Action dated Jul. 21, 2016 in U.S. Appl. No. 14/815,917.
Office Action dated Jun. 8, 2016 in Chinese Patent Application No. 201410148070.1.
Office Action dated Aug. 12, 2016 in Russian Patent Application No. 2011152369.
Office Action dated Jan. 21, 2014 in Canadian Patent Application No. 2,645,988.
Office Action dated Jun. 11, 2014 in Chinese Patent Application No. 201310086960.X.
Office Action dated Sep. 5, 2014 in Korean Patent Application No. 10-2014-7006611.
Office Action dated Sep. 11, 2014 in European Patent Application No. 08834117.7.
Notice of Allowance dated Mar. 27, 2017 in U.S. Appl. No. 15/286,145.

* cited by examiner

N-HYDROXYMETHANESULFONAMIDE NITROXYL DONORS

BACKGROUND

Nitroxyl (HNO) has been shown to have positive cardiovascular effects in in vitro and in vivo models of failing hearts. However, at physiological pH, nitroxyl dimerizes to hyponitrous acid, which subsequently dehydrates to nitrous oxide; due to this metastability, nitroxyl for therapeutic use must be generated in situ from donor compounds. A variety of compounds capable of donating nitroxyl have been described and proposed for use in treating disorders known or suspected to be responsive to nitroxyl. See, e.g., U.S. Pat. Nos. 6,936,639; 7,696,373; 8,030,356; 8,268,890; 8,227,639; and 8,318,705 and U.S. pre-grant publication nos. 2009/0281067; 2009/0298795; 2011/0136827; and 2011/0144067. Although all of these compounds are capable of donating nitroxyl, they differ in various physicochemical properties, and there remains a need to identify nitroxyl donors that have physicochemical properties best suited for treating specific clinical conditions via specific routes of administration.

U.S. Pat. No. 8,030,056 describes the synthesis of derivatives of Piloty's Acid type compounds that are capable of donating nitroxyl under physiological conditions and are useful in treating heart failure and ischemia/reperfusion injury. The nitroxyl donor CXL-1020 (N-hydroxy-2-methanesulfonylbenzene-1-sulfonamide) has been evaluated in a Phase I safety study in healthy volunteers and in a Phase IIa placebo-controlled, double-blind, dose-escalation study conducted at multiple hospitals. Sabbah et al., "Nitroxyl (HNO) a novel approach for the acute treatment of heart failure", *Circ Heart Fail*., published online Oct. 9, 2013 (Online ISSN: 1941-3297, Print ISSN: 1941-3289). The studies demonstrated that in patients with systolic heart failure, CXL-1020, when administered intravenously as an aqueous solution at pH=4, reduced both left and right heart filling pressures and systemic vascular resistance, while increasing cardiac and stroke volume index. Hence, the studies demonstrated that CXL-1020 enhances myocardial function in human patients suffering from heart failure. However, at threshold doses of CXL-1020 needed to produce hemodynamic effects, the compound was found to induce side effects including unacceptable levels of inflammatory irritation at and distal to the intravenous insertion site, and the authors report that because of such side effects, this compound would not be a viable candidate for a human therapeutic.

Additionally, while nitroxyl donors for parenteral (e.g., intravenous) administration are currently being developed for clinical use, insufficient solid state stability of the donors has hampered the development of oral dosage forms.

Accordingly, there is a need to develop new nitroxyl donating compounds and compositions that are useful for the treatment of heart failure and that have a suitable safety profile. Moreover, there exists a need to develop nitroxyl donors that have enhanced solid state stability and that can be used for oral administration.

Citation of any reference in Section 1 of this application is not to be construed as an admission that such reference is prior art to the present application.

SUMMARY OF THE DISCLOSURE

The present disclosure relates to the discovery of N-hydroxymethanesulfonamide nitroxyl donating compounds that are highly efficacious in treating cardiovascular diseases (e.g., heart failure), have a suitable toxicological profile, and are sufficiently stable under solid state conditions and, thus, are amenable to oral administration.

One aspect of the disclosure provides a compound of formula (I):

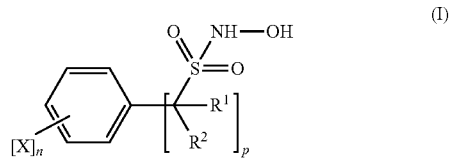

or a pharmaceutically acceptable salt thereof, wherein:
each X is independently selected from the group consisting of halo, —OH, —NO$_2$, —C≡N, (C$_1$-C$_6$)alkyl, (C$_1$-C$_6$) perhaloalkyl, (C$_1$-C$_6$)alkoxy, (C$_1$-C$_6$)perhaloalkoxy, (C$_6$-C$_{14}$)aryl, (C$_6$-C$_{14}$)aryloxy, (C$_4$-C$_7$)heterocycloalkyl, (5- or 6-membered)heteroaryl, (C$_6$-C$_{14}$)aryloxy, —SH, —SR', —S(O)R', —S(O)OH, —S(O)OR', —SO$_2$NHOH, —SO$_2$NH$_2$, —NH$_2$, —NHR', —NR'R", cycloalkoxy, —C(O)OH, —C(O)OR', —C(O)NH$_2$, C(O)NHR', —C(O)NR'R"; wherein said aryl, heterocycloalkyl and heteroaryl are unsubstituted or substituted with 1, 2, 3, 4 or 5 substituents selected from R$^4$;

each R$^4$ is independently selected from the group consisting of halo, —OH, —C≡N, —NO$_2$, —SH, =O, =S, =N—(C$_1$-C$_4$)alkyl, (C$_1$-C$_6$)alkyl, (C$_2$-C$_6$)alkenyl, (C$_2$-C$_6$) alkynyl, (C$_1$-C$_6$)alkoxy, (C$_2$-C$_6$)alkenyloxy, (C$_2$-C$_6$)alkynyloxy, (C$_6$-C$_{14}$)aryl, (C$_3$-C$_6$)cycloalkyl, (5- or 6-membered) heteroaryl, (C$_4$-C$_7$)heterocycloalkyl, —C(O)H, —C(O) NH$_2$, —C(O)OH, —NH—C(O)—NH$_2$, —NH—C(S), —NH$_2$, —SC≡N, —SO$_2$NH$_2$, —COR', —C(O)OR', —C(O) NHR', —C(O)NR'R", —NH$_2$, —NHR', —NR'R", —SR', —S(O)R', —S(O)OR', and —OR';

wherein R' and R" are independently selected from (C$_1$-C$_6$)alkyl, (C$_2$-C$_6$)alkenyl, (C$_2$-C$_6$)alkynyl, (C$_6$-C$_{14}$)aryl, (C$_3$-C$_6$)cycloalkyl, (5- or 6-membered)heteroaryl and (C$_4$-C$_7$)heterocycloalkyl;

n is 0, 1 or 2;
p is 1, 2 or 3;
R$^1$ and R$^2$ are independently selected from H, halo and (C$_1$-C$_6$)alkyl optionally substituted with one or more independently selected halo(s), or R$^1$ and R$^2$ together with the carbon to which each is attached form (C$_3$-C$_6$)cycloalkyl or (C$_4$-C$_7$)heterocycloalkyl;

provided that:
a. if n is 0 and p is 1, then R$^1$ and R$^2$ are not H;
b. if n is 1, X is COOH, and p is 1, then R$^1$ and R$^2$ are not H; and
c. if n is 2, each X is methyl, and p is 1, then R$^1$ and R$^2$ are not H.

Another aspect of the disclosure provides a compound of formula (II) or (III):

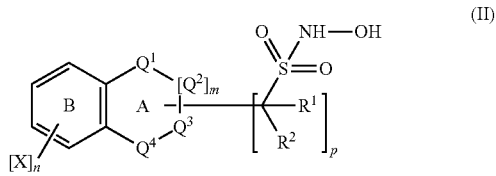

-continued

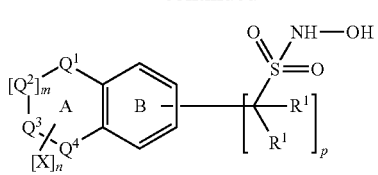

(III)

or a pharmaceutically acceptable salt thereof, wherein:

each X is independently selected from the group consisting of halo, —OH, —NO$_2$, —C≡N, (C$_1$-C$_6$)alkyl, (C$_1$-C$_6$)perhaloalkyl, (C$_1$-C$_6$)alkoxy, (C$_1$-C$_6$)perhaloalkoxy, (C$_6$-C$_{14}$)aryl, (C$_6$-C$_{14}$)aryloxy, (C$_4$-C$_7$)heterocycloalkyl, (5- or 6-membered)heteroaryl, (C$_6$-C$_{14}$)aryloxy, —SH, —SR', —S(O)R', —S(O)OH, —S(O)OR', —SO$_2$NHOH, —SO$_2$NH$_2$, —NH$_2$, —NHR', —NR'R", cycloalkoxy, —C(O)OH, —C(O)OR', —C(O)NH$_2$, C(O)NHR', —C(O)NR'R"; wherein said aryl, heterocycloalkyl and heteroaryl are unsubstituted or substituted with 1, 2, 3, 4 or 5 substituents selected from R$^4$;

each R$^4$ is independently selected from the group consisting of halo, —OH, —C≡N, —NO$_2$, —SH, =O, =S, =N—(C$_1$-C$_4$)alkyl, (C$_1$-C$_6$)alkyl, (C$_2$-C$_6$)alkenyl, (C$_2$-C$_6$)alkynyl, (C$_1$-C$_6$)alkoxy, (C$_2$-C$_6$)alkenyloxy, (C$_2$-C$_6$)alkynyloxy, (C$_6$-C$_{14}$)aryl, (C$_3$-C$_6$)cycloalkyl, (5- or 6-membered)heteroaryl, (C$_4$-C$_7$)heterocycloalkyl, —C(O)H, —C(O)NH$_2$, —C(O)OH, —NH—C(O)—NH$_2$, —NH—C(S), —NH$_2$, —SC≡N, —SO$_2$NH$_2$, —COR', —C(O)OR', —C(O)NHR', —C(O)NR'R", —NH$_2$, —NHR', —NR'R", —SR', —S(O)R', —S(O)OR', and —OR';

wherein R' and R" are independently selected from (C$_1$-C$_6$)alkyl, (C$_2$-C$_6$)alkenyl, (C$_2$-C$_6$)alkynyl, (C$_6$-C$_{14}$)aryl, (C$_3$-C$_6$)cycloalkyl, (5- or 6-membered)heteroaryl and (C$_4$-C$_7$)heterocycloalkyl;

m is 0 or 1;

n is 0, 1 or 2;

Q$^1$, Q$^2$, Q$^3$ and Q$^4$ are independently selected from —C—, —CH—, —N—, —NR$^3$—, —O— and —S—, provided that at least one of Q$^1$, Q$^2$, Q$^3$ and Q$^4$ is —N—, —NR$^3$—, —O— or —S—, and the A ring and the B ring together form a benzo-fused heteroaromatic ring containing 1 heteroatom or 2 or 3 independently selected heteroatoms;

p is 1, 2 or 3;

R$^1$ and R$^2$ are independently selected from H, halo and (C$_1$-C$_6$)alkyl optionally substituted with one or more independently selected halo(s), or R$^1$ and R$^2$ together with the carbon to which each is attached form (C$_3$-C$_6$)cycloalkyl or (C$_4$-C$_7$)heterocycloalkyl;

R$^3$ is H or (C$_1$-C$_6$)alkyl.

Another aspect of the disclosure provides a compound of formula (IV):

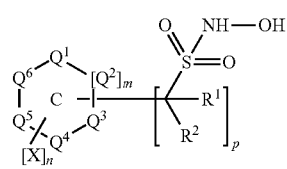

(IV)

or a pharmaceutically acceptable salt thereof, wherein:

each X is independently selected from the group consisting of halo, —OH, —NO$_2$, —C≡N, (C$_1$-C$_6$)alkyl, (C$_1$-C$_6$)perhaloalkyl, (C$_1$-C$_6$)alkoxy, (C$_1$-C$_6$)perhaloalkoxy, (C$_6$-C$_{14}$)aryl, (C$_6$-C$_{14}$)aryloxy, (C$_4$-C$_7$)heterocycloalkyl, (5- or 6-membered)heteroaryl, (C$_6$-C$_{14}$)aryloxy, —SH, —SR', —S(O)R', —S(O)OH, —S(O)OR', —SO$_2$NHOH, —SO$_2$NH$_2$, —NH$_2$, —NHR', —NR'R", cycloalkoxy, —C(O)OH, —C(O)OR', —C(O)NH$_2$, C(O)NHR', —C(O)NR'R"; wherein said aryl, heterocycloalkyl and heteroaryl are unsubstituted or substituted with 1, 2, 3, 4 or 5 substituents selected from R$^4$;

each R$^4$ is independently selected from the group consisting of halo, —OH, —C≡N, —NO$_2$, —SH, =O, =S, =N—(C$_1$-C$_4$)alkyl, (C$_1$-C$_6$)alkyl, (C$_2$-C$_6$)alkenyl, (C$_2$-C$_6$)alkynyl, (C$_1$-C$_6$)alkoxy, (C$_2$-C$_6$)alkenyloxy, (C$_2$-C$_6$)alkynyloxy, (C$_6$-C$_{14}$)aryl, (C$_3$-C$_6$)cycloalkyl, (5- or 6-membered)heteroaryl, (C$_4$-C$_7$)heterocycloalkyl, —C(O)H, —C(O)NH$_2$, —C(O)OH, —NH—C(O)—NH$_2$, —NH—C(S), —NH$_2$, —SC≡N, —SO$_2$NH$_2$, —COR', —C(O)OR', —C(O)NHR', —C(O)NR'R", —NH$_2$, —NHR', —NR'R", —SR', —S(O)R', —S(O)OR', and —OR';

wherein R' and R" are independently selected from (C$_1$-C$_6$)alkyl, (C$_2$-C$_6$)alkenyl, (C$_2$-C$_6$)alkynyl, (C$_6$-C$_{14}$)aryl, (C$_3$-C$_6$)cycloalkyl, (5- or 6-membered)heteroaryl and (C$_4$-C$_7$)heterocycloalkyl;

m is 0 or 1;

n is 0, 1 or 2;

Q$^1$, Q$^2$, Q$^3$, Q$^4$, Q$^5$ and Q$^6$ are independently selected from —C—, —CH—, —N—, —NR$^3$—, —O— and —S—, provided that at least one of Q$^1$, Q$^2$, Q$^3$, Q$^4$, Q$^5$ and Q$^6$ is —N—, —NR$^3$—, —O— or —S—, such that the C ring is a heteroaromatic ring;

p is 1, 2 or 3;

R$^1$ and R$^2$ are independently selected from H, halo and (C$_1$-C$_6$)alkyl optionally substituted with one or more independently selected halo(s), or R$^1$ and R$^2$ together with the carbon to which each is attached form (C$_3$-C$_6$)cycloalkyl or (C$_4$-C$_7$)heterocycloalkyl; and R$^3$ is H or (C$_1$-C$_6$)alkyl;

provided that if n is 0, p is 1, and ring C is furanyl, then R$^1$ and R$^2$ are not H.

DETAILED DESCRIPTION

The invention includes the following:

(1) A compound of formula (I):

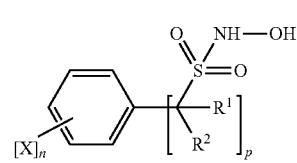

(I)

or a pharmaceutically acceptable salt thereof, wherein:

each X is independently selected from the group consisting of halo, —OH, —NO$_2$, —C≡N, (C$_1$-C$_6$)alkyl, (C$_1$-C$_6$)perhaloalkyl, (C$_1$-C$_6$)alkoxy, (C$_1$-C$_6$)perhaloalkoxy, (C$_6$-C$_{14}$)aryl, (C$_6$-C$_{14}$)aryloxy, (C$_4$-C$_7$)heterocycloalkyl, (5- or 6-membered)heteroaryl, (C$_6$-C$_{14}$)aryloxy, —SH, —SR', —S(O)R', —S(O)OH, —S(O)OR', —SO$_2$NHOH, —SO$_2$NH$_2$, —NH$_2$, —NHR', —NR'R cycloalkoxy, —C(O)OH, —C(O)OR', —C(O)NH$_2$, C(O)NHR', —C(O)NR'R"; wherein said aryl, heterocycloalkyl and heteroaryl are unsubstituted or substituted with 1, 2, 3, 4 or 5 substituents selected from R$^4$;

each R$^4$ is independently selected from the group consisting of halo, —OH, —C≡N, —NO$_2$, —SH, =O, =S, =N—($C_1$-$C_4$)alkyl, ($C_1$-$C_6$)alkyl, ($C_2$-$C_6$)alkenyl, ($C_2$-$C_6$)alkynyl, ($C_1$-$C_6$)alkoxy, ($C_2$-$C_6$)alkenyloxy, ($C_2$-$C_6$)alkynyloxy, ($C_6$-$C_{14}$)aryl, ($C_3$-$C_6$)cycloalkyl, (5- or 6-membered)heteroaryl, ($C_4$-$C_7$)heterocycloalkyl, —C(O)H, —C(O)$NH_2$, —C(O)OH, —NH—C(O)—$NH_2$, —NH—C(S), —$NH_2$, —SC≡N, —$SO_2NH_2$,—COR', —C(O)OR', —C(O)NHR', —C(O)NR'R", —$NH_2$, —NHR', —NR'R", —SR', —S(O)R', —S(O)OR', and —OR';

wherein R' and R" are independently selected from ($C_1$-$C_6$)alkyl, ($C_2$-$C_6$)alkenyl, ($C_2$-$C_6$)alkynyl, ($C_6$-$C_{14}$)aryl, ($C_3$-$C_6$)cycloalkyl, (5- or 6-membered)heteroaryl and ($C_4$-$C_7$)heterocycloalkyl;

n is 0, 1 or 2;

p is 1, 2 or 3; and $R^1$ and $R^2$ are independently selected from H, halo and ($C_1$-$C_6$)alkyl optionally substituted with one or more independently selected halo(s), or $R^1$ and $R^2$ together with the carbon to which each is attached form ($C_3$-$C_6$)cycloalkyl or ($C_4$-$C_7$)heterocycloalkyl;

provided that:

a. if n is 0 and p is 1, then $R^1$ and $R^2$ are not H;

b. if n is 1, X is COOH, and p is 1, then $R^1$ and $R^2$ are not H; and c. if n is 2, each X is methyl, and p is 1, then $R^1$ and $R^2$ are not H.

(2) The compound of the above (1), wherein each X is independently selected from the group consisting of halo, —OH, —$NO_2$, —C≡N, ($C_1$-$C_6$)perhaloalkyl, ($C_1$-$C_6$)alkoxy, ($C_1$-$C_6$)perhaloalkoxy, ($C_6$-$C_{14}$)aryl, ($C_6$-$C_{14}$)aryloxy, ($C_4$-$C_7$)heterocycloalkyl, (5- or 6-membered) heteroaryl, ($C_6$-$C_{14}$)aryloxy, —SH, —SR', —S(O)R', —S(O)OH, —S(O)OR', —$SO_2NHOH$, —$SO_2NH_2$, —$NH_2$, —NHR', —NR'R", cycloalkoxy, —C(O)OR', —C(O)$NH_2$, C(O)NHR', —C(O)NR'R"; wherein said aryl, heterocycloalkyl and heteroaryl are unsubstituted or substituted with 1, 2, 3, 4 or 5 substituents selected from $R^4$.

(3) The compound of the above (1), wherein each X is independently selected from ($C_1$-$C_6$)alkyl, halo, —$NO_2$, —C≡N, and —S(O)OR, wherein said alkyl is optionally substituted with one or more independently selected halo(s) and R is H or ($C_1$-$C_6$)alkyl.

(4) The compound of the above (1), wherein each X is independently selected from ($C_1$-$C_6$)alkyl, halo, —$NO_2$, and S(O)OR, wherein said alkyl is optionally substituted with one or more independently selected halo(s);

n is 1 or 2;

R is H or ($C_1$-$C_6$)alkyl;

p is 1;

$R^1$ and $R^2$ are independently selected from H and ($C_1$-$C_6$)alkyl optionally substituted with one or more independently selected halo(s), or $R^1$ and $R^2$ together with the carbon to which each is attached form ($C_3$-$C_6$)cycloalkyl.

(5) The compound of any one of the above (1)-(3), wherein n is 0.

(6) The compound of any of the above (1)-(4), wherein n is 1.

(7) The compound of any of the above (1)-(4), wherein n is 2.

(8) The compound of any one of the above (1)-(7), wherein at least one X is ($C_1$-$C_6$)alkyl.

(9) The compound of the above (6), wherein X is ($C_1$-$C_6$)alkyl.

(10) The compound of the above (7), wherein each X is ($C_1$-$C_6$)alkyl.

(11) The compound of any one of the above (1)-(7), wherein at least one X is ($C_1$-$C_6$)alkyl substituted with one or more independently selected halo(s).

(12) The compound of the above (11), wherein at least one X is methyl substituted with one or more independently selected halo(s).

(13) The compound of the above (6), wherein X is perhaloalkyl.

(14) The compound of the above (6), wherein X is perhalomethyl.

(15) The compound of the above (6), wherein X is perfluoromethyl.

(16) The compound of the above (7), wherein each X is independently perhaloalkyl.

(17) The compound of the above (7), wherein each X is independently perhalomethyl.

(18) The compound of the above (7), wherein each X is perfluoromethyl.

(19) The compound of any one of the above (1)-(7), wherein at least one X is halo.

(20) The compound of the above (6), wherein X is halo.

(21) The compound of the above (20), wherein X is bromo, chloro or fluoro.

(22) The compound of the above (20), wherein X is bromo.

(23) The compound of the above (20), wherein X is chloro.

(24) The compound of the above (20), wherein X is fluoro.

(25) The compound of the above (7), wherein each X is independently halo.

(26) The compound of the above (25), wherein each X is independently selected from bromo, chloro and fluoro.

(27) The compound of the above (25), wherein each X is bromo.

(28) The compound of the above (25), wherein each X is chloro.

(29) The compound of the above (25), wherein each X is fluoro.

(30) The compound of any one of the above (1)-(7), wherein at least one X is nitro.

(31) The compound of the above (6), wherein X is nitro.

(32) The compound of the above (7), wherein each X is nitro.

(33) The compound of any one of the above (1)-(7), wherein at least one X is cyano.

(34) The compound of the above (6), wherein X is cyano.

(35) The compound of the above (7), wherein each X is cyano.

(36) The compound of any one of the above (1)-(7), wherein at least one X is S(O)OR.

(37) The compound of the above (6), wherein X is S(O)OR.

(38) The compound of the above (37), wherein R is H.

(39) The compound of the above (37), wherein R is ($C_1$-$C_6$)alkyl.

(40) The compound of the above (37), wherein R is methyl.

(41) The compound of the above (7), wherein each X is independently S(O)OR.

(42) The compound of the above (41), wherein R is H.

(43) The compound of the above (41), wherein R is ($C_1$-$C_6$)alkyl.

(44) The compound of the above (41), wherein R is methyl.

(45) The compound of any one of the above (1)-(44), wherein p is 1.

(46) The compound of any one of the above (1)-(44), wherein p is 2.

(47) The compound of any one of the above (1)-(44), wherein p is 3.

(48) The compound of any one of the above (1)-(47), wherein at least one of $R^1$ and $R^2$ is H.

(49) The compound of any one of the above (1)-(47), wherein each of $R^1$ and $R^2$ is H.

(50) The compound of any one of the above (1)-(47), wherein $R^1$ is H and $R^2$ is $(C_1-C_6)$alkyl optionally substituted with one or more independently selected halo(s).

(51) The compound of any one of the above (1)-(47), wherein $R^1$ is H and $R^2$ is $(C_1-C_6)$alkyl.

(52) The compound of any one of the above (1)-(47), wherein $R^1$ is H and $R^2$ is methyl.

(53) The compound of any one of the above (1)-(47), wherein each of $R^1$ and $R^2$ is $(C_1-C_6)$alkyl optionally substituted with one or more independently selected halo(s).

(54) The compound of any one of the above (1)-(47), wherein each of $R^1$ and $R^2$ is $(C_1-C_6)$alkyl substituted with one or more independently selected halo(s).

(55) The compound of any one of the above (1)-(47), wherein each of $R^1$ and $R^2$ is methyl optionally substituted with one or more independently selected halo(s).

(56) The compound of any one of the above (1)-(47), wherein each of $R^1$ and $R^2$ is methyl substituted with halo.

(57) The compound of any one of the above (1)-(47), wherein each of $R^1$ and $R^2$ is methyl substituted with fluoro.

(58) The compound of any one of the above (1)-(47), wherein each of $R^1$ and $R^2$ is $(C_1-C_6)$alkyl.

(59) The compound of any one of the above (1)-(47), wherein each of $R^1$ and $R^2$ is methyl.

(60) The compound of any one of the above (1)-(47), wherein at least one of $R^1$ and $R^2$ is halo.

(61) The compound of any one of the above (1)-(47), wherein each of $R^1$ and $R^2$ is halo.

(62) The compound of any one of the above (1)-(47), wherein at least one of $R^1$ and $R^2$ is fluoro.

(63) The compound of any one of the above (1)-(47), wherein each of $R^1$ and $R^2$ is fluoro.

(64) The compound of any one of the above (1)-(47), wherein $R^1$ and $R^2$ together with the carbon to which each is attached form $(C_3-C_6)$cycloalkyl.

(65) The compound of any one of the above (1)-(47), wherein $R^1$ and $R^2$ together with the carbon to which each is attached form cyclopropyl.

(66) The compound of any one of the above (1)-(47), wherein $R^1$ and $R^2$ together with the carbon to which each is attached form $(C_4-C_7)$heterocycloalkyl.

(67) The compound of any one of the above (1)-(47), wherein $R^1$ and $R^2$ together with the carbon to which each is attached form oxetanyl.

(68) The compound of the above (1), which is selected from:
N-hydroxy-1-(2-nitrophenyl)methanesulfonamide,
1-(4-chlorophenyl)-N-hydroxymethanesulfonamide,
1-(3-chlorophenyl)-N-hydroxymethanesulfonamide,
1-(2-chlorophenyl)-N-hydroxymethanesulfonamide,
N-hydroxy-1-(3-methylphenyl)methanesulfonamide,
1-(4-fluorophenyl)-N-hydroxymethanesulfonamide,
N-hydroxy-1-[2-(trifluoromethyl)phenyl]methanesulfonamide,
1-(2,4-difluorophenyl)-N-hydroxymethanesulfonamide,
1-(2,5-difluorophenyl)-N-hydroxymethanesulfonamide,
1-(2,5-dichlorophenyl)-N-hydroxymethanesulfonamide,
1-(2,4-dichlorophenyl)-N-hydroxymethanesulfonamide,
1-(3,4-dichlorophenyl)-N-hydroxymethanesulfonamide,
1-(3-fluorophenyl)-N-hydroxymethanesulfonamide,
1-(2-fluorophenyl)-N-hydroxymethanesulfonamide,
1-(3-bromophenyl)-N-hydroxymethanesulfonamide,
1-(4-bromophenyl)-N-hydroxymethanesulfonamide,
N-hydroxy-1-[3-(trifluoromethyl)phenyl]methanesulfonamide,
N-hydroxy-1-[4-(trifluoromethyl)phenyl]methanesulfonamide,
1-(2-chloro-6-fluorophenyl)-N-hydroxymethanesulfonamide,
1-(3,5-difluorophenyl)-N-hydroxymethanesulfonamide,
1-(2,6-dichlorophenyl)-N-hydroxymethanesulfonamide,
1-(4-Chlorophenyl)-N-hydroxyethanesulfonamide,
2-(4-Chlorophenyl)-N-hydroxypropane-2-sulfonamide,
1-(4-Chlorophenyl)-N-hydroxycyclopropane-1-sulfonamide,
1-(4-Chlorophenyl)-1,1-difluoro-N-hydroxymethanesulfonamide,
N-Hydroxy-1-(4-(methylsulfonyl)phenyl)methanesulfonamide,
N-Hydroxy-1-(pyridin-3-yl)methanesulfonamide,
N-Hydroxy-1-(pyridin-2-yl)methanesulfonamide,
N-Hydroxy-1-(pyridin-4-yl)methanesulfonamide,
1-(3,5-dichlorophenyl)-N-hydroxymethanesulfonamide,
N-hydroxy-2-phenylethane-1-sulfonamide,
N-hydroxy-1-(4-methylphenyl)methanesulfonamide,
1-(3-cyanophenyl)-N-hydroxymethanesulfonamide,
1-(4-tert-butylphenyl)-N-hydroxymethanesulfonamide,
N-hydroxy-2-phenylpropane-2-sulfonamide,
1,1-difluoro-N-hydroxy-1-phenylmethanesulfonamide,
N-hydroxy-1-phenylcyclopropane-1-sulfonamide,
N-hydroxy-1-(2-methylpyrimidin-5-yl)methanesulfonamide,
N-hydroxy-3-phenyloxetane-3-sulfonamide,
and
pharmaceutically acceptable salts thereof.

(69) The compound of the above (4), which is selected from:
N-hydroxy-1-(2-nitrophenyl)methanesulfonamide,
1-(4-chlorophenyl)-N-hydroxymethanesulfonamide,
1-(3-chlorophenyl)-N-hydroxymethanesulfonamide,
1-(2-chlorophenyl)-N-hydroxymethanesulfonamide,
N-hydroxy-1-(3-methylphenyl)methanesulfonamide,
1-(4-fluorophenyl)-N-hydroxymethanesulfonamide,
N-hydroxy-1-[2-(trifluoromethyl)phenyl]methanesulfonamide,
1-(2,4-difluorophenyl)-N-hydroxymethanesulfonamide,
1-(2,5-difluorophenyl)-N-hydroxymethanesulfonamide,
1-(2,5-dichlorophenyl)-N-hydroxymethanesulfonamide,
1-(2,4-dichlorophenyl)-N-hydroxymethanesulfonamide,
1-(3,4-dichlorophenyl)-N-hydroxymethanesulfonamide,
1-(3-fluorophenyl)-N-hydroxymethanesulfonamide,
1-(2-fluorophenyl)-N-hydroxymethanesulfonamide,
1-(3-bromophenyl)-N-hydroxymethanesulfonamide,
1-(4-bromophenyl)-N-hydroxymethanesulfonamide,
N-hydroxy-1-[3-(trifluoromethyl)phenyl]methanesulfonamide,
N-hydroxy-1-[4-(trifluoromethyl)phenyl]methanesulfonamide,
1-(2-chloro-6-fluorophenyl)-N-hydroxymethanesulfonamide,
1-(3,5-difluorophenyl)-N-hydroxymethanesulfonamide,
1-(2,6-dichlorophenyl)-N-hydroxymethanesulfonamide,
and
pharmaceutically acceptable salts thereof

(70) A compound of formula (II) or (III):

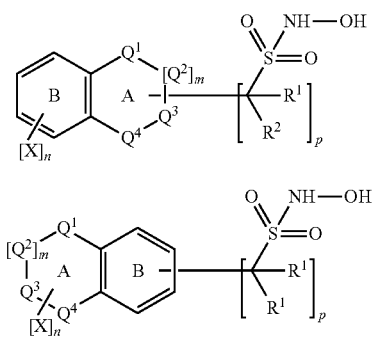

or a pharmaceutically acceptable salt thereof, wherein:

each X is independently selected from the group consisting of halo, —OH, —NO$_2$, —C≡N, (C$_1$-C$_6$)alkyl, (C$_1$-C$_6$)perhaloalkyl, (C$_1$-C$_6$)alkoxy, (C$_1$-C$_6$)perhaloalkoxy, (C$_6$-C$_{14}$)aryl, (C$_6$-C$_{14}$)aryloxy, (C$_4$-C$_7$)heterocycloalkyl, (5- or 6-membered)heteroaryl, (C$_6$-C$_{14}$)aryloxy, —SH, —SR', —S(O)R', —SO(O)H, —S(O)OR', —SO$_2$NHOH, —SO$_2$NH$_2$, —NH$_2$, —NHR', —NR'R", cycloalkoxy, —C(O)OH, —C(O)OR', —C(O)NH$_2$, C(O)NHR', —C(O)NR'R"; wherein said aryl, heterocycloalkyl and heteroaryl are unsubstituted or substituted with 1, 2, 3, 4 or 5 substituents selected from R$^4$;

each R$^4$ is independently selected from the group consisting of halo, —OH, —C≡N, —NO$_2$, —SH, =O, =S, =N—(C$_1$-C$_4$)alkyl, (C$_1$-C$_6$)alkyl, (C$_2$-C$_6$)alkenyl, (C$_2$-C$_6$)alkynyl, (C$_1$-C$_6$)alkoxy, (C$_2$-C$_6$)alkenyloxy, (C$_2$-C$_6$)alkynyloxy, (C$_6$-C$_{14}$)aryl, (C$_3$-C$_6$)cycloalkyl, (5- or 6-membered) heteroaryl, (C$_4$-C$_7$)heterocycloalkyl, —C(O)H, —C(O)NH$_2$, —C(O)OH, —NH—C(O)—NH$_2$, —NH—C(S), —NH$_2$, —SC≡N, —SO$_2$NH$_2$, —COR', —C(O)OR', —C(O)NHR', —C(O)NR'R", —NH$_2$, —NHR', —NR'R", —SR', —S(O)R', —S(O)OR', and —OR';

wherein R' and R" are independently selected from (C$_1$-C$_6$)alkyl, (C$_2$-C$_6$)alkenyl, (C$_2$-C$_6$)alkynyl, (C$_6$-C$_{14}$)aryl, (C$_3$-C$_6$)cycloalkyl, (5- or 6-membered)heteroaryl and (C$_4$-C$_7$)heterocycloalkyl;

m is 0 or 1;

n is 0, 1 or 2;

Q$^1$, Q$^2$, Q$^3$ and Q$^4$ are independently selected from —C—, —CH—, —N—, —NR$^3$—, —O— and —S—, provided that at least one of Q$^1$, Q$^2$, Q$^3$ and Q$^4$ is —N—, —NR$^3$—, —O— or —S—, and the A ring and the B ring together form a benzo-fused heteroaromatic ring containing 1 heteroatom or 2 or 3 independently selected heteroatoms;

p is 1, 2 or 3;

R$^1$ and R$^2$ are independently selected from H, halo and (C$_1$-C$_6$)alkyl optionally substituted with one or more independently selected halo(s), or R$^1$ and R$^2$ together with the carbon to which each is attached form (C$_3$-C$_6$)cycloalkyl or (C$_4$-C$_7$)heterocycloalkyl; and R$^3$ is H or (C$_1$-C$_6$)alkyl.

(71) The compound of the above (70), wherein each X is independently selected from (C$_1$-C$_6$)alkyl, halo, —NO$_2$, —C≡N, and S(O)OR, wherein said alkyl is optionally substituted with one or more independently selected halo(s) and R is H or (C$_1$-C$_6$)alkyl.

(72) The compound of the above (70), wherein each X is independently selected from (C$_1$-C$_6$)alkyl, halo, —NO$_2$, and S(O)OR, wherein said alkyl is optionally substituted with one or more independently selected halo(s);

m is 0 or 1;

n is 0, 1 or 2;

Q$^1$, Q$^2$, Q$^3$ and Q$^4$ are independently selected from —C—, —CH—, —N—, —NR$^3$—, —O— and —S—, provided that at least one of Q$^1$, Q$^2$, Q$^3$ and Q$^4$ is —N—, —NR$^3$—, —O— or —S—, and the A ring and the B ring together form a benzo-fused heteroaromatic ring containing 1 heteroatom or 2 or 3 independently selected heteroatoms;

R is H or (C$_1$-C$_6$)alkyl;

p is 1;

R$^1$ and R$^2$ are independently selected from H, and (C$_1$-C$_6$)alkyl optionally substituted with one or more independently selected halo(s), or R$^1$ and R$^2$ together with the carbon to which each is attached form (C$_3$-C$_6$)cycloalkyl; and R$^3$ is H or (C$_1$-C$_6$)alkyl.

(73) The compound of any of the above (70)-(72), wherein the compound is of formula (II).

(74) The compound of any of the above (70)-(72), wherein the compound is of formula (III).

(75) The compound of any one of the above (70)-(74), wherein m is 0.

(76) The compound of any one of the above (70)-(74), wherein m is 1.

(77) The compound of any one of the above (70)-(76), wherein n is 0.

(78) The compound of any one of the above (70)-(76), wherein n is 1.

(79) The compound of any one of the above (70)-(76), wherein n is 2.

(80) The compound of any one of the above (70)-(74), wherein m is 0 and n is 0.

(81) The compound of any one of the above (70)-(80), wherein p is 1.

(82) The compound of any one of the above (70)-(80), wherein p is 2.

(83) The compound of any one of the above (70)-(80), wherein p is 3.

(84) The compound of any one of the above (70)-(83), wherein each of R$^1$ and R$^2$ is H.

(85) The compound of any one of the above (70)-(84), wherein the A ring and the B ring together form a heteroaromatic ring containing 1 heteroatom or independently selected 2 heteroatoms.

(86) The compound of the above (85), wherein the A ring and the B ring together form a heteroaromatic ring containing 1 heteroatom.

(87) The compound of the above (85), wherein the A ring and the B ring together form a heteroaromatic ring containing 2 heteroatoms.

(88) The compound of the above (85), wherein the A ring and the B ring together form a heteroaromatic ring selected from benzopyrrole, benzofuran, benzothiophene, benzimidazole, benzopyrazole, benzoxazole, benzisoxazole, benzothiazole, benzisothiazole, quinolone and isoquinoline.

(89) The compound of the above (85), wherein the A ring and the B ring together form a heteroaromatic ring selected from benzofuran, benzoisoxazole and benzoxazole.

(90) The compound of the above (85), wherein the A ring and the B ring together form benzoxazole.

(91) The compound of the above (70), which is 1-1,2-benzoxazol-3-yl-N-hydroxymethanesulfonamide.

(92) A compound of formula (IV):

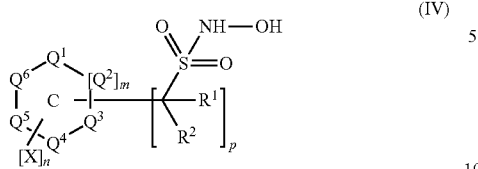

or a pharmaceutically acceptable salt thereof, wherein:

each X is independently selected from the group consisting of halo, —OH, —NO$_2$, —C≡N, (C$_1$-C$_6$)alkyl, (C$_1$-C$_6$)perhaloalkyl, (C$_1$-C$_6$)alkoxy, (C$_1$-C$_6$)perhaloalkoxy, (C$_6$-C$_{14}$)aryl, (C$_6$-C$_{14}$)aryloxy, (C$_4$-C$_7$)heterocycloalkyl, (5- or 6-membered)heteroaryl, (C$_6$-C$_{14}$)aryloxy, —SH, —SR', —S(O)R', —S(O)OH, —S(O)OR', —SO$_2$NHOH, —SO$_2$NH$_2$, —NH$_2$, —NHR', —NR'R", cycloalkoxy, —C(O)OH, —C(O)OR', —C(O)NH$_2$, C(O)NHR', —C(O)NR'R"; wherein said aryl, heterocycloalkyl and heteroaryl are unsubstituted or substituted with 1, 2, 3, 4 or 5 substituents selected from R$^4$;

each R$^4$ is independently selected from the group consisting of halo, —OH, —C≡N, —NO$_2$, —SH, =O, =S, =N—(C$_1$-C$_4$)alkyl, (C$_1$-C$_6$)alkyl, (C$_2$-C$_6$)alkenyl, (C$_2$-C$_6$)alkynyl, (C$_1$-C$_6$)alkoxy, (C$_2$-C$_6$)alkenyloxy, (C$_2$-C$_6$)alkynyloxy, (C$_6$-C$_{14}$)aryl, (C$_3$-C$_6$)cycloalkyl, (5- or 6-membered) heteroaryl, (C$_4$-C$_7$)heterocycloalkyl, —C(O)H, —C(O)NH$_2$, —C(O)OH, —NH—C(O)—NH$_2$, —NH—C(S), —NH$_2$, —SC≡N, —SO$_2$NH$_2$, —COR', —C(O)OR', —C(O)NHR', —C(O)NR'R", —NH$_2$, —NHR', —NR'R", —SR', —S(O)R', —S(O)OR', and —OR';

wherein R' and R" are independently selected from (C$_1$-C$_6$)alkyl, (C$_2$-C$_6$)alkenyl, (C$_2$-C$_6$)alkynyl, (C$_6$-C$_{14}$)aryl, (C$_3$-C$_6$)cycloalkyl, (5- or 6-membered)heteroaryl and (C$_4$-C$_7$)heterocycloalkyl;

m is 0 or 1;

n is 0, 1 or 2;

Q$^1$, Q$^2$, Q$^3$, Q$^4$, Q$^5$ and Q$^6$ are independently selected from —C—, —CH—, —N—, —NR$^3$—, —O— and —S—, provided that at least one of Q$^1$, Q$^2$, Q$^3$, Q$^4$, Q$^5$ and Q$^6$ is —N—, —NR$^3$—, —O— or —S—, such that the C ring is a heteroaromatic ring;

p is 1, 2 or 3;

R$^1$ and R$^2$ are independently selected from H, halo and (C$_1$-C$_6$)alkyl optionally substituted with one or more independently selected halo(s), or R$^1$ and R$^2$ together with the carbon to which each is attached form (C$_3$-C$_6$)cycloalkyl or (C$_4$-C$_7$)heterocycloalkyl; and R$^3$ is H or (C$_1$-C$_6$)alkyl;

provided that if n is 0, p is 1, and ring C is furanyl, then R$^1$ and R$^2$ are not H.

(93) The compound of the above (92), wherein each X is independently selected from (C$_1$-C$_6$)alkyl, halo, —NO$_2$, —C≡N, and —S(O)OR, wherein said alkyl is optionally substituted with one or more independently selected halo(s) and R is H or (C$_1$-C$_6$)alkyl.

(94) The compound of the above (92), wherein each X is independently selected from (C$_1$-C$_6$)alkyl, halo, —NO$_2$ and —S(O)OR, wherein said alkyl is optionally substituted with one or more independently selected halo(s);

m is 0 or 1;

n is 0, 1 or 2;

Q$^1$, Q$^2$, Q$^3$, Q$^4$, Q$^5$ and Q$^6$ are independently selected from —C—, —CH—, —N—, —NR$^3$—, —O— and —S—, provided that at least one of Q$^1$, Q$^2$, Q$^3$, Q$^4$, Q$^5$ and Q$^6$ is —N—, —NR$^3$—, —O— or —S—, such that the C ring is a heteroaromatic ring;

R is H or (C$_1$-C$_6$)alkyl;

p is 1; and

R$^1$ and R$^2$ are independently selected from H and (C$_1$-C$_6$)alkyl optionally substituted with one or more independently selected halo(s), or R$^1$ and R$^2$ together with the carbon to which each is attached form (C$_3$-C$_6$)cycloalkyl.

(95) The compound of any of the above (92)-(94), wherein m is 0.

(96) The compound of any of the above (92)-(94), wherein m is 1.

(97) The compound of any one of the above (92)-(96), wherein n is 0.

(98) The compound of any one of the above (92)-(96), wherein n is 1.

(99) The compound of any one of the above (92)-(96), wherein n is 2.

(100) The compound of any of the above (92)-(94), wherein m is 1 and n is 0.

(101) The compound of any one of the above (92)-(99), wherein p is 1.

(102) The compound of any one of the above (92)-(99), wherein p is 2.

(103) The compound of any one of the above (92)-(99), wherein p is 3.

(104) The compound of any one of the above (92)-(103), wherein each of R$^1$ and R$^2$ is H.

(105) The compound of any one of the above (92)-(104), wherein the C ring is a heteroaromatic ring containing 1 heteroatom or independently selected 2 heteroatoms.

(106) The compound of the above (105), wherein the C ring is a heteroaromatic ring containing 1 heteroatom.

(107) The compound of the above (105), wherein the C ring is a heteroaromatic ring containing 2 heteroatoms.

(108) The compound of the above (105), wherein the C ring is a heteroaromatic ring selected from pyrrole, furan, thiophene, imidazole, pyrazole, oxazole, isoxazole, thiazole, isothiazole, pyridine, pyrimidine, diazine, oxazine, thiazine and dithiine.

(109) The compound of the above (105), wherein the C ring is pyridine.

(110) A pharmaceutical composition comprising a compound of any one of the above (1)-(109), and at least one pharmaceutically acceptable excipient.

(111) The pharmaceutical composition of the above (110), wherein the pharmaceutical composition is suitable for intravenous administration.

(112) The pharmaceutical composition of the above (110) or (111), wherein the pharmaceutical composition has a pH of from about 5.5 to about 6.5.

(113) The pharmaceutical composition of the above (110) or (111), wherein the pharmaceutical composition has a pH of from about 6 to about 6.5.

(114) The pharmaceutical composition of the above (110) or (111), wherein the pharmaceutical composition has a pH of about 6.

(115) The pharmaceutical composition of any one of the above (110)-(114), further comprising a cyclodextrin.

(116) The pharmaceutical composition of the above (115), wherein the cyclodextrin is a sulfo-n-butyl ether derivative of β-cyclodextrin having six or seven sulfo-n-butyl ether groups per cyclodextrin molecule.

(117) The pharmaceutical composition of the above (115), wherein the cyclodextrin is CAPTISOL®.

(118) A method of treating a cardiovascular disease, comprising administering an effective amount of a compound of any one of the above (1)-(109) or the pharmaceutical composition of any one of the above (110)-(117), to a patient in need thereof.

(119) The method of the above (118), wherein the cardiovascular disease is heart failure.

(120) The method of the above (118), wherein the cardiovascular disease is acute decompensated heart failure.

(121) The method of any one of the above (118)-(120), wherein the compound or pharmaceutical composition is administered intravenously.

(122) The method of any one of the above (118)-(121), wherein the compound or pharmaceutical composition is administered at a dose of from about 20 μg nitroxyl donor/kg/minute to about 30 μg nitroxyl donor/kg/minute.

(123) The method of any one of the above (118)-(120), wherein the compound or pharmaceutical composition is administered orally.

(124) A kit comprising a compound of any one of the above (1)-(109) in dry form or a pharmaceutical composition of any one of the above (110)-(117) in dry form; and a pharmaceutically acceptable liquid diluent.

Definitions

Unless clearly indicated otherwise, the following terms as used herein have the meanings indicated below.

A "pharmaceutically acceptable salt" refers to a salt of any therapeutic agent disclosed herein, which salt can include any of a variety of organic and inorganic counter ions known in the art and which salt is pharmaceutically acceptable. When the therapeutic agent contains an acidic functionality, various exemplary embodiments of counter ions are sodium, potassium, calcium, magnesium, ammonium, tetraalkylammonium, and the like. When the therapeutic agent contains a basic functionality, a pharmaceutically acceptable salt can include as a counter ion, by way of example, an organic or inorganic acid, such as hydrochloride, hydrobromide, tartrate, mesylate, acetate, maleate, oxalate, and the like. Illustrative salts include, but are not limited to, sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucaronate, saccharate, formate, benzoate, glutamate, methanesulfonate, ethanesulfonate, benzenesulfonate, and p-toluenesulfonate salts. Accordingly, a salt can be prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl-N-ethylamine; diethylamine; triethylamine; mono-, bis-, or tris-(2-hydroxy-lower-alkyl amines), such as mono-, bis-, or tris-(2-hydroxyethyl)amine, 2-hydroxy-tert-butylamine, or tris-(hydroxymethyl)methylamine, N,N-di-lower-alkyl-N-(hydroxy-lower-alkyl)-amines, such as N,N-dimethyl-N-(2-hydroxyethyl)amine, or tri-(2-hydroxyethyl)amine; N-methyl-D-glucamine; and amino acids such as arginine, lysine, and the like. A salt can also be prepared from a compound of any one of the formulae disclosed herein having a basic functional group, such as an amino functional group, and a pharmaceutically acceptable inorganic or organic acid. Suitable acids include hydrogen sulfate, citric acid, acetic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

"Pharmaceutically acceptable excipient" refers to any substance, not itself a therapeutic agent, used as a carrier, diluent, adjuvant, binder, and/or vehicle for delivery of a therapeutic agent to a patient, or added to a pharmaceutical composition to improve its handling or storage properties or to permit or facilitate formation of a compound or pharmaceutical composition into a unit dosage form for administration. Pharmaceutically acceptable excipients are known in the pharmaceutical arts and are disclosed, for example, in Gennaro, Ed., *Remington: The Science and Practice of Pharmacy*, 20$^{th}$ Ed. (Lippincott Williams & Wilkins, Baltimore, Md., 2000) and *Handbook of Pharmaceutical Excipients*, American Pharmaceutical Association, Washington, D.C., (e.g., 1$^{st}$, 2$^{nd}$ and 3$^{rd}$ Eds., 1986, 1994 and 2000, respectively). As will be known to those in the art, pharmaceutically acceptable excipients can provide a variety of functions and can be described as wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as lactose, glucose and sucrose; (2) starches, such as corn starch and potato starch; (3) cellulose and its derivatives, such as sodium carboxymethyl cellulose, ethyl cellulose, cellulose acetate, hydroxypropylmethylcellulose, and hydroxypropylcellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

"Unit dosage form" refers to a physically discrete unit suitable as a unitary dosage for a human or an animal. Each unit dosage form can contain a predetermined amount of a therapeutic agent calculated to produce a desired effect.

Unless clearly indicated otherwise, a "patient" refers to an animal, such as a mammal, including but not limited to, a human. Hence, the methods disclosed herein can be useful in human therapy and veterinary applications. In particular embodiments, the patient is a mammal. In certain embodiments, the patient is a human.

"Effective amount" refers to such amount of a therapeutic agent or a pharmaceutically acceptable salt thereof, which in combination with its parameters of efficacy and potential for toxicity, as well as based on the knowledge of the practicing specialist, should be effective in a given therapeutic form. As is understood in the art, an effective amount can be administered in one or more doses.

"Treatment", "treating" and the like is an approach for obtaining a beneficial or desired result, including clinical results. For purposes of this disclosure, beneficial or desired results include but are not limited to inhibiting and/or suppressing the onset and/or development of a condition or reducing the severity of such condition, such as reducing the number and/or severity of symptoms associated with the condition, increasing the quality of life of those suffering from the condition, decreasing the dose of other medications required to treat the condition, enhancing the effect of another medication a patient is taking for the condition, and/or prolonging survival of patients having the condition.

"Prevent", "preventing" and the like refers to reducing the probability of developing a condition in a patient who does not have, but is at risk of developing a condition. A patient "at risk" may or may not have a detectable condition, and may or may not have displayed a detectable condition prior to the treatment methods disclosed herein. "At risk" denotes that a patient has one or more so-called risk factors, which are measurable parameters that correlate with development of a condition and are known in the art. A patient having one or more of these risk factors has a higher probability of developing the condition than a patient without such risk factor(s).

"Positive inotrope" refers to an agent that causes an increase in myocardial contractile function. Exemplary positive inotropes are a beta-adrenergic receptor agonist, an inhibitor of phosphodiesterase activity, and calcium-sensitizers. Beta-adrenergic receptor agonists include, among others, dopamine, dobutamine, terbutaline, and isoproterenol. Analogs and derivatives of such compounds are also intended. For example, U.S. Pat. No. 4,663,351 discloses a dobutamine prodrug that can be administered orally.

A condition that is "responsive to nitroxyl therapy" includes any condition in which administration of a compound that donates an effective amount of nitroxyl under physiological conditions treats and/or prevents the condition, as those terms are defined herein. A condition whose symptoms are suppressed or diminished upon administration of nitroxyl donor is a condition responsive to nitroxyl therapy.

"Pulmonary hypertension" or "PH" refers to a condition in which the pulmonary arterial pressure is elevated. The current hemodynamic definition of PH is a mean pulmonary arterial pressure (MPAP) at rest of greater than or equal to 25 mmHg. Badesch et al., *J. Amer. Coll. Cardiol.* 54(Suppl.): S55-S66 (2009).

"N/A" means not assessed.

"$(C_1-C_6)$alkyl" refers to saturated linear and branched hydrocarbon structures having 1, 2, 3, 4, 5 or 6 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_1-C_6)$alkyl groups include methyl, ethyl, n-propyl, iso-propyl, n-butyl, tert-butyl, n-hexyl, and the like.

"$(C_1-C_4)$alkyl" refers to saturated linear and branched hydrocarbon structures having 1, 2, 3, or 4 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_1-C_4)$alkyl groups include methyl, ethyl, n-propyl, iso-propyl, n-butyl, tert-butyl, and the like.

"$(C_1-C_2)$alkyl" refers to saturated linear and branched hydrocarbon structures having 1 or 2 carbon atoms. Examples of $(C_1-C_2)$alkyl groups include methyl and ethyl.

"$(C_2-C_6)$alkenyl" refers to a straight-chain or branched unsaturated hydrocarbon radical having 2, 3, 4, 5 or 6 carbon atoms and a double bond in any position, e.g., ethenyl, 1-propenyl, 2-propenyl(allyl), 1-butenyl, 2-butenyl, 3-butenyl, 1-methylethenyl, 1-methyl-1-propenyl, 2-methyl-2-propenyl, 2-methyl-1-propenyl, 1-methyl-2-propenyl, 1-hexenyl, 2-hexenyl, 3-hexenyl, 2-methyl-2-pentenyl, 4-methyl-2-pentenyl, 4-methyl-1-pentenyl, 3-methyl-1-pentenyl, and the like.

"$(C_2-C_6)$alkynyl" refers to a straight chain or branched hydrocarbon having 2, 3, 4, 5 or 6 carbon atoms and including at least one carbon-carbon triple bond. Examples of $(C_2-C_6)$alkynyls include ethynyl, propynyl, 1-butynyl, 2-butynyl, 1-pentynyl, 2-pentynyl, 1-hexynyl, 2-hexynyl, 3-hexynyl, 4-methyl-2-pentynyl and the like.

"$(C_1-C_6)$perhaloalkyl" refers to a $(C_1-C_6)$alkyl in which every hydrogen is replaced by halo, each halo being independently selected. Examples of $(C_1-C_6)$perhaloalkyl group include —$CF_3$, —$CCl_3$, —$CF_2CF_3$, —$CCl_2CF_3$, —CCLFCLF$_2$, —$CF(CF_3)_2$, —$CH(CF_3)(CH_3)$, —$CBr(CF_2)(CHCl_2)$ and the like.

"$(C_3-C_6)$cycloalkyl" refers to a saturated cyclic hydrocarbon containing 3, 4, 5, or 6 carbon atoms. Examples of $(C_3-C_6)$cycloalkyl groups include cyclopropyl, cyclobutyl, cyclopentyl and cyclohexyl.

"$(C_1-C_6)$alkoxy" refers to —O—$(C_1-C_6)$alkyl. Examples of $(C_1-C_6)$alkoxy groups include methoxy, ethoxy, propoxy, n-propoxy, iso-propoxy, butoxy, n-butoxy, sec-butoxy, tert-butoxy, pentoxy, 2-methyl-2-butoxy, hexyloxy, and the like.

"$(C_2-C_6)$alkenyloxy" refers to —O—$(C_2-C_6)$alkenyl. Examples of $(C_2-C_6)$alkenyloxy include ethenyloxy, propenyloxy, 1-propenyloxy, 2-propenyloxy, iso-propenyloxy, butenyloxy, 1-butenyloxy, 2-butenyloxy, 3-butenyloxy, iso-butenyloxy, sec-butenyloxy, tert-butenyloxy, pentenyloxy, 1-pentenyloxy, 2-pentenyloxy, 3-pentenyloxy, 4-pentenyloxy, iso-pentenyloxy, sec-pentenyloxy, tert-pentenyloxy, hexenyloxy, 1-hexenyloxy, 2-hexenyloxy, 3-hexenyloxy, 4-hexenyloxy, 5-hexenyloxy, iso-hexenyloxy, sec-hexenyloxy, tert-hexenyloxy and the like.

"$(C_2-C_6)$alkynyloxy" refers to —O—$(C_2-C_6)$alkynyl. Examples of $(C_2-C_6)$alkynyloxy include ethynyloxy, propynyloxy, 1-propynyloxy, 2-propynyloxy, butynyloxy, 1-butynyloxy, 2-butynyloxy, 3-butynyloxy, pentynyloxy, 1-pentynyloxy, 2-pentynyloxy, 3-pentynyloxy, 4-pentynyloxy, hexynyloxy, 1-hexynyloxy, 2-hexynyloxy, 3-hexynyloxy, 4-hexynyloxy, 5-hexynyloxy, and the like.

"$(C_1-C_6)$perhaloalkoxy" refers to —O—$(C_1-C_6)$perhaloalkyl. Examples of $(C_1-C_6)$-perhaloalkoxy include —$OCF_3$, —$OCCl_3$, —$OCF_2CF_3$, —$OCCl_2CF_3$, —OCCLFCCLF2, —$OCF(CF_3)_2$, —$OCH(CF_3)(CH_3)$, —$OCBr(CF_2)(CHCl_2)$ and the like.

"$(C_4-C_7)$heterocycloalkyl" refers to a 4-, 5-, 6-, or 7-membered, saturated or partially unsaturated, monocyclic heterocycle containing 1, 2, 3, or 4 ring heteroatoms each independently selected from nitrogen, oxygen, and sulfur, wherein said nitrogen and sulfur heteroatoms may optionally be oxidized and any nitrogen heteroatom may optionally be quaternized. Examples of $(C_4-C_7)$heterocycloalkyl groups include oxetanyl, azetidinyl, pyrrolidinyl, piperidinyl, piperazinyl, tetrahydro-oxazinyl, tetrahydrofuran, thiolane, dithiolane, pyrroline, pyrrolidine, pyrazoline, pyrazolidine, imidazoline, imidazolidine, tetrahydrofuranone, γ-butyrolactone, 2H-pyran, 4H-pyran, dioxolane, tetrahydropyran, dioxane, dihydrothiophene, piperazine, morpholine, thiomorpholine, oxazine, tetrahydro-oxazinyl, and the like.

"(C$_4$-C$_5$)heterocycloalkyl" refers to a 4- or 5-membered, saturated or partially unsaturated, monocyclic heterocycle containing 1, 2 or 3 ring heteroatoms each independently selected from nitrogen, oxygen, and sulfur, wherein said nitrogen and sulfur heteroatoms may optionally be oxidized and any nitrogen heteroatom may optionally be quaternized.

"(C$_4$)heterocycloalkyl" refers to a 4-membered, saturated or partially unsaturated, monocyclic heterocycle containing 1 ring heteroatom each independently selected from nitrogen, oxygen, and sulfur, wherein said nitrogen and sulfur heteroatom may optionally be oxidized and the nitrogen heteroatom may optionally be quaternized.

"(C$_6$-C$_{14}$)aryl" refers to a monovalent aromatic hydrocarbon group which may be monocyclic, bicyclic or tricyclic, wherein at least one ring in the system is aromatic and wherein each ring in the system contains 3, 4, 5, 6 or 7 ring members. Examples of (C$_6$-C$_{14}$)aryl groups include without limitation phenyl, naphthyl, indanyl, indenyl, tetralinyl, anthryl and phenanthryl. In some embodiments, the aryl is C$_6$ aryl. In some embodiments, the aryl is a bicyclic C$_9$-C$_{10}$ aryl. In some embodiments, the aryl is a tricyclic C$_{13}$-C$_{14}$ aryl. In some embodiments, the aryl is phenyl. In some embodiments, the aryl is naphthyl.

"(C$_6$-C$_{14}$)aryloxy" refers to —O—(C$_6$-C$_{14}$)aryl. Examples of (C$_6$-C$_{14}$)aryloxy groups include without limitation phenyloxy, naphthyloxy, indanyloxy, indenyloxy, tetralinyloxy, anthryloxy and phenanthryloxy.

"(5- or 6-membered)heteroaryl" refers to a monocyclic aromatic heterocycle ring of 5 or 6 members, i.e., a monocyclic aromatic ring comprising at least one ring heteroatom, e.g., 1, 2, 3, or 4 ring heteroatoms, each independently selected from nitrogen, oxygen, and sulfur. A (5- or 6-membered)heteroaryl group can be attached to the parent structure through a carbon or heteroatom. Examples of (5- or 6-membered)heteroaryls include pyridyl, pyrrolyl, pyrazolyl, furyl, imidazolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

"Benzo-fused heteroaromatic ring containing 1 heteroatom or 2 or 3 independently selected heteroatoms" refers to a heterocycle having 4, 5, 6, or 7 ring atoms and containing unsaturation, i.e., at least one double-bond, fused to benzene wherein the heterocycle contains 1, 2, or 3 heteroatom(s) independently selected from oxygen, nitrogen and sulfur. In one embodiment, the heterocycle of the benzo-fused heteroaromatic ring containing 1 heteroatom or 2 or 3 independently selected heteroatoms is a 5-membered heterocycle containing 1 heteroatom and one carbon-carbon double bond (not including carbon-carbon double bond of the benzene to which it is fused). In another embodiment, the heterocycle of the benzo-fused heteroaromatic ring containing 1 heteroatom or 2 or 3 independently selected heteroatoms is a 5-membered heterocycle containing 2 independently selected heteroatoms and one carbon-carbon double bond (not including carbon-carbon double bond of the benzene to which it is fused). In another embodiment, the heterocycle of the benzo-fused heteroaromatic ring containing 1 heteroatom or 2 or 3 independently selected heteroatoms is a 5-membered heterocycle containing 3 independently selected heteroatoms and one carbon-carbon double bond (not including carbon-carbon double bond of the benzene to which it is fused). In another embodiment, the heterocycle of the benzo-fused heteroaromatic ring containing 1 heteroatom or 2 or 3 independently selected heteroatoms is a 6-membered heterocycle containing 1 heteroatom and one carbon-carbon double bond (not including carbon-carbon double bond of the benzene to which it is fused). In another embodiment, the heterocycle of the benzo-fused heteroaromatic ring containing 1 heteroatom or 2 or 3 independently selected heteroatoms is a 6-membered heterocycle containing 2 independently selected heteroatoms and one carbon-carbon double bond (not including carbon-carbon double bond of the benzene to which it is fused). In another embodiment, the heterocycle of the benzo-fused heteroaromatic ring containing 1 heteroatom or 2 or 3 independently selected heteroatoms is a 6-membered heterocycle containing 3 independently selected heteroatoms and one carbon-carbon double bond (not including carbon-carbon double bond of the benzene to which it is fused). In another embodiment, the heterocycle of the benzo-fused heteroaromatic ring containing 1 heteroatom or 2 or 3 independently selected heteroatoms is a 6-membered heterocycle containing 1 heteroatom and two carbon-carbon double bonds (not including carbon-carbon double bond of the benzene to which it is fused). In another embodiment, the heterocycle of the benzo-fused heteroaromatic ring containing 1 heteroatom or 2 or 3 independently selected heteroatoms is a 6-membered heterocycle containing 2 independently selected heteroatoms and two carbon-carbon double bonds (not including carbon-carbon double bond of the benzene to which it is fused). Examples of benzo-fused heteromatic rings include benzopyrrole, benzofuran, benzothiophene, benzimidazole, benzopyrazole, benzoxazole, benzisoxazole, benzothiazole, benzisothiazole, quinolone and isoquinoline.

"Halo" refers to fluoro (—F), chloro (—Cl), bromo (—Br) and iodo (—I).

"Sulfo-n-butyl ether derivative of β-cyclodextrin" refers to β-cyclodextrin having at least one —OH group that is derivatized by replacing the hydrogen atom thereof with —(CH$_2$)$_4$—S(O)$_2$—OH or —(CH$_2$)$_4$—S(O)$_2$—O$^-$Z$^+$ to provide a —O—(CH$_2$)$_4$—S(O)$_2$—OH or —O—(CH$_2$)$_4$—S(O)$_2$—O$^-$Z$^+$ group, respectively, where Z$^+$ is a cation such as sodium, potassium, ammonium, tetramethylammonium, and the like. In one embodiment, each Z is sodium.

A compound of the disclosure can contain one, two, or more asymmetric centers and thus can give rise to enantiomers, diastereomers, and other stereoisomeric forms. The disclosure encompasses compounds with all such possible forms, as well as their racemic and resolved forms or any mixture thereof, unless specifically otherwise indicated. When a compound of the disclosure contains an olefinic double bond, a C═N double bond, or any other center of geometric asymmetry, it is intended to include all "geometric isomers", e.g., both Z and E geometric isomers, unless specifically otherwise indicated. All "tautomers", e.g., amine-imine, enamine-enimine, enamine-imine, urea-isourea, ketone-enol, amide-imidic acid, lactam-lactim, are intended to be encompassed by the disclosure as well unless specifically otherwise indicated.

Compounds of Formula (I)

One aspect of the disclosure provides a compound of formula (I):

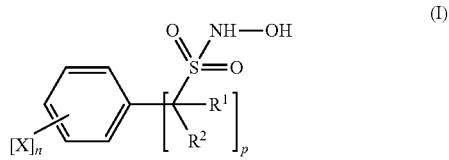

or a pharmaceutically acceptable salt thereof, wherein:

each X is independently selected from the group consisting of halo, —OH, —NO$_2$, —C≡N, (C$_1$-C$_6$)alkyl, (C$_1$-C$_6$)perhaloalkyl, (C$_1$-C$_6$)alkoxy, (C$_1$-C$_6$)perhaloalkoxy, (C$_6$-C$_{14}$)aryl, (C$_6$-C$_{14}$)aryloxy, (C$_4$-C$_7$)heterocycloalkyl, (5- or 6-membered)heteroaryl, (C$_6$-C$_{14}$)aryloxy, —SH, —SR', —S(O)R', —S(O)OH, —S(O)OR', —SO$_2$NHOH, —SO$_2$NH$_2$, —NH$_2$, —NHR', —NR'R", cycloalkoxy, —C(O)OH, —C(O)OR', —C(O)NH$_2$, C(O)NHR', —C(O)NR'R"; wherein said aryl, heterocycloalkyl and heteroaryl are unsubstituted or substituted with 1, 2, 3, 4 or 5 substituents selected from R$^4$;

each R$^4$ is independently selected from the group consisting of halo, —OH, —C≡N, —NO$_2$, —SH, =O, =S, =N—(C$_1$-C$_4$)alkyl, (C$_1$-C$_6$)alkyl, (C$_2$-C$_6$)alkenyl, (C$_2$-C$_6$)alkynyl, (C$_1$-C$_6$)alkoxy, (C$_2$-C$_6$)alkenyloxy, (C$_2$-C$_6$)alkynyloxy, (C$_6$-C$_{14}$)aryl, (C$_3$-C$_6$)cycloalkyl, (5- or 6-membered)heteroaryl, (C$_4$-C$_7$)heterocycloalkyl, —C(O)H, —C(O)NH$_2$, —C(O)OH, —NH—C(O)—NH$_2$, —NH—C(S), —NH$_2$, —SC≡N, —SO$_2$NH$_2$, —COR', —C(O)OR', —C(O)NHR', —C(O)NR'R", —NH$_2$, —NHR', —NR'R", —SR', —S(O)R', —S(O)OR', and —OR';

wherein R' and R" are independently selected from (C$_1$-C$_6$)alkyl, (C$_2$-C$_6$)alkenyl, (C$_2$-C$_6$)alkynyl, (C$_6$-C$_{14}$)aryl, (C$_3$-C$_6$)cycloalkyl, (5- or 6-membered)heteroaryl and (C$_4$-C$_7$)heterocycloalkyl;

n is 0, 1 or 2;

p is 1, 2 or 3; and

R$^1$ and R$^2$ are independently selected from H, halo and (C$_1$-C$_6$)alkyl optionally substituted with one or more independently selected halo(s), or R$^1$ and R$^2$ together with the carbon to which each is attached form (C$_3$-C$_6$)cycloalkyl or (C$_4$-C$_7$)heterocycloalkyl;

provided that:

a. if n is 0 and p is 1, then R$^1$ and R$^2$ are not H;

b. if n is 1, X is COOH, p is 1, then R$^1$ and R$^2$ are not H; and c. if n is 2, each X is methyl, p is 1, then R$^1$ and R$^2$ are not H.

In one embodiment, each X is independently selected from the group consisting of halo, —OH, —NO$_2$, —C≡N, (C$_1$-C$_6$)perhaloalkyl, (C$_1$-C$_6$)alkoxy, (C$_1$-C$_6$)perhaloalkoxy, (C$_6$-C$_{14}$)aryl, (C$_6$-C$_{14}$)aryloxy, (C$_4$-C$_7$)heterocycloalkyl, (5- or 6-membered)heteroaryl, (C$_6$-C$_{14}$)aryloxy, —SH, —SR', —S(O)R', —S(O)OH, —S(O)OR', —SO$_2$NHOH, —SO$_2$NH$_2$, —NH$_2$, —NHR', —NR'R", cycloalkoxy, —C(O)OR', —C(O)NH$_2$, C(O)NHR', —C(O)NR'R"; wherein said aryl, heterocycloalkyl and heteroaryl are unsubstituted or substituted with 1, 2, 3, 4 or 5 substituents selected from R$^4$.

In one embodiment, each X is independently selected from (C$_1$-C$_6$)alkyl, —NO$_2$, —C≡N, cyano and S(O)OR, wherein said alkyl is optionally substituted with one or more independently selected halo(s) and R is H or (C$_1$-C$_6$)alkyl, provided that if n is 2, each X is methyl, and p is 1, then R$^1$ and R$^2$ are not H.

In one embodiment, each X is independently selected from (C$_1$-C$_6$)alkyl, halo, —NO$_2$ and S(O)OR, wherein said alkyl is optionally substituted with one or more independently selected halo(s);

n is 1 or 2;

R is H or (C$_1$-C$_6$)alkyl;

p is 1; and

R$^1$ and R$^2$ are independently selected from H and (C$_1$-C$_6$)alkyl optionally substituted with one or more independently selected halo(s), or R$^1$ and R$^2$ together with the carbon to which each is attached form (C$_3$-C$_6$)cycloalkyl;

provided that if n is 2, each X is methyl, and p is 1, then R$^1$ and R$^2$ are not H.

In one embodiment, n is 0. In another embodiment, n is 1. In another embodiment, n is 2.

In one embodiment, at least one X is (C$_1$-C$_6$)alkyl. In another embodiment, at least one X is (C$_1$-C$_4$)alkyl. In one embodiment, at least one X is methyl. In one embodiment, at least one X is butyl. In another embodiment, n is 1 and X is (C$_1$-C$_6$)alkyl. In another embodiment, n is 1 and X is methyl. In another embodiment, n is 1 and X is butyl. In another embodiment, n is 2 and each X is independently (C$_1$-C$_6$)alkyl. In another embodiment, n is 2 and each X is methyl. In another embodiment, n is 2 and each X is butyl. In each embodiment in which at least one X is (C$_1$-C$_6$)alkyl, if n is 2, each X is methyl, and p is 1, then R$^1$ and R$^2$ are not H.

In one embodiment, at least one X is (C$_1$-C$_6$)alkyl substituted with one or more independently selected halo(s). In another embodiment, at least one X is (C$_1$-C$_6$)perhaloalkyl. In another embodiment, at least one X is methyl substituted with one or more independently selected halo(s). In another embodiment, at least one X is perfluoromethyl. In another embodiment, n is 1 and X is (C$_1$-C$_6$)perhaloalkyl. In another embodiment, n is 1 and X is methyl substituted with one or more independently selected halo(s). In another embodiment, n is 1 and X is perhalomethyl. In another embodiment, n is 1 and X is perfluoromethyl. In another embodiment, n is 2 and each X is independently (C$_1$-C$_6$)perhaloalkyl. In another embodiment, n is 2 and each X is independently methyl substituted with one or more independently selected halo(s). In another embodiment, n is 2 and each X is independently perhalomethyl. In another embodiment, n is 2 and each X is perfluoromethyl.

In one embodiment, at least one X is halo. In another embodiment, at least one X is bromo, chloro or fluoro. In another embodiment, at least one X is bromo. In another embodiment, at least one X is chloro. In another embodiment, at least one X is fluoro. In another embodiment, n is 1 and X is halo. In another embodiment, n is 1 and X is bromo, chloro or fluoro. In another embodiment, n is 1 and X is bromo. In another embodiment, n is 1 and X is chloro. In another embodiment, n is 1 and X is fluoro. In another embodiment, n is 2 and each X is independently halo. In another embodiment, n is 2 and each X is independently selected from bromo, chloro and fluoro. In another embodiment, n is 2 and each X is bromo. In another embodiment, n is 2 and each X is chloro. In another embodiment, n is 2 and each X is fluoro. In another embodiment, n is 2, one X is fluoro and the other is chloro.

In one embodiment, at least one X is nitro. In another embodiment, n is 1 and X is nitro. In another embodiment, n is 2 and each X is nitro.

In one embodiment, at least one X is cyano. In another embodiment, n is 1 and X is cyano. In another embodiment, n is 2 and each X is cyano.

In one embodiment, at least one X is S(O)OR. In another embodiment, at least one X is S(O)OR and R is H. In another embodiment, at least one X is S(O)OR and R is (C$_1$-C$_6$)alkyl. In another embodiment, at least one X is S(O)OR and R is methyl. In another embodiment, n is 1 and X is S(O)OR. In another embodiment, n is 1, X is S(O)OR and R is H. In another embodiment, n is 1, X is S(O)OR and R is (C$_1$-C$_6$)alkyl. In another embodiment, n is 1, X is S(O)OR and R is methyl. In another embodiment, n is 2 and each X is independently S(O)OR. In another embodiment, n is 2, each X is S(O)OR and R is H. In another embodiment, n is 2, each X is independently S(O)OR and R is $(C_1-C_6)$alkyl. In another embodiment, n is 2, each X is S(O)OR and R is methyl.

In one embodiment, p is 1. In another embodiment, p is 2. In another embodiment, p is 3.

In one embodiment, p is 1 and at least one of $R^1$ and $R^2$ is H. In another embodiment, each of $R^1$ and $R^2$ is H. In another embodiment, at least one of $R^1$ and $R^2$ is $(C_1-C_6)$alkyl optionally substituted with one or more independently selected halo(s). In another embodiment, at least one of $R^1$ and $R^2$ is $(C_1-C_6)$alkyl. In another embodiment, at least one of $R^1$ and $R^2$ is methyl. In another embodiment, at least one of $R^1$ and $R^2$ is $(C_1-C_6)$alkyl substituted with one or more independently selected halo(s). In another embodiment, at least one of $R^1$ and $R^2$ is methyl substituted with one or more independently selected halo(s). In another embodiment, at least one of $R^1$ and $R^2$ is methyl substituted with halo. In another embodiment, at least one of $R^1$ and $R^2$ is methyl substituted with one or more fluoro(s). In another embodiment, at least one of $R^1$ and $R^2$ is methyl substituted with fluoro.

In one embodiment, p is 1, $R^1$ is H and $R^2$ is $(C_1-C_6)$alkyl optionally substituted with one or more independently selected halo(s). In another embodiment, $R^1$ is H and $R^2$ is $(C_1-C_6)$alkyl. In another embodiment, $R^1$ is H and $R^2$ is methyl. In another embodiment, $R^1$ is H and $R^2$ is $(C_1-C_6)$alkyl substituted with one or more independently selected halo(s). In another embodiment, $R^1$ is H and $R^2$ is methyl substituted with one or more independently selected halo(s). In another embodiment, $R^1$ is H and $R^2$ is methyl substituted with halo. In another embodiment, $R^1$ is H and $R^2$ is methyl substituted with one or more fluoro(s). In another embodiment, $R^1$ is H and $R^2$ is methyl substituted with fluoro.

In one embodiment, p is 1 and each of $R^1$ and $R^2$ is $(C_1-C_6)$alkyl optionally substituted with one or more independently selected halo(s). In another embodiment, each of $R^1$ and $R^2$ is $(C_1-C_6)$alkyl. In another embodiment, each of $R^1$ and $R^2$ is methyl. In another embodiment, each of $R^1$ and $R^2$ is methyl optionally substituted with one or more independently selected halo(s). In another embodiment, each of $R^1$ and $R^2$ is $(C_1-C_6)$alkyl substituted with one or more independently selected halo(s). In another embodiment, each of $R^1$ and $R^2$ is methyl substituted with one or more independently selected halo(s). In another embodiment, each of $R^1$ and $R^2$ is methyl substituted with halo. In another embodiment, each of $R^1$ and $R^2$ is methyl substituted with one or more fluoro(s). In another embodiment, each of $R^1$ and $R^2$ is methyl substituted with fluoro.

In one embodiment, p is 1 and at least one of $R^1$ and $R^2$ is halo. In another embodiment, each of $R^1$ and $R^2$ is halo. In another embodiment, at least one of $R^1$ and $R^2$ is fluoro. In another embodiment, each of $R^1$ and $R^2$ is fluoro.

In one embodiment, p is 1, and $R^1$ and $R^2$ together with the carbon to which each is attached form $(C_3-C_6)$cycloalkyl. In another embodiment, $R^1$ and $R^2$ together with the carbon to which each is attached form cyclopropyl. In another embodiment, $R^1$ and $R^2$ together with the carbon to which each is attached form cyclopentyl. In another embodiment, $R^1$ and $R^2$ together with the carbon to which each is attached form cyclohexyl.

In one embodiment, p is 1, and $R^1$ and $R^2$ together with the carbon to which each is attached form $(C_4-C_7)$heterocycloalkyl. In one embodiment, $R^1$ and $R^2$ together with the carbon to which each is attached form $(C_4-C_5)$heterocycloalkyl. In another embodiment, $R^1$ and $R^2$ together with the carbon to which each is attached form $(C_4)$heterocloalkyl. In another embodiment, $R^1$ and $R^2$ together with the carbon to which each is attached form oxetanyl.

In one embodiment, p is 2 and at least one of $R^1$ and $R^2$ is H. In another embodiment, each of $R^1$ and $R^2$ is H. In another embodiment, at least one of $R^1$ and $R^2$ is $(C_1-C_6)$alkyl optionally substituted with one or more independently selected halo(s). In another embodiment, at least one of $R^1$ and $R^2$ is $(C_1-C_6)$alkyl. In another embodiment, at least one of $R^1$ and $R^2$ is methyl. In another embodiment, at least one of $R^1$ and $R^2$ is $(C_1-C_6)$alkyl substituted with one or more independently selected halo(s). In another embodiment, at least one of $R^1$ and $R^2$ is methyl substituted with one or more independently selected halo(s). In another embodiment, at least one of $R^1$ and $R^2$ is methyl substituted with halo. In another embodiment, at least one of $R^1$ and $R^2$ is methyl substituted with one or more fluoro(s). In another embodiment, at least one of $R^1$ and $R^2$ is methyl substituted with fluoro.

In one embodiment, p is 2, and $R^1$ is H and $R^2$ is $(C_1-C_6)$alkyl optionally substituted with one or more independently selected halo(s). In another embodiment, $R^1$ is H and $R^2$ is $(C_1-C_6)$alkyl. In another embodiment, $R^1$ is H and $R^2$ is methyl. In another embodiment, $R^1$ is H and $R^2$ is $(C_1-C_6)$alkyl substituted with one or more independently selected halo(s). In another embodiment, $R^1$ is H and $R^2$ is methyl substituted with one or more independently selected halo(s). In another embodiment, $R^1$ is H and $R^2$ is methyl substituted with halo. In another embodiment, $R^1$ is H and $R^2$ is methyl substituted with one or more fluoro(s). In another embodiment, $R^1$ is H and $R^2$ is methyl substituted with fluoro.

In one embodiment, p is 2, and each of $R^1$ and $R^2$ is $(C_1-C_6)$alkyl optionally substituted with one or more independently selected halo(s). In another embodiment, each of $R^1$ and $R^2$ is $(C_1-C_6)$alkyl. In another embodiment, each of $R^1$ and $R^2$ is methyl. In another embodiment, each of $R^1$ and $R^2$ is methyl optionally substituted with one or more independently selected halo(s). In another embodiment, each of $R^1$ and $R^2$ is $(C_1-C_6)$alkyl substituted with one or more independently selected halo(s). In another embodiment, each of $R^1$ and $R^2$ is methyl substituted with one or more independently selected halo(s). In another embodiment, each of $R^1$ and $R^2$ is methyl substituted with halo. In another embodiment, each of $R^1$ and $R^2$ is methyl substituted with one or more fluoro(s). In another embodiment, each of $R^1$ and $R^2$ is methyl substituted with fluoro.

In one embodiment, p is 2 and at least one of $R^1$ and $R^2$ is halo. In another embodiment, each of $R^1$ and $R^2$ is halo. In another embodiment, at least one of $R^1$ and $R^2$ is fluoro. In another embodiment, each of $R^1$ and $R^2$ is fluoro.

In one embodiment, n is 0, p is 1, and $R^1$ and $R^2$ are independently selected from halo and $(C_1-C_6)$alkyl optionally substituted with one or more independently selected halo(s), or $R^1$ and $R^2$ together with the carbon to which each is attached form $(C_3-C_6)$cycloalkyl or $(C_4-C_7)$heterocycloalkyl In another embodiment, $R^1$ and $R^2$ are independently selected from halo. In another embodiment, $R^1$ and $R^2$ are each fluoro. In another embodiment, $R^1$ and $R^2$ are independently selected $(C_1-C_6)$alkyl optionally substituted with one or more independently selected halo(s). In another embodiment, $R^1$ and $R^2$ are $(C_1-C_6)$alkyl. In another embodiment, $R^1$ and $R^2$ are each methyl. In another embodiment, $R^1$ and $R^2$ together with the carbon to which each is attached form $(C_3-C_6)$cycloalkyl or $(C_4-C_7)$heterocycloalkyl. In another embodiment, $R^1$ and $R^2$ together with the carbon to which each is attached form $(C_3-C_6)$cycloalkyl. In another embodiment, $R^1$ and $R^2$ together with the carbon to which each is attached form cyclopropyl. In another embodiment, R¹ and R² together with the carbon to which each is attached form (C₄-C₇)heterocycloalkyl. In another embodiment, R¹ and R² together with the carbon to which each is attached form oxetanyl.

In one embodiment, n is 0, p is 2, and R¹ and R² are independently selected from H, halo and (C₁-C₆)alkyl optionally substituted with one or more independently selected halo(s), or R¹ and R² together with the carbon to which each is attached form (C₃-C₆)cycloalkyl or (C₄-C₇) heterocycloalkyl In another embodiment, at least one of R¹ and R² is H. In another embodiment, each of R¹ and R² is H. In another embodiment, at least one of R¹ and R² is halo. In another embodiment, each of R¹ and R² is halo. In another embodiment, at least one of R¹ and R² is (C₁-C₆)alkyl optionally substituted with one or more independently selected halo(s). In another embodiment, each of R¹ and R² is (C₁-C₆)alkyl optionally substituted with one or more independently selected halo(s). In another embodiment, at least one of R¹ and R² is (C₁-C₆)alkyl. In another embodiment, each of R¹ and R² is (C₁-C₆)alkyl. In another embodiment, at least one of R¹ and R² is methyl. In another embodiment, each of R¹ and R² is methyl. In another embodiment, R¹ and R² together with the carbon to which each is attached form (C₃-C₆)cycloalkyl or (C₄-C₇)heterocycloalkyl. In another embodiment, R¹ and R² together with the carbon to which each is attached form (C₃-C₆)cycloalkyl. In another embodiment, R¹ and R² together with the carbon to which each is attached form (C₄-C₇)heterocycloalkyl.

Compounds of Formulae (II) and (III)
Another aspect of the disclosure provides a compound of formula (II) or (III):

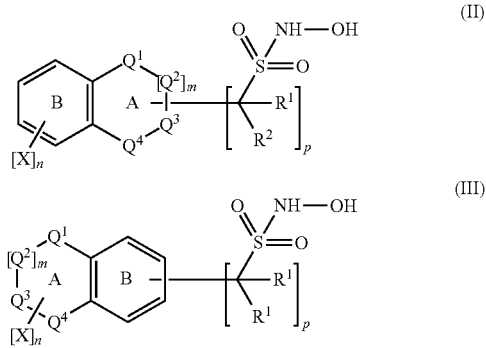

or a pharmaceutically acceptable salt thereof, wherein:
each X is independently selected from the group consisting of halo, —OH, —NO₂, —C≡N, (C₁-C₆)alkyl, (C₁-C₆) perhaloalkyl, (C₁-C₆)alkoxy, (C₁-C₆)perhaloalkoxy, (C₆-C₁₄)aryl, (C₆-C₁₄)aryloxy, (C₄-C₇)heterocycloalkyl, (5- or 6-membered)heteroaryl, (C₆-C₁₄)aryloxy, —SH, —SR', —S(O)R', —S(O)OH, —S(O)OR', —SO₂NHOH, —SO₂NH₂, —NH₂, —NHR', —NR'R", cycloalkoxy, —C(O)OH, —C(O)OR', —C(O)NH₂, C(O)NHR', —C(O) NR'R"; wherein said aryl, heterocycloalkyl and heteroaryl are unsubstituted or substituted with 1, 2, 3, 4 or 5 substituents selected from R⁴;
each R⁴ is independently selected from the group consisting of halo, —OH, —C≡N, —NO₂, —SH, =O, =S, =N—(C₁-C₄)alkyl, (C₁-C₆)alkyl, (C₂-C₆)alkenyl, (C₂-C₆) alkynyl, (C₁-C₆)alkoxy, (C₂-C₆)alkenyloxy, (C₂-C₆)alkynyloxy, (C₆-C₁₄)aryl, (C₃-C₆)cycloalkyl, (5- or 6-membered) heteroaryl, (C₄-C₇)heterocycloalkyl, —C(O)H, —C(O) NH₂, —C(O)OH, —NH—C(O)—NH₂, —NH—C(S), —NH₂, —SC≡N, —SO₂NH₂, —COR', —C(O)OR', —C(O) NHR', —C(O)NR'R", —NH₂, —NHR', —NR'R", —SR', —S(O)R', —S(O)OR', and —OR';
wherein R' and R" are independently selected from (C₁-C₆)alkyl, (C₂-C₆)alkenyl, (C₂-C₆)alkynyl, (C₆-C₁₄)aryl, (C₃-C₆)cycloalkyl, (5- or 6-membered)heteroaryl and (C₄-C₇)heterocycloalkyl;
m is 0 or 1;
n is 0, 1 or 2;
Q¹, Q², Q³ and Q⁴ are independently selected from —C—, —CH—, —N—, —NR³—, —O— and —S—, provided that at least one of Q¹, Q², Q³ and Q⁴ is —N—, —NR³—, —O— or —S—, and the A ring and the B ring together form a benzo-fused heteroaromatic ring containing 1 heteroatom or 2 or 3 independently selected heteroatoms;
p is 1, 2 or 3;
R¹ and R² are independently selected from H, halo and (C₁-C₆)alkyl optionally substituted with one or more independently selected halo(s), or R¹ and R² together with the carbon to which each is attached form (C₃-C₆)cycloalkyl or (C₄-C₇)heterocycloalkyl; and
R³ is H or (C₁-C₆)alkyl.

In one embodiment, each X is independently selected from (C₁-C₆)alkyl, halo, —C≡N, —NO₂ and S(O)OR, wherein said alkyl is optionally substituted with one or more independently selected halo(s) and R is H or (C₁-C₆)alkyl.

In one embodiment, each X is independently selected from (C₁-C₆)alkyl, halo, —NO₂ and S(O)OR, wherein said alkyl is optionally substituted with one or more independently selected halo(s);
m is 0 or 1;
n is 0, 1 or 2;
Q¹, Q², Q³ and Q⁴ are independently selected from —C—, —CH—, —N—, —NR³—, —O— and —S—, provided that at least one of Q¹, Q², Q³ and Q⁴ is —N—, —NR³—, —O— or —S—, and the A ring and the B ring together form a benzo-fused heteroaromatic ring containing 1 heteroatom or 2 or 3 independently selected heteroatoms;
R is H or (C₁-C₆)alkyl;
p is 1;
R¹ and R² are independently selected from H and (C₁-C₆)alkyl optionally substituted with one or more independently selected halo(s), or R¹ and R² together with the carbon to which each is attached form (C₃-C₆)cycloalkyl; and
R³ is H or (C₁-C₆)alkyl.

In one embodiment, the compound is of formula (II). In another embodiment, the compound is of formula (III).

In one embodiment, the m is 0. In another embodiment, m is 1.

In another embodiment, n is 0. In another embodiment, n is 1. In another embodiment, n is 2.

In one embodiment, m is 0 and n is 0. In another embodiment, m is 0 and n is 1. In another embodiment, m is 0 and n is 2. In another embodiment, m is 1 and n is 0. In another embodiment, m is 1 and n is 1. In another embodiment, m is 1 and n is 2.

In one embodiment, at least one X is (C₁-C₆)alkyl. In another embodiment, at least one X is (C₁-C₄)alkyl. In one embodiment, at least one X is methyl. In another embodiment, at least one X is butyl. In another embodiment, n is 1 and X is (C₁-C₆)alkyl. In another embodiment, n is 1 and X is (C₁-C₄)alkyl. In another embodiment, n is 1 and X is methyl. In another embodiment, n is 1 and X is butyl. In another embodiment, n is 2 and each X is independently ($C_1$-$C_6$)alkyl. In another embodiment, n is 2 and each X is independently ($C_1$-$C_4$)alkyl. In another embodiment, n is 2 and each X is methyl. In another embodiment, n is 2 and each X is butyl.

In one embodiment, at least one X is ($C_1$-$C_6$)alkyl substituted with one or more independently selected halo(s). In another embodiment, at least one X is ($C_1$-$C_6$)perhaloalkyl. In another embodiment, at least one X is methyl optionally substituted with one or more independently selected halo(s). In another embodiment, at least one X is methyl substituted with one or more independently selected halo(s). In another embodiment, at least one X is perfluoromethyl. In another embodiment, n is 1 and X is ($C_1$-$C_6$)perhaloalkyl. In another embodiment, n is 1 and X is methyl optionally substituted with one or more independently selected halo(s). In another embodiment, n is 1 and X is methyl substituted with one or more independently selected halo(s). In another embodiment, n is 1 and X is perhalomethyl. In another embodiment, n is 1 and X is perfluoromethyl. In another embodiment, n is 2 and each X is independently ($C_1$-$C_6$)perhaloalkyl. In another embodiment, n is 2 and each X is independently methyl optionally substituted with one or more independently selected halo(s). In another embodiment, n is 2 and each X is independently methyl substituted with one or more independently selected halo(s). In another embodiment, n is 2 and each X is independently perhalomethyl. In another embodiment, n is 2 and each X is perfluoromethyl.

In one embodiment, at least one X is halo. In another embodiment, at least one X is bromo, chloro or fluoro. In another embodiment, at least one X is bromo. In another embodiment, at least one X is chloro. In another embodiment, at least one X is fluoro. In another embodiment, n is 1 and X is halo. In another embodiment, n is 1 and X is bromo, chloro or fluoro. In another embodiment, n is 1 and X is bromo. In another embodiment, n is 1 and X is chloro. In another embodiment, n is 1 and X is fluoro. In another embodiment, n is 2 and each X is independently halo. In another embodiment, n is 2 and each X is independently selected from bromo, chloro and fluoro. In another embodiment, n is 2 and each X is bromo. In another embodiment, n is 2 and each X is chloro. In another embodiment, n is 2 and each X is fluoro.

In one embodiment, at least one X is nitro. In another embodiment, n is 1 and X is nitro. In another embodiment, n is 2 and each X is nitro.

In one embodiment, at least one X is cyano. In another embodiment, n is 1 and X is cyano. In another embodiment, n is 2 and each X is cyano.

In one embodiment, at least one X is S(O)OR. In another embodiment, at least one X is S(O)OR and R is H. In another embodiment, at least one X is S(O)OR and R is ($C_1$-$C_6$)alkyl. In another embodiment, at least one X is S(O)OR and R is methyl. In another embodiment, n is 1 and X is S(O)OR. In another embodiment, n is 1, X is S(O)OR and R is H. In another embodiment, n is 1, X is S(O)OR and R is ($C_1$-$C_6$)alkyl. In another embodiment, n is 1, X is S(O)OR and R is methyl. In another embodiment, n is 2 and each X is independently S(O)OR. In another embodiment, n is 2, each X is S(O)OR and R is H. In another embodiment, n is 2, each X is independently S(O)OR and R is ($C_1$-$C_6$)alkyl. In another embodiment, n is 2, each X is S(O)OR and R is methyl.

In one embodiment, p is 1. In another embodiment, p is 2. In another embodiment, p is 3.

In one embodiment, p is 1 and at least one of $R^1$ and $R^2$ is H. In another embodiment, each of $R^1$ and $R^2$ is H. In another embodiment, at least one of $R^1$ and $R^2$ is ($C_1$-$C_6$) alkyl optionally substituted with one or more independently selected halo(s). In another embodiment, at least one of $R^1$ and $R^2$ is ($C_1$-$C_6$)alkyl. In another embodiment, at least one of $R^1$ and $R^2$ is methyl. In another embodiment, at least one of $R^1$ and $R^2$ is ($C_1$-$C_6$)alkyl substituted with one or more independently selected halo(s). In another embodiment, at least one of $R^1$ and $R^2$ is methyl substituted with one or more independently selected halo(s). In another embodiment, at least one of $R^1$ and $R^2$ is methyl substituted with halo. In another embodiment, at least one of $R^1$ and $R^2$ is methyl substituted with one or more fluoro(s). In another embodiment, at least one of $R^1$ and $R^2$ is methyl substituted with fluoro.

In one embodiment, p is 1, $R^1$ is H, and $R^2$ is ($C_1$-$C_6$)alkyl optionally substituted with one or more independently selected halo(s). In another embodiment, $R^1$ is H and $R^2$ is ($C_1$-$C_6$)alkyl. In another embodiment, $R^1$ is H and $R^2$ is methyl. In another embodiment, $R^1$ is H and $R^2$ is ($C_1$-$C_6$)alkyl substituted with one or more independently selected halo(s). In another embodiment, $R^1$ is H and $R^2$ is methyl substituted with one or more independently selected halo(s). In another embodiment, $R^1$ is H and $R^2$ is methyl substituted with halo. In another embodiment, $R^1$ is H and $R^2$ is methyl substituted with one or more fluoro(s). In another embodiment, $R^1$ is H and $R^2$ is methyl substituted with fluoro.

In one embodiment, p is 1, and each of $R^1$ and $R^2$ is ($C_1$-$C_6$)alkyl optionally substituted with one or more independently selected halo(s). In another embodiment, each of $R^1$ and $R^2$ is ($C_1$-$C_6$)alkyl. In another embodiment, each of $R^1$ and $R^2$ is methyl. In another embodiment, each of $R^1$ and $R^2$ is methyl optionally substituted with one or more independently selected halo(s). In another embodiment, each of $R^1$ and $R^2$ is ($C_1$-$C_6$)alkyl substituted with one or more independently selected halo(s). In another embodiment, each of $R^1$ and $R^2$ is methyl substituted with one or more independently selected halo(s). In another embodiment, each of $R^1$ and $R^2$ is methyl substituted with halo. In another embodiment, each of $R^1$ and $R^2$ is methyl substituted with one or more fluoro(s). In another embodiment, each of $R^1$ and $R^2$ is methyl substituted with fluoro.

In one embodiment, p is 1 and at least one of $R^1$ and $R^2$ is halo. In another embodiment, each of $R^1$ and $R^2$ is halo. In another embodiment, at least one of $R^1$ and $R^2$ is fluoro. In another embodiment, each of $R^1$ and $R^2$ is fluoro.

In one embodiment, p is 1, and $R^1$ and $R^2$ together with the carbon to which each is attached form ($C_3$-$C_6$)cycloalkyl. In another embodiment, $R^1$ and $R^2$ together with the carbon to which each is attached form cyclopropyl. In another embodiment, $R^1$ and $R^2$ together with the carbon to which each is attached form cyclopentyl. In another embodiment, $R^1$ and $R^2$ together with the carbon to which each is attached form cyclohexyl.

In one embodiment, p is 1, and $R^1$ and $R^2$ together with the carbon to which each is attached form ($C_4$-$C_7$)heterocycloalkyl. In one embodiment, $R^1$ and $R^2$ together with the carbon to which each is attached form ($C_4$-$C_5$)heterocycloalkyl. In another embodiment, $R^1$ and $R^2$ together with the carbon to which each is attached form ($C_4$)heterocycloalkyl. In another embodiment, $R^1$ and $R^2$ together with the carbon to which each is attached form oxetanyl.

In one embodiment, p is 2, and at least one of $R^1$ and $R^2$ is H. In another embodiment, each of $R^1$ and $R^2$ is H. In another embodiment, at least one of $R^1$ and $R^2$ is ($C_1$-$C_6$) alkyl optionally substituted with one or more independently selected halo(s). In another embodiment, at least one of $R^1$ and $R^2$ is ($C_1$-$C_6$)alkyl. In another embodiment, at least one of $R^1$ and $R^2$ is methyl. In another embodiment, at least one of $R^1$ and $R^2$ is $(C_1-C_6)$alkyl substituted with one or more independently selected halo(s). In another embodiment, at least one of $R^1$ and $R^2$ is methyl substituted with one or more independently selected halo(s). In another embodiment, at least one of $R^1$ and $R^2$ is methyl substituted with halo. In another embodiment, at least one of $R^1$ and $R^2$ is methyl substituted with one or more fluoro(s). In another embodiment, at least one of $R^1$ and $R^2$ is methyl substituted with fluoro.

In one embodiment, p is 2, $R^1$ is H, and $R^2$ is $(C_1-C_6)$alkyl optionally substituted with one or more independently selected halo(s). In another embodiment, $R^1$ is H and $R^2$ is $(C_1-C_6)$alkyl. In another embodiment, $R^1$ is H and $R^2$ is methyl. In another embodiment, $R^1$ is H and $R^2$ is $(C_1-C_6)$alkyl substituted with one or more independently selected halo(s). In another embodiment, $R^1$ is H and $R^2$ is methyl substituted with one or more independently selected halo(s). In another embodiment, $R^1$ is H and $R^2$ is methyl substituted with halo. In another embodiment, $R^1$ is H and $R^2$ is methyl substituted with one or more fluoro(s). In another embodiment, $R^1$ is H and $R^2$ is methyl substituted with fluoro.

In one embodiment, p is 2, and each of $R^1$ and $R^2$ is $(C_1-C_6)$alkyl optionally substituted with one or more independently selected halo(s). In another embodiment, each of $R^1$ and $R^2$ is $(C_1-C_6)$alkyl. In another embodiment, each of $R^1$ and $R^2$ is methyl. In another embodiment, each of $R^1$ and $R^2$ is methyl optionally substituted with one or more independently selected halo(s). In another embodiment, each of $R^1$ and $R^2$ is $(C_1-C_6)$alkyl substituted with one or more independently selected halo(s). In another embodiment, each of $R^1$ and $R^2$ is methyl substituted with one or more independently selected halo(s). In another embodiment, each of $R^1$ and $R^2$ is methyl substituted with halo. In another embodiment, each of $R^1$ and $R^2$ is methyl substituted with one or more fluoro(s). In another embodiment, each of $R^1$ and $R^2$ is methyl substituted with fluoro.

In one embodiment, p is 2 and at least one of $R^1$ and $R^2$ is halo. In another embodiment, each of $R^1$ and $R^2$ is halo. In another embodiment, at least one of $R^1$ and $R^2$ is fluoro. In another embodiment, each of $R^1$ and $R^2$ is fluoro.

In one embodiment, the A ring and the B ring together form a heteroaromatic ring containing 1 heteroatom or 2 or 3 independently selected heteroatoms. In another embodiment, the A ring and the B ring together form a heteroaromatic ring containing 1 heteroatom or independently selected 2 heteroatoms. In another embodiment, the A ring and the B ring together form a heteroaromatic ring containing 1 heteroatom. In another embodiment, the A ring and the B ring together form a heteroaromatic ring containing 2 heteroatoms. In another embodiment, the A ring and the B ring together form a heteroaromatic ring containing 3 heteroatoms.

In one embodiment, at least one of $Q^1$, $Q^2$, $Q^3$ and $Q^4$ is —N—. In another embodiment, at least one of $Q^1$, $Q^2$, $Q^3$ and $Q^4$ is —NR³—. In another embodiment, at least one of $Q^1$, $Q^2$, $Q^3$ and $Q^4$ is —O—. In another embodiment, at least one of $Q^1$, $Q^2$, $Q^3$ and $Q^4$ is —S—. In another embodiment, at least one of $Q^1$, $Q^2$, $Q^3$ and $Q^4$ is —N— and at least one of $Q^1$, $Q^2$, $Q^3$ and $Q^4$ is —O—. In another embodiment, m is 0 and at least one of $Q^1$, $Q^2$, $Q^3$ and $Q^4$ is —N—. In another embodiment, m is 0 and at least one of $Q^1$, $Q^2$, $Q^3$ and $Q^4$ is —NR³—. In another embodiment, m is 0 and at least one of $Q^1$, $Q^2$, $Q^3$ and $Q^4$ is —O—. In another embodiment, m is 0 and at least one of $Q^1$, $Q^2$, $Q^3$ and $Q^4$ is —S—. In another embodiment, m is 0, at least one of $Q^1$, $Q^2$, $Q^3$ and $Q^4$ is —N— and at least one of $Q^1$, $Q^2$, $Q^3$ and $Q^4$ is —O—. In another embodiment, m is 0, at least one of $Q^1$, $Q^2$, $Q^3$ and $Q^4$ is —NR³— and at least one of $Q^1$, $Q^2$, $Q^3$ and $Q^4$ is —O—. In another embodiment, m is 1 and at least one of $Q^1$, $Q^2$, $Q^3$ and $Q^4$ is —N—. In another embodiment, m is 1 and at least one of $Q^1$, $Q^2$, $Q^3$ and $Q^4$ is —NR³—. In another embodiment, m is 1 and at least one of $Q^1$, $Q^2$, $Q^3$ and $Q^4$ is —O—. In another embodiment, m is 1 and at least one of $Q^1$, $Q^2$, $Q^3$ and $Q^4$ is —S—. In another embodiment, m is 1, at least one of $Q^1$, $Q^2$, $Q^3$ and $Q^4$ is —N— and at least one of $Q^1$, $Q^2$, $Q^3$ and $Q^4$ is —O—. In another embodiment, m is 1, at least one of $Q^1$, $Q^2$, $Q^3$ and $Q^4$ is —NR³— and at least one of $Q^1$, $Q^2$, $Q^3$ and $Q^4$ is —O—.

In one embodiment, the A ring and the B ring together form a heteroaromatic ring selected from benzopyrrole, benzofuran, benzothiophene, benzimidazole, benzopyrazole, benzoxazole, benzisoxazole, benzothiazole, benzisothiazole, benzotriazole, benzofurazan, benzothiadiazole, benzodithiazole, quinolone, isoquinoline, benzopyran, benzothiopyran, benzodiazine, benzoxazine, benzothiazine, benzodioxine, benzodithiine and benzotriazine. In another embodiment, the A ring and the B ring together form a heteroaromatic ring selected from benzopyrrole, benzofuran, benzothiophene, benzimidazole, benzopyrazole, benzoxazole, benzisoxazole, benzothiazole, benzisothiazole, quinolone and isoquinoline. In another embodiment, the A ring and the B ring together form a heteroaromatic ring selected form benzofuran, benzoisoxazole and benzoxazole. In another embodiment, the A ring and the B ring together form benzofuran. In another embodiment, the A ring and the B ring together form benzoxazole. In another embodiment, the A ring and the B ring together form benzoisoxazole. In another embodiment, the A ring and the B ring together form benzoxazole and the compound is of formula (II). In another embodiment, the A ring and the B ring together form benzoxazole and the compound is of formula (III). In another embodiment, the A ring and the B ring together form benzoisoxazole and the compound is of formula (II). In another embodiment, the A ring and the B ring together form benzoisoxazole and the compound is of formula (III). In another embodiment, the A ring and the B ring together form benzofuran and the compound is of formula (II). In another embodiment, the A ring and the B ring together form benzofuran and the compound is of formula (III).

Compounds of Formula (IV)

Another aspect of the disclosure provides a compound of formula (IV):

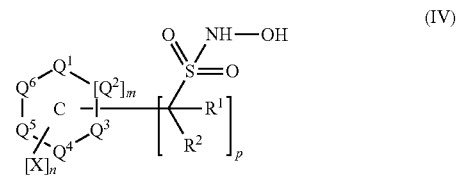

or a pharmaceutically acceptable salt thereof, wherein:

each X is independently selected from the group consisting of halo, —OH, —NO₂, —C≡N, $(C_1-C_6)$alkyl, $(C_1-C_6)$perhaloalkyl, $(C_1-C_6)$alkoxy, $(C_1-C_6)$perhaloalkoxy, $(C_6-C_{14})$aryl, $(C_6-C_{14})$aryloxy, $(C_4-C_7)$heterocycloalkyl, (5- or 6-membered)heteroaryl, $(C_6-C_{14})$aryloxy, —SH, —SR', —S(O)R', —S(O)OH, —S(O)OR', —SO₂NHOH, —SO₂NH₂, —NH₂, —NHR', —NR'R'', cycloalkoxy, —C(O)OH, —C(O)OR', —C(O)NH₂, C(O)NHR', —C(O)

NR'R"; wherein said aryl, heterocycloalkyl and heteroaryl are unsubstituted or substituted with 1, 2, 3, 4 or 5 substituents selected from $R^4$;

each $R^4$ is independently selected from the group consisting of halo, —OH, —C≡N, —NO$_2$, —SH, =O, =S, =N—(C$_1$-C$_4$)alkyl, (C$_1$-C$_6$)alkyl, (C$_2$-C$_6$)alkenyl, (C$_2$-C$_6$)alkynyl, (C$_1$-C$_6$)alkoxy, (C$_2$-C$_6$)alkenyloxy, (C$_2$-C$_6$)alkynyloxy, (C$_6$-C$_{14}$)aryl, (C$_3$-C$_6$)cycloalkyl, (5- or 6-membered)heteroaryl, (C$_4$-C$_7$)heterocycloalkyl, —C(O)H, —C(O)NH$_2$, —C(O)OH, —NH—C(O)—NH$_2$, —NH—C(S), —NH$_2$, —SC≡N, —SO$_2$NH$_2$, —COR', —C(O)OR', —C(O)NHR', —C(O)NR'R", —NH$_2$, —NHR', —NR'R", —SR', —S(O)R', —S(O)OR', and —OR';

wherein R' and R" are independently selected from (C$_1$-C$_6$)alkyl, (C$_2$-C$_6$)alkenyl, (C$_2$-C$_6$)alkynyl, (C$_6$-C$_{14}$)aryl, (C$_3$-C$_6$)cycloalkyl, (5- or 6-membered)heteroaryl and (C$_4$-C$_7$)heterocycloalkyl;

m is 0 or 1;

n is 0, 1 or 2;

$Q^1$, $Q^2$, $Q^3$, $Q^4$, $Q^5$ and $Q^6$ are independently selected from —C—, —CH—, —N—, —NR$^3$—, —O— and —S—, provided that at least one of $Q^1$, $Q^2$, $Q^3$, $Q^4$, $Q^5$ and $Q^6$ is —N—, —NR$^3$—, —O— or —S—, such that the C ring is a heteroaromatic ring;

p is 1, 2 or 3;

$R^1$ and $R^2$ are independently selected from H, halo and (C$_1$-C$_6$)alkyl optionally substituted with one or more independently selected halo(s), or $R^1$ and $R^2$ together with the carbon to which each is attached form (C$_3$-C$_6$)cycloalkyl or (C$_4$-C$_7$)heterocycloalkyl; and $R^3$ is H or (C$_1$-C$_6$)alkyl;

provided that if n is 0, p is 1, and ring C is furanyl, then $R^1$ and $R^2$ are not H.

In one embodiment, each X is independently selected from (C$_1$-C$_6$)alkyl, halo, —NO$_2$, —C≡N and S(O)OR, wherein said alkyl is optionally substituted with one or more independently selected halo(s) and R is H or (C$_1$-C$_6$)alkyl.

In one embodiment, each X is independently selected from (C$_1$-C$_6$)alkyl, halo, —NO$_2$ and S(O)OR, wherein said alkyl is optionally substituted with one or more independently selected halo(s);

m is 0 or 1;

n is 0, 1 or 2;

$Q^1$, $Q^2$, $Q^3$, $Q^4$, $Q^5$ and $Q^6$ are independently selected from —C—, —CH—, —N—, —NR$^3$—, —O— and —S—, provided that at least one of $Q^1$, $Q^2$, $Q^3$, $Q^4$, $Q^5$ and $Q^6$ is —N—, —NR$^3$—, —O— or —S—, such that the C ring is a heteroaromatic ring;

R is H or (C$_1$-C$_6$)alkyl;

p is 1;

$R^1$ and $R^2$ are independently selected from H and (C$_1$-C$_6$)alkyl optionally substituted with one or more independently selected halo(s), or $R^1$ and $R^2$ together with the carbon to which each is attached form (C$_3$-C$_6$)cycloalkyl; and $R^3$ is H or (C$_1$-C$_6$)alkyl.

In one embodiment, m is 0. In another embodiment, m is 1.

In one embodiment, n is 0. In another embodiment, n is 1. In another embodiment, n is 2.

In one embodiment, m is 0 and n is 0. In another embodiment, m is 0 and n is 1. In another embodiment, m is 0 and n is 2. In another embodiment, m is 1 and n is 0. In another embodiment, m is 1 and n is 1. In another embodiment, m is 1 and n is 2.

In one embodiment, at least one X is (C$_1$-C$_6$)alkyl. In one embodiment, at least one X is (C$_1$-C$_4$)alkyl. In one embodiment, at least one X is methyl. In another embodiment, at least one X is butyl. In another embodiment, n is 1 and X is (C$_1$-C$_6$)alkyl. In another embodiment, n is 1 and X is (C$_1$-C$_4$)alkyl. In another embodiment, n is 1 and X is methyl. In another embodiment, n is 1 and X is butyl. In another embodiment, n is 2 and each X is independently (C$_1$-C$_6$)alkyl. In another embodiment, n is 2 and each X is independently (C$_1$-C$_4$)alkyl. In another embodiment, n is 2 and each X is methyl. In another embodiment, n is 2 and each X is butyl.

In one embodiment, at least one X is (C$_1$-C$_6$)alkyl substituted with one or more independently selected halo(s). In another embodiment, at least one X is (C$_1$-C$_6$)perhaloalkyl. In another embodiment, at least one X is methyl optionally substituted with one or more independently selected halo(s). In another embodiment, at least one X is methyl substituted with one or more independently selected halo(s). In another embodiment, at least one X is perfluoromethyl. In another embodiment, n is 1 and X is (C$_1$-C$_6$)perhaloalkyl. In another embodiment, n is 1 and X is methyl optionally substituted with one or more independently selected halo(s). In another embodiment, n is 1 and X is methyl substituted with one or more independently selected halo(s). In another embodiment, n is 1 and X is perhalomethyl. In another embodiment, n is 1 and X is perfluoromethyl. In another embodiment, n is 2 and each X is independently (C$_1$-C$_6$)perhaloalkyl. In another embodiment, n is 2 and each X is independently methyl optionally substituted with one or more independently selected halo(s). In another embodiment, n is 2 and each X is independently methyl substituted with one or more independently selected halo(s). In another embodiment, n is 2 and each X is independently perhalomethyl. In another embodiment, n is 2 and each X is perfluoromethyl.

In one embodiment, at least one X is halo. In another embodiment, at least one X is bromo, chloro or fluoro. In another embodiment, at least one X is bromo. In another embodiment, at least one X is chloro. In another embodiment, at least one X is fluoro. In another embodiment, n is 1 and X is halo. In another embodiment, n is 1 and X is bromo, chloro or fluoro. In another embodiment, n is 1 and X is bromo. In another embodiment, n is 1 and X is chloro. In another embodiment, n is 1 and X is fluoro. In another embodiment, n is 2 and each X is independently halo. In another embodiment, n is 2 and each X is independently selected from bromo, chloro and fluoro. In another embodiment, n is 2 and each X is bromo. In another embodiment, n is 2 and each X is chloro. In another embodiment, n is 2 and each X is fluoro.

In one embodiment, at least one X is nitro. In another embodiment, n is 1 and X is nitro. In another embodiment, n is 2 and each X is nitro.

In one embodiment, at least one X is cyano. In another embodiment, n is 1 and X is cyano. In another embodiment, n is 2 and each X is cyano.

In one embodiment, at least one X is S(O)OR. In another embodiment, at least one X is S(O)OR and R is H. In another embodiment, at least one X is S(O)OR and R is (C$_1$-C$_6$)alkyl. In another embodiment, at least one X is S(O)OR and R is methyl. In another embodiment, n is 1 and X is S(O)OR. In another embodiment, n is 1, X is S(O)OR and R is H. In another embodiment, n is 1, X is S(O)OR and R is (C$_1$-C$_6$)alkyl. In another embodiment, n is 1, X is S(O)OR and R is methyl. In another embodiment, n is 2 and each X is independently S(O)OR. In another embodiment, n is 2, each X is S(O)OR and R is H. In another embodiment, n is 2, each X is independently S(O)OR and R is $(C_1-C_6)$alkyl. In another embodiment, n is 2, each X is S(O)OR and R is methyl.

In one embodiment, p is 1. In another embodiment, p is 2. In another embodiment, p is 3.

In one embodiment, p is 1, and at least one of $R^1$ and $R^2$ is H. In another embodiment, each of $R^1$ and $R^2$ is H. In another embodiment, at least one of $R^1$ and $R^2$ is $(C_1-C_6)$alkyl optionally substituted with one or more independently selected halo(s). In another embodiment, at least one of $R^1$ and $R^2$ is $(C_1-C_6)$alkyl. In another embodiment, at least one of $R^1$ and $R^2$ is methyl. In another embodiment, at least one of $R^1$ and $R^2$ is $(C_1-C_6)$alkyl substituted with one or more independently selected halo(s). In another embodiment, at least one of $R^1$ and $R^2$ is methyl substituted with one or more independently selected halo(s). In another embodiment, at least one of $R^1$ and $R^2$ is methyl substituted with halo. In another embodiment, at least one of $R^1$ and $R^2$ is methyl substituted with one or more fluoro(s). In another embodiment, at least one of $R^1$ and $R^2$ is methyl substituted with fluoro.

In one embodiment, p is 1, $R^1$ is H, and $R^2$ is $(C_1-C_6)$alkyl optionally substituted with one or more independently selected halo(s). In another embodiment, $R^1$ is H and $R^2$ is $(C_1-C_6)$alkyl. In another embodiment, $R^1$ is H and $R^2$ is methyl. In another embodiment, $R^1$ is H and $R^2$ is $(C_1-C_6)$alkyl substituted with one or more independently selected halo(s). In another embodiment, $R^1$ is H and $R^2$ is methyl substituted with one or more independently selected halo(s). In another embodiment, $R^1$ is H and $R^2$ is methyl substituted with halo. In another embodiment, $R^1$ is H and $R^2$ is methyl substituted with one or more fluoro(s). In another embodiment, $R^1$ is H and $R^2$ is methyl substituted with fluoro.

In one embodiment, p is 1, and each of $R^1$ and $R^2$ is $(C_1-C_6)$alkyl optionally substituted with one or more independently selected halo(s). In another embodiment, each of $R^1$ and $R^2$ is $(C_1-C_6)$alkyl. In another embodiment, each of $R^1$ and $R^2$ is methyl. In another embodiment, each of $R^1$ and $R^2$ is methyl optionally substituted with one or more independently selected halo(s). In another embodiment, each of $R^1$ and $R^2$ is $(C_1-C_6)$alkyl substituted with one or more independently selected halo(s). In another embodiment, each of $R^1$ and $R^2$ is methyl substituted with one or more independently selected halo(s). In another embodiment, each of $R^1$ and $R^2$ is methyl substituted with halo. In another embodiment, each of $R^1$ and $R^2$ is methyl substituted with one or more fluoro(s). In another embodiment, each of $R^1$ and $R^2$ is methyl substituted with fluoro.

In one embodiment, p is 1, and at least one of $R^1$ and $R^2$ is halo. In another embodiment, each of $R^1$ and $R^2$ is halo. In another embodiment, at least one of $R^1$ and $R^2$ is fluoro. In another embodiment, each of $R^1$ and $R^2$ is fluoro.

In one embodiment, p is 1, and $R^1$ and $R^2$ together form with the carbon to which each is attached $(C_3-C_6)$cycloalkyl. In another embodiment, $R^1$ and $R^2$ together with the carbon to which each is attached form cyclopropyl. In another embodiment, $R^1$ and $R^2$ together with the carbon to which each is attached form cyclopentyl. In another embodiment, $R^1$ and $R^2$ together with the carbon to which each is attached form cyclohexyl.

In one embodiment, p is 1, and $R^1$ and $R^2$ together with the carbon to which each is attached form $(C_4-C_7)$heterocycloalkyl. In one embodiment, $R^1$ and $R^2$ together with the carbon to which each is attached form $(C_4-C_5)$heterocycloalkyl. In another embodiment, $R^1$ and $R^2$ together with the carbon to which each is attached form $(C_4)$heterocloalkyl. In another embodiment, $R^1$ and $R^2$ together with the carbon to which each is attached form oxetanyl.

In one embodiment, p is 2, and at least one of $R^1$ and $R^2$ is H. In another embodiment, each of $R^1$ and $R^2$ is H. In another embodiment, at least one of $R^1$ and $R^2$ is $(C_1-C_6)$alkyl optionally substituted with one or more independently selected halo(s). In another embodiment, at least one of $R^1$ and $R^2$ is $(C_1-C_6)$alkyl. In another embodiment, at least one of $R^1$ and $R^2$ is methyl. In another embodiment, at least one of $R^1$ and $R^2$ is $(C_1-C_6)$alkyl substituted with one or more independently selected halo(s). In another embodiment, at least one of $R^1$ and $R^2$ is methyl substituted with one or more independently selected halo(s). In another embodiment, at least one of $R^1$ and $R^2$ is methyl substituted with halo. In another embodiment, at least one of $R^1$ and $R^2$ is methyl substituted with one or more fluoro(s). In another embodiment, at least one of $R^1$ and $R^2$ is methyl substituted with fluoro.

In one embodiment, p is 2, $R^1$ is H, and $R^2$ is $(C_1-C_6)$alkyl optionally substituted with one or more independently selected halo(s). In another embodiment, $R^1$ is H and $R^2$ is $(C_1-C_6)$alkyl. In another embodiment, $R^1$ is H and $R^2$ is methyl. In another embodiment, $R^1$ is H and $R^2$ is $(C_1-C_6)$alkyl substituted with one or more independently selected halo(s). In another embodiment, $R^1$ is H and $R^2$ is methyl substituted with one or more independently selected halo(s). In another embodiment, $R^1$ is H and $R^2$ is methyl substituted with halo. In another embodiment, $R^1$ is H and $R^2$ is methyl substituted with one or more fluoro(s). In another embodiment, $R^1$ is H and $R^2$ is methyl substituted with fluoro.

In one embodiment, p is 2, and each of $R^1$ and $R^2$ is $(C_1-C_6)$alkyl optionally substituted with one or more independently selected halo(s). In another embodiment, each of $R^1$ and $R^2$ is $(C_1-C_6)$alkyl. In another embodiment, each of $R^1$ and $R^2$ is methyl. In another embodiment, each of $R^1$ and $R^2$ is methyl optionally substituted with one or more independently selected halo(s). In another embodiment, each of $R^1$ and $R^2$ is $(C_1-C_6)$alkyl substituted with one or more independently selected halo(s). In another embodiment, each of $R^1$ and $R^2$ is methyl substituted with one or more independently selected halo(s). In another embodiment, each of $R^1$ and $R^2$ is methyl substituted with halo. In another embodiment, each of $R^1$ and $R^2$ is methyl substituted with one or more fluoro(s). In another embodiment, each of $R^1$ and $R^2$ is methyl substituted with fluoro.

In one embodiment, p is 2, and at least one of $R^1$ and $R^2$ is halo. In another embodiment, each of $R^1$ and $R^2$ is halo. In another embodiment, at least one of $R^1$ and $R^2$ is fluoro. In another embodiment, each of $R^1$ and $R^2$ is fluoro.

In one embodiment, the C ring is a heteroaromatic ring containing 1 heteroatom or 2 or 3 independently selected heteroatoms. In another embodiment, the C ring is a heteroaromatic ring containing 1 heteroatom or independently selected 2 heteroatoms. In another embodiment, the C ring is a heteroaromatic ring containing 1 heteroatom. In another embodiment, the C ring is a heteroaromatic ring containing 2 heteroatoms. In another embodiment, the C ring is a heteroaromatic ring containing 3 heteroatoms.

In one embodiment, at least one of $Q^1$, $Q^2$, $Q^3$ and $Q^4$ is —N—. In another embodiment, at least one of $Q^1$, $Q^2$, $Q^3$ and $Q^4$ is —$NR^3$—. In another embodiment, at least one of $Q^1$, $Q^2$, $Q^3$ and $Q^4$ is —O—. In another embodiment, at least one of $Q^1$, $Q^2$, $Q^3$ and $Q^4$ is —S—. In another embodiment, at least one of $Q^1$, $Q^2$, $Q^3$ and $Q^4$ is —N— and at least one of $Q^1$, $Q^2$, $Q^3$ and $Q^4$ is —O—. In another embodiment, m is 0 and at least one of $Q^1$, $Q^2$, $Q^3$ and $Q^4$ is —N—. In another embodiment, m is 0 and at least one of $Q^1$, $Q^2$, $Q^3$ and $Q^4$ is —$NR^3$—. In another embodiment, m is 0 and at least one of $Q^1$, $Q^2$, $Q^3$ and $Q^4$ is —O—. In another embodiment, m is 0 and at least one of $Q^1$, $Q^2$, $Q^3$ and $Q^4$ is —S—. In another embodiment, m is 0 and at least one of $Q^1$, $Q^2$, $Q^3$ and $Q^4$ is —N—. In another embodiment, m is 1 and at least one of $Q^1$, $Q^2$, $Q^3$ and $Q^4$ is —$NR^3$—. In another embodiment, m is 1 and at least one of $Q^1$, $Q^2$, $Q^3$ and $Q^4$ is —O—. In another embodiment, m is 1 and at least one of $Q^1$, $Q^2$, $Q^3$ and $Q^4$ is —S—. In another embodiment, m is 1 and one of $Q^1$, $Q^2$, $Q^3$ and $Q^4$ is —N—. In another embodiment, m is 1 and one of $Q^1$, $Q^2$, $Q^3$ and $Q^4$ is —$NR^3$—. In another embodiment, m is 1 and one of $Q^1$, $Q^2$, $Q^3$ and $Q^4$ is —O—. In another embodiment, m is 1 and one of $Q^1$, $Q^2$, $Q^3$ and $Q^4$ is —S—.

In one embodiment, the C ring is a heteroaromatic ring selected from pyrrole, furan, thiophene, imidazole, pyrazole, oxazole, isoxazole, thiazole, isothiazole, triazole, furazan, oxadiazole, thiadiazole, dithiazole, pyridine, pyrimidine, diazine, oxazine, thiazine, dithiine and triazine. In another embodiment, the C ring is a heteroaromatic ring selected from pyrrole, furan, thiophene, imidazole, pyrazole, oxazole, isoxazole, thiazole, isothiazole, pyridine, pyrimidine, diazine, oxazine, thiazine and dithiine. In another embodiment, the C ring is pyridine. In another embodiment, the C ring is pyrimidine. In another embodiment, the C ring is thiophene. In another embodiment, the C ring is furan.

In one embodiment, n is 0, m is 1, and p is 1, 2 or 3. In another embodiment, p is 1. In another embodiment, p is 2. In another embodiment, p is 3.

In one embodiment, n is 0, m is 0, and p is 2 or 3. In another embodiment, p is 2. In another embodiment, p is 3.

In one embodiment, n is 1, m is 0, and p is 1, 2 or 3. In another embodiment, p is 1. In another embodiment, p is 2. In another embodiment, p is 3.

In one embodiment, n is 1, m is 1, and p is 1, 2 or 3. In another embodiment, p is 1. In another embodiment, p is 2. In another embodiment, p is 3.

In one embodiment, n is 1 or 2, and ring C is furanyl. In another embodiment, n is 0, 1 or 2, and ring C is other than furanyl.

Table 1 provides representative N-hydroxymethanesulfonamide compounds of the disclosure.

TABLE 1

N-Hydroxymethanesulfonamide Compounds of the Disclosure

| Compound No. | Structure | Name |
|---|---|---|
| 1 | 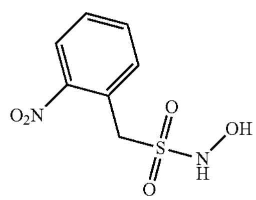 [SMILES: O=[N+]([O-])c1ccccc1CS(=O)(=O)NO] | N-Hydroxy-1-(2-nitrophenyl)methanesulfonamide |
| 2 | 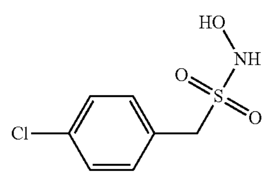 [SMILES: O=S(=O)(Cc1ccc(Cl)cc1)NO] | 1-(4-Chlorophenyl)-N-hydroxymethanesulfonamide |
| 3 | 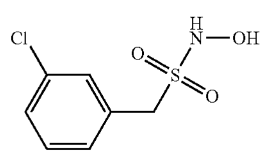 [SMILES: O=S(=O)(Cc1cccc(Cl)c1)NO] | 1-(3-Chlorophenyl)-N-hydroxymethanesulfonamide |
| 4 | 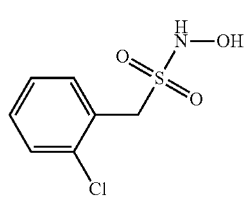 [SMILES: O=S(=O)(Cc1ccccc1Cl)NO] | 1-(2-Chlorophenyl)-N-hydroxymethanesulfonamide |
| 5 | 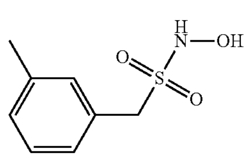 | N-Hydroxy-1-(3-methylphenyl)methanesulfonamide |

TABLE 1-continued

N-Hydroxymethanesulfonamide Compounds of the Disclosue

| Compound No. | Structure | Name |
|---|---|---|
| 6 | 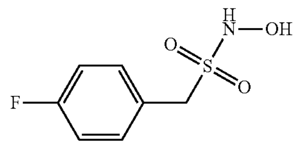 [SMILES: O=S(=O)(Cc1ccc(F)cc1)NO] | 1-(4-Fluorophenyl)-N-hydroxymethanesulfonamide |
| 7 | 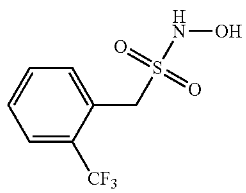 [SMILES: O=S(=O)(Cc1ccccc1C(F)(F)F)NO] | N-Hydroxy-1-[2-(trifluoromethyl)phenyl]methanesulfonamide |
| 8 | 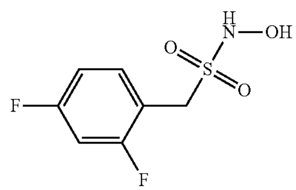 [SMILES: O=S(=O)(Cc1ccc(F)cc1F)NO] | 1-(2,4-Difluorophenyl)-N-hydroxymethanesulfonamide |
| 9 | 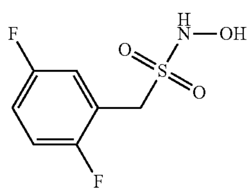 [SMILES: O=S(=O)(Cc1cc(F)ccc1F)NO] | 1-(2,5-Difluorophenyl)-N-hydroxymethanesulfonamide |
| 10 | 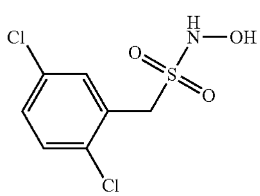 [SMILES: O=S(=O)(Cc1cc(Cl)ccc1Cl)NO] | 1-(2,5-Dichlorophenyl)-N-hydroxymethanesulfonamide |
| 11 | 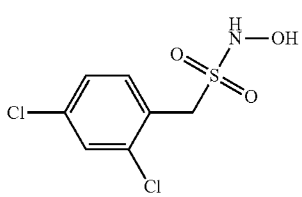 [SMILES: O=S(=O)(Cc1ccc(Cl)cc1Cl)NO] | 1-(2,4-Dichlorophenyl)-N-hydroxymethanesulfonamide |
| 12 | 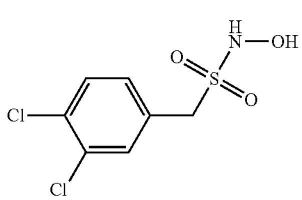 [SMILES: O=S(=O)(Cc1ccc(Cl)c(Cl)c1)NO] | 1-(3,4-Dichlorophenyl)-N-hydroxymethanesulfonamide |
| 13 | 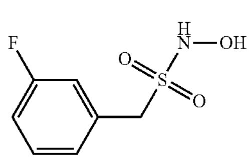 [SMILES: O=S(=O)(Cc1cccc(F)c1)NO] | 1-(3-Fluorophenyl)-N-hydroxymethanesulfonamide |

TABLE 1-continued

N-Hydroxymethanesulfonamide Compounds of the Disclosue

| Compound No. | Structure | Name |
|---|---|---|
| 14 | 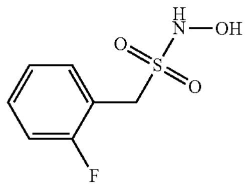 [SMILES: O=S(=O)(Cc1ccccc1F)NO] | 1-(2-Fluorophenyl)-N-hydroxymethanesulfonamide |
| 15 | 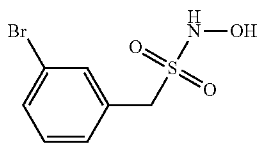 [SMILES: O=S(=O)(Cc1cccc(Br)c1)NO] | 1-(3-Bromophenyl)-N-hydroxymethanesulfonamide |
| 16 | 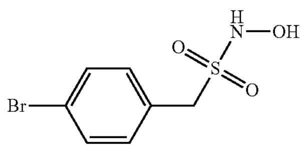 [SMILES: O=S(=O)(Cc1ccc(Br)cc1)NO] | 1-(4-Bromophenyl)-N-hydroxymethanesulfonamide |
| 17 | 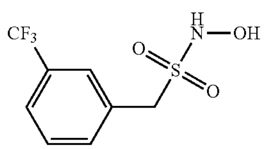 [SMILES: O=S(=O)(Cc1cccc(C(F)(F)F)c1)NO] | N-Hydroxy-1-[3-(trifluoromethyl)phenyl]methanesulfonamide |
| 18 | 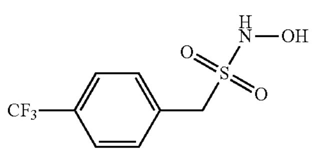 [SMILES: O=S(=O)(Cc1ccc(C(F)(F)F)cc1)NO] | N-Hydroxy-1-[4-(trifluoromethyl)phenyl]methanesulfonamide |
| 19 | 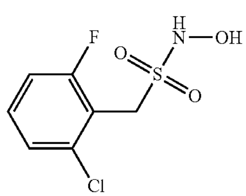 [SMILES: O=S(=O)(Cc1c(F)cccc1Cl)NO] | 1-(2-Chloro-6-fluorophenyl)-N-hydroxymethanesulfonamide |
| 20 | 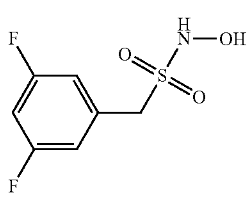 [SMILES: O=S(=O)(Cc1cc(F)cc(F)c1)NO] | 1-(3,5-Difluorophenyl)-N-hydroxymethanesulfonamide |
| 21 | 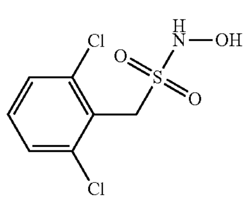 [SMILES: O=S(=O)(Cc1c(Cl)cccc1Cl)NO] | 1-(2,6-Dichlorophenyl)-N-hydroxymethanesulfonamide |

TABLE 1-continued

N-Hydroxymethanesulfonamide Compounds of the Disclosue

| Compound No. | Structure | Name |
| --- | --- | --- |
| 22 | 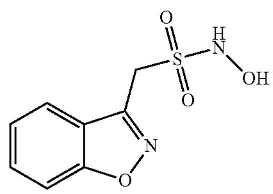 [SMILES: O=S(=O)(Cc1noc2ccccc12)NO] | 1-1,2-Benzoxazol-3-yl-N-hydroxymethanesulfonamide |
| 23 | 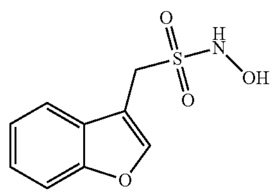 [SMILES: O=S(=O)(Cc1coc2ccccc12)NO] | 1-(Benzofuran-3-yl)-N-hydroxymethanesulfonamide |
| 24 | 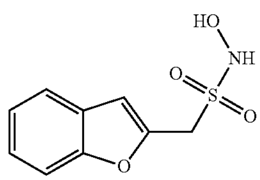 [SMILES: O=S(=O)(Cc1cc2ccccc2o1)NO] | 1-(Benzofuran-2-yl)-N-hydroxymethanesulfonaamide |
| 25 | 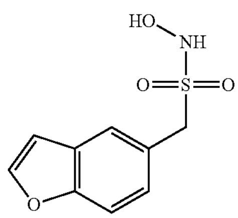 [SMILES: O=S(=O)(Cc1ccc2occc2c1)NO] | 1-(Benzofuran-5-yl)-N-hydroxymethanesulfonamide |
| 26 | 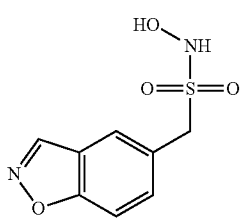 [SMILES: O=S(=O)(Cc1ccc2oncc2c1)NO] | 1-(Benzo[d]isoxazol-5-yl)-N-hydroxymethanesulfonamide |
| 27 | 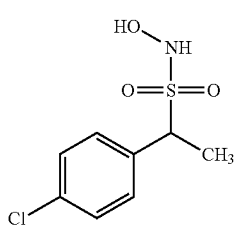 | 1-(4-Chlorophenyl)-N-hydroxyethanesulfonamide |
| 28 | 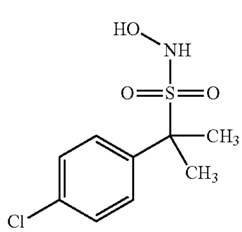 | 2-(4-Chlorophenyl)-N-hydroxypropane-2-sulfonamide |

TABLE 1-continued

N-Hydroxymethanesulfonamide Compounds of the Disclosure

| Compound No. | Structure | Name |
|---|---|---|
| 29 | 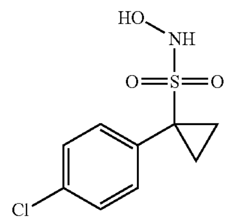 [SMILES: O=S(=O)(NO)C1(c2ccc(Cl)cc2)CC1] | 1-(4-Chlorophenyl)-N-hydroxycyclopropane-1-sulfonamide |
| 30 | 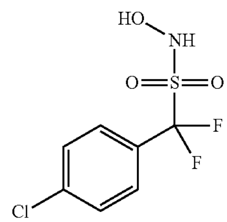 [SMILES: O=S(=O)(NO)C(F)(F)c1ccc(Cl)cc1] | 1-(4-Chlorophenyl)-1,1-difluoro-N-hydroxymethanesulfonamide |
| 31 | 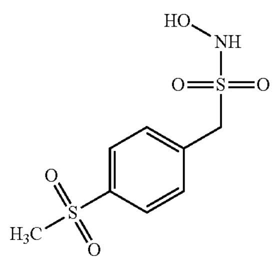 [SMILES: CS(=O)(=O)c1ccc(CS(=O)(=O)NO)cc1] | N-Hydroxy-1-(4-(methylsulfonyl)phenyl)methanesulfonamide |
| 32 | 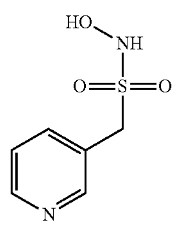 [SMILES: O=S(=O)(Cc1cccnc1)NO] | N-Hydroxy-1-(pyridin-3-yl)methanesulfonamide |
| 33 | 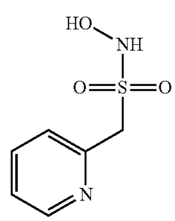 [SMILES: O=S(=O)(Cc1ccccn1)NO] | N-Hydroxy-1-(pyridin-2-yl)methanesulfonamide |
| 34 | 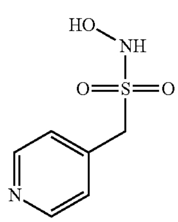 [SMILES: O=S(=O)(Cc1ccncc1)NO] | N-Hydroxy-1-(pyridin-4-yl)methanesulfonamide |
| 35 | 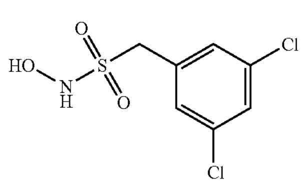 [SMILES: O=S(=O)(Cc1cc(Cl)cc(Cl)c1)NO] | 1-(3,5-Dichlorophenyl)-N-hydroxymethanesulfonamide |

TABLE 1-continued

N-Hydroxymethanesulfonamide Compounds of the Disclosure

| Compound No. | Structure | Name |
|---|---|---|
| 36 | 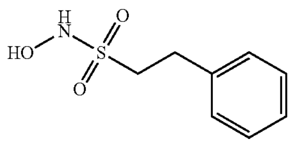 [SMILES: O=S(=O)(CCc1ccccc1)NO] | N-Hydroxy-2-phenylethane-1-sulfonamide |
| 37 | 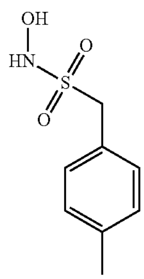 | N-Hydroxy-1-(4-methylphenyl)methanesulfonamide |
| 38 | 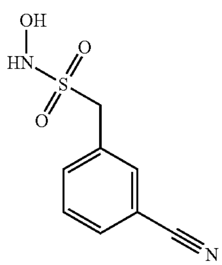 [SMILES: N#Cc1cccc(CS(=O)(=O)NO)c1] | 1-(3-Cyanophenyl)-N-hydroxymethanesulfonamide |
| 39 | 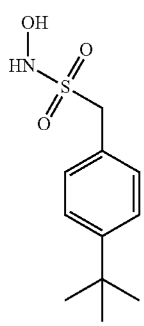 | 1-(4-tert-Butylphenyl)-N-hydroxymethanesulfonamide |
| 40 | 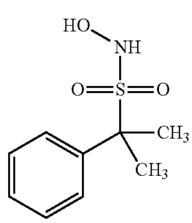 | N-Hydroxy-2-phenylpropane-2-sulfonamide |
| 41 | 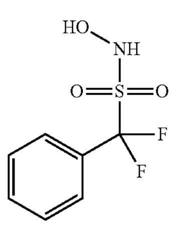 [SMILES: O=S(=O)(NO)C(F)(F)c1ccccc1] | 1,1-Difluoro-N-hydroxy-1-phenylmethanesulfonamide |

TABLE 1-continued

N-Hydroxymethanesulfonamide Compounds of the Disclosure

| Compound No. | Structure | Name |
|---|---|---|
| 42 | 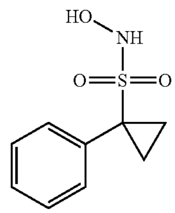 [SMILES: O=S(=O)(NO)C1(c2ccccc2)CC1] | N-Hydroxy-1-phenylcyclopropane-1-sulfonamide |
| 43 | 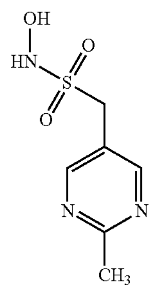 | N-Hydroxy-1-(2-methylpyrimidin-5-yl)methanesulfonamide |
| 44 | 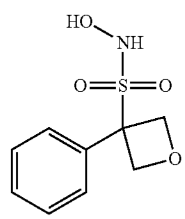 [SMILES: O=S(=O)(NO)C1(c2ccccc2)COC1] | N-Hydroxy-3-phenyloxetane-3-sulfonamide |
| 45 | 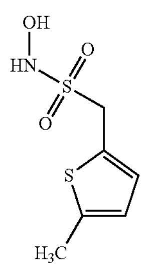 | N-Hydroxy-1-(5-methylthiophen-2-yl)methanesulfonamide |
| 46 | 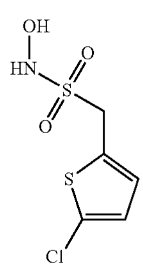 [SMILES: O=S(=O)(Cc1ccc(Cl)s1)NO] | 1-(5-Chlorothiophen-2-yl)-N-hydroxymethanesulfonamide |
| 47 | 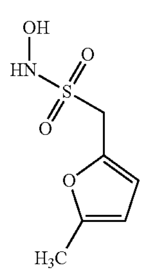 | N-Hydroxy-1-(5-methylfuran-2-yl)methanesulfonamide |

In particular embodiments, a N-hydroxymethanesulfonamide nitroxyl donating compound in Table 1 can be utilized as a pharmaceutically acceptable salt thereof.

Unexpectedly, it has been discovered that compounds falling within the scope of formulae (I), (II), (III) and (IV) (e.g., Compounds in Table 1) are sufficiently stable under solid state conditions and, thus, are amenable to oral administration. Moreover, particular compounds falling within the scope of formulae (I), (II), (III) and (IV) have a half-life of greater than about 10 minutes, e.g., when measured in dog human plasma in the presence of an anticoagulant (e.g., heparin or sodium citrate) at pH 7.4, in accordance with the procedure described in Example 24. It has been discovered that such compounds have a favorable toxiclogical profile.

Measuring Nitroxyl Donating Ability

Compounds are easily tested for nitroxyl donation by routine experiments. Although it is typically impractical to directly measure whether nitroxyl is donated, several analytical approaches are accepted as suitable for determining whether a compound donates nitroxyl. For example, the compound of interest can be placed in solution, for example in phosphate buffered saline (PBS) or in a phosphate buffered solution at a pH of about 7.4, in a sealed container. After sufficient time for disassociation has elapsed, such as from several minutes to several hours, the headspace gas is withdrawn and analyzed to determine its composition, such as by gas chromatography and/or mass spectrometry. If the gas $N_2O$ is formed (which occurs by HNO dimerization), the test is positive for nitroxyl donation and the compound is deemed to be a nitroxyl donor.

The level of nitroxyl donating ability can be expressed as a percentage of a compound's theoretical stoichiometric maximum. A compound that donates a "significant level of nitroxyl" means, in various embodiments, a compound that donates about 40% or more, about 50% or more, about 60% or more, about 70% or more, about 80% or more, about 90% or more, or about 95% or more of its theoretical maximum amount of nitroxyl. In particular embodiments, a N-hydroxymethanesulfonamide nitroxyl donor compound herein donates from about 70% to about 90% of its theoretical maximum amount of nitroxyl. In particular embodiments, a N-hydroxymethanesulfonamide nitroxyl donor donates from about 85% to about 95% of its theoretical maximum amount of nitroxyl. In particular embodiments, a N-hydroxymethanesulfonamide nitroxyl donor donates from about 90% to about 95% of its theoretical maximum amount of nitroxyl. N-hydroxymethanesulfonamide nitroxyl donor compounds that donate less than about 40%, or less than about 50%, of their theoretical maximum amount of nitroxyl are still nitroxyl donors and can be used in the methods disclosed. A N-hydroxymethanesulfonamide nitroxyl donor compound that donates less than about 50% of its theoretical amount of nitroxyl can be used in the methods disclosed, but may require higher dosing levels as compared to a compound that donates a higher level of nitroxyl.

If desired, nitroxyl donation also can be detected by exposing the test compound to metmyoglobin ($Mb^{3+}$). See Bazylinski et al., *J. Amer. Chem. Soc.* 107(26):7982-7986 (1985). Nitroxyl reacts with $Mb^{3+}$ to form a $Mb^{2+}$—NO complex, which can be detected by changes in the ultraviolet/visible spectrum or by electron paramagnetic resonance (EPR). The $Mb^{2+}$—NO complex has an EPR signal centered around a g-value of about 2. Nitric oxide, on the other hand, reacts with $Mb^{3+}$ to form an $Mb^{3+}$—NO complex that has a negligible, if any, EPR signal. Accordingly, if a compound reacts with Mb' to form a complex detectable by common methods, such as ultraviolet/visible or EPR, then the test is positive for nitroxyl donation.

Testing for nitroxyl donation can be performed at a physiologically relevant pH. The N-hydroxymethanesulfonamide nitroxyl donating compounds are capable of donating nitroxyl at physiological pH (i.e., a pH of about 7.4) and physiological temperature (i.e., a temperature of about 37° C.) (together, "physiological conditions"). In particular embodiments, a N-hydroxymethanesulfonamide nitroxyl donating compound can donate about 40% or more of its theoretical maximum (i.e., 100%) amount of nitroxyl under physiological conditions. In particular embodiments, a N-hydroxymethanesulfonamide nitroxyl donating compound can donate about 50% or more of its theoretical maximum amount of nitroxyl under physiological conditions. In particular embodiments, a N-hydroxymethanesulfonamide nitroxyl donating compound can donate about 60% or more of its theoretical maximum amount of nitroxyl under physiological conditions. In particular embodiments, a N-hydroxymethanesulfonamide nitroxyl donating compound can donate about 70% or more of its theoretical maximum amount of nitroxyl under physiological conditions. In particular embodiments, a N-hydroxymethanesulfonamide nitroxyl donating compound can donate about 80% or more of its theoretical maximum amount of nitroxyl under physiological conditions. In particular embodiments, a N-hydroxymethanesulfonamide nitroxyl donating compound can donate about 90% or more of its theoretical maximum amount of nitroxyl under physiological conditions.

It will be understood that a N-hydroxymethanesulfonamide nitroxyl donating compound might also donate a limited amount of nitric oxide, so long as the amount of nitroxyl donation exceeds the amount of nitric oxide donation. In certain embodiments, a N-hydroxymethanesulfonamide nitroxyl donating compound can donate about 25 mole % or less of nitric oxide under physiological conditions. In particular embodiments, a N-hydroxymethanesulfonamide nitroxyl donating compound can donate about 20 mole % or less of nitric oxide under physiological conditions. In particular embodiments, a N-hydroxymethanesulfonamide nitroxyl donating compound can donate about 15 mole % or less of nitric oxide under physiological conditions. In particular embodiments, a N-hydroxymethanesulfonamide nitroxyl donating compound can donate about 10 mole % or less of nitric oxide under physiological conditions. In particular embodiments, a N-hydroxymethanesulfonamide nitroxyl donating compound can donates about 5 mole % or less of nitric oxide under physiological conditions. In particular embodiments, a N-hydroxymethanesulfonamide nitroxyl donating compound can donate about 2 mole % or less of nitric oxide under physiological conditions. In particular embodiments, a N-hydroxymethanesulfonamide nitroxyl donating compound can donate an insignificant amount (e.g., about 1 mole % or less) of nitric oxide under physiological conditions.

Pharmaceutical Compositions

The disclosure also encompasses pharmaceutical compositions comprising a N-hydroxymethanesulfonamide nitroxyl donating compound of formulae (I), II), (III), or (IV) and at least one pharmaceutically acceptable excipient. Examples of pharmaceutically acceptable excipients include those described above, such as carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and any combination thereof. The selection and use of pharmaceutically acceptable excipients is taught, e.g., in Troy, Ed., *Remington: The Science and Practice of Pharmacy*, 21$^{st}$ Ed. (Lippincott Williams & Wilkins, Baltimore, Md., 2005).

In various embodiments, the at least one pharmaceutically acceptable excipient comprises at least one species of cyclodextrin. In a particular embodiment, the cyclodextrin is a cyclic structure having glucose units linked by α(1-4) linkages. In another embodiment, the cyclodextrin is a β-cyclodextrin, i.e., a cyclic structure having seven glucose units linked by α(1-4) linkages. In another embodiment, the cyclodextrin is chemically modified by derivatizing any combination of the three available hydroxyl groups on each glucopyranose unit thereof.

In some embodiments where the pharmaceutically acceptable excipient comprises at least one species of cyclodextrin, the cyclodextrin is a sulfo($C_1$-$C_6$)alkyl ether derivative of β-cyclodextrin. In certain of these embodiments, the cyclodextrin is a sulfo($C_1$-$C_6$)alkyl ether derivative of β-cyclodextrin having from about six to about seven sulfo($C_1$-$C_6$) alkyl ether groups per cyclodextrin molecule. In various embodiments, the cyclodextrin is a sulfo($C_1$-$C_6$)alkyl ether derivative of β-cyclodextrin having an average of from about six to about seven sulfo($C_1$-$C_6$)alkyl ether groups per cyclodextrin molecule. In another such embodiment, the cyclodextrin is a sulfo($C_1$-$C_6$)alkyl ether derivative of β-cyclodextrin having six or seven sulfo($C_1$-$C_6$)alkyl ether groups per cyclodextrin molecule.

In a particular series of embodiments where the pharmaceutically acceptable excipient comprises at least one species of cyclodextrin, the cyclodextrin is a sulfo($C_3$-$C_5$)alkyl ether derivative of β-cyclodextrin. In one such embodiment, the cyclodextrin is a sulfo($C_3$-$C_5$)alkyl ether derivative of β-cyclodextrin having from about six to about seven sulfo ($C_3$-$C_5$)alkyl ether groups per cyclodextrin molecule. In various such embodiments, the cyclodextrin is a sulfo($C_3$-$C_5$)alkyl ether derivative of β-cyclodextrin having an average of from about six to about seven sulfo($C_3$-$C_5$)alkyl ether groups per cyclodextrin molecule. In another such embodiment, the cyclodextrin is a sulfo($C_3$-$C_5$)alkyl ether derivative of β-cyclodextrin having six or seven sulfo($C_3$-$C_5$)alkyl ether groups per cyclodextrin molecule.

In particular embodiments where the pharmaceutically acceptable excipient comprises at least one species of cyclodextrin, the cyclodextrin is a sulfobutyl ether derivative of β-cyclodextrin. In certain of these embodiments, the cyclodextrin is a sulfobutyl ether derivative of β-cyclodextrin having from about six to about seven sulfobutyl ether groups per cyclodextrin molecule. In another such embodiment, the cyclodextrin is a sulfobutyl ether derivative of β-cyclodextrin having an average of from about six to about seven sulfobutyl ether groups per cyclodextrin molecule. In another such embodiment, the cyclodextrin is a sulfobutyl ether derivative of β-cyclodextrin having six or seven sulfobutyl ether groups per cyclodextrin molecule.

In certain embodiments where the pharmaceutically acceptable excipient comprises at least one species of cyclodextrin, the cyclodextrin is a sulfo-n-butyl ether derivative of β-cyclodextrin. In one such embodiment, the cyclodextrin is a sulfo-n-butyl ether derivative of β-cyclodextrin having from about six to about seven sulfo-n-butyl ether groups per cyclodextrin molecule. In another such embodiment, the cyclodextrin is a sulfo-n-butyl ether derivative of β-cyclodextrin having an average of from about six to about seven sulfo-n-butyl ether groups per cyclodextrin molecule. In another such embodiment, the cyclodextrin is a sulfo-n-butyl ether derivative of β-cyclodextrin having six or seven sulfo-n-butyl ether groups per cyclodextrin molecule.

In various particular embodiments where the pharmaceutically acceptable excipient comprises at least one species of cyclodextrin, the cyclodextrin comprises a plurality of negative charges at physiologically compatible pH values, e.g., at a pH of from about 5.0 to about 6.8 in some embodiments, from about 5.5 to about 6.5 in some embodiments, from about 5.7 to about 6.3 in some embodiments, from about 5.8 to about 6.2 in some embodiments, from about 5.9 to about 6.1 in some embodiments, and about 6.0 in particular embodiments. In one such embodiment, the at least one pharmaceutically acceptable excipient comprises CAPTISOL® cyclodextrin (Ligand Pharmaceuticals, La Jolla, Calif.).

The pharmaceutical compositions can be formulated for administration in solid or liquid form, including those adapted for the following: (1) oral administration, for example, as drenches (for example, aqueous or non-aqueous solutions or suspensions), tablets (for example, those targeted for buccal, sublingual and systemic absorption), caplets, boluses, powders, granules, pastes for application to the tongue, hard gelatin capsules, soft gelatin capsules, mouth sprays, troches, lozenges, pellets, syrups, suspensions, elixirs, liquids, emulsions and microemulsions; or (2) parenteral administration by, for example, subcutaneous, intramuscular, intravenous or epidural injection as, for example, a sterile solution or suspension. The pharmaceutical compositions can be for immediate, sustained or controlled release.

In one particular embodiment, the pharmaceutical composition is formulated for intravenous administration. In another embodiment, the pharmaceutical composition is formulated for intravenous administration by continuous infusion.

In another embodiment, the pharmaceutical composition is formulated for oral administration. Compounds for oral administration can be formulated as liquid or solid dosage forms. In particular embodiments where the N-hydroxymethanesulfonamide nitroxyl donating compounds are formulated as oral liquid dosage forms, polyethylene glycol 300 (PEG300) can usefully serve as an excipient.

The compounds and pharmaceutical compositions disclosed herein can be prepared as any appropriate unit dosage form, such as capsules, sachets, tablets, powder, granules, solution, suspension in an aqueous liquid, suspension in a non-aqueous liquid, oil-in-water liquid emulsion, water-in-oil liquid emulsion, liposomes or bolus.

Tablets can be made by compression or molding, optionally with one or more accessory ingredients. Compressed tablets can be prepared by compressing in a suitable machine the therapeutic agent or agents in a free-flowing form such as a powder or granules, optionally mixed with a binder, lubricant, inert diluent, preservative, surface-active or dispersing agent. Molded tablets can be made by molding in a suitable machine a mixture of the powdered compound moistened with an inert liquid diluent. The tablets can be optionally coated or scored and can be formulated so as to provide slow or controlled release of the active ingredient therein. Methods of formulating such slow or controlled release compositions of pharmaceutically active ingredients, such as the therapeutic agents herein and other compounds known in the art, are known in the art and disclosed in issued U.S. patents, some of which include, but are not limited to, U.S. Pat. Nos. 4,369,174, 4,842,866, and the references cited therein. Coatings can be used for delivery of compounds to the intestine (see, e.g., U.S. Pat. Nos. 6,638,534, 5,217,720, 6,569,457, and the references cited therein). An artisan will recognize that in addition to tablets, other dosage forms can be formulated to provide slow or controlled release of the active ingredient. Such dosage forms include, but are not limited to, capsules, granulations and gel-caps.

Pharmaceutical compositions suitable for topical administration include, without limitation, lozenges comprising the ingredients in a flavored basis, such as sucrose, *acacia* and tragacanth; and pastilles comprising the active ingredient in a flavored basis or in an inert basis, such as gelatin and glycerin.

Various embodiments of pharmaceutical compositions suitable for parenteral administration include, without limitation, either aqueous sterile injection solutions or non-aqueous sterile injection solutions, each containing, for example, anti-oxidants, buffers, bacteriostats and solutes that render the formulation isotonic with the blood of the intended recipient; and aqueous sterile suspensions and non-aqueous sterile suspensions, each containing, for example, suspending agents and thickening agents. The formulations can be presented in unit-dose or multi-dose containers, for example, sealed ampules or vials, and can be stored in a freeze dried (lyophilized) condition requiring only the addition of a sterile liquid carrier, such as water, immediately prior to use.

Pharmaceutical compositions administered parenterally can be administered in an acidic, neutral or basic solution. In one embodiment, pharmaceutical compositions comprising a N-hydroxymethanesulfonamide nitroxyl donating compound can be formulated in an acidic solution having a pH of from about 4 to about 5, for instance, a pH of about 4, about 4.5, about 4.8, or about 5, including values there between. While a pH of about 4 has generally been considered optimal for formulating nitroxyl donating compositions to achieve adequate stability of the compound, it has been discovered that formulating under such acidic conditions can potentially cause or exacerbate venous irritation following parenteral administration. The amount of irritation can be attenuated by formulating the N-hydroxymethanesulfonamide nitroxyl donating compound in less acidic or even neutral solutions (see FIG. 4). Accordingly, in particular embodiments, a N-hydroxymethanesulfonamide nitroxyl donating compound can be formulated for parenteral use at a pH of from about 5 to about 6.2 (e.g., pH of about 5, about 5.5, about 5.8, about 6, or about 6,2, including values there between).

Methods of Using the Compounds and Pharmaceutical Compositions of the Disclosure In one aspect, the disclosure provides a method of increasing in vivo nitroxyl levels, comprising administering to a patient in need thereof an effective amount of a compound or a pharmaceutical composition as disclosed herein. In various embodiments, the patient has, is suspected of having, or is at risk of having or developing a condition that is responsive to nitroxyl therapy.

In particular embodiments, the disclosure provides a method of treating, preventing or delaying the onset and/or development of a condition, comprising administering to a patient (including a patient identified as in need of such treatment, prevention or delay) an effective amount of a compound or a pharmaceutical composition as disclosed herein. Identifying a patient in need thereof can be in the judgment of a physician, clinical staff, emergency response personnel or other health care professional and can be subjective (e.g., opinion) or objective (e.g., measurable by a test or diagnostic method).

Particular conditions embraced by the methods disclosed herein include, without limitation, cardiovascular diseases, ischemia/reperfusion injury, and pulmonary hypertension (PH).

Cardiovascular Diseases

In one embodiment, the disclosure provides a method of treating a cardiovascular disease, comprising administering an effective amount of a compound or a pharmaceutical composition as disclosed herein to a patient in need thereof.

Examples of cardiovascular diseases and symptoms that can usefully be treated with the N-hydroxymethanesulfonamide nitroxyl donating compounds and compositions disclosed herein include cardiovascular diseases that are responsive to nitroxyl therapy, coronary obstructions, coronary artery disease (CAD), angina, heart attack, myocardial infarction, high blood pressure, ischemic cardiomyopathy and infarction, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, diastolic heart failure, systolic heart failure, congestive heart failure, acute congestive heart failure, acute decompensated heart failure, and cardiac hypertrophy.

Heart Failure

The N-hydroxymethanesulfonamide nitroxyl donating compounds and compositions of the disclosure can be used to treat patients suffering from heart failure. The heart failure can be of any type or form, including any of the heart failures disclosed herein. Nonlimiting examples of heart failure include early stage heart failure, Class I, II, III and IV heart failure, acute heart failure, congestive heart failure (CHF) and acute congestive heart failure. In one embodiment, the N-hydroxymethanesulfonamide nitroxyl donating compounds and compositions of the disclosure can be used to treat acute decompensated heart failure.

In embodiments where the N-hydroxymethanesulfonamide nitroxyl donating compounds and compositions of the disclosure are used to treat patients suffering from heart failure, another active agent that treats heart failure can also be administered. In one such embodiment, the nitroxyl donor can be administered in conjunction with a positive inotrope such as a beta-agonist. Examples of beta-agonists include, without limitation, dopamine, dobutamine, isoproterenol, analogs of such compounds and derivatives of such compounds. In another embodiment, nitroxyl donor can be administered in conjunction with a beta-adrenergic receptor antagonist (also referred to herein as beta-antagonist or beta-blocker). Examples of beta-antagonists include, without limitation, propranolol, metoprolol, bisoprolol, bucindolol, and carvedilol.

N-hydroxymethanesulfonamide nitroxyl donating compounds can be administered as pharmaceutical formulations to patients in need of modulating in vivo nitroxyl levels. For instance, pharmaceutical formulations comprising N-hydroxymethanesulfonamide nitroxyl donating compounds can be administered to a patient intravenously. As described in Examples 26 and 27, heart failure models can be used to evaluate the hemodynamic profiles of the N-hydroxymethanesulfonamide nitroxyl donating compounds.

Ischemia/Reperfusion Injury

In another embodiment, the disclosed subject matter provides a method of treating, preventing or delaying the onset and/or development of ischemia/reperfusion injury, comprising administering an effective amount of a compound or pharmaceutical composition as disclosed herein to a subject in need thereof.

In a particular embodiment, the method is for preventing ischemia/reperfusion injury. In a particular embodiment, a compound or pharmaceutical composition of the disclosure is administered prior to the onset of ischemia. In a particular embodiment, a pharmaceutical composition of the disclosure is administered prior to procedures in which myocardial ischemia can occur, for example an angioplasty or surgery, such as a coronary artery bypass graft surgery. In a particular embodiment, a pharmaceutical composition of the disclosure is administered after ischemia but before reperfusion. In a particular embodiment, a pharmaceutical composition of the disclosure is administered after ischemia and reperfusion.

In another embodiment, a pharmaceutical composition of the disclosure can be administered to a patient who is at risk for an ischemic event. In a particular embodiment, a pharmaceutical composition of the disclosure is administered to a patient at risk for a future ischemic event, but who has no present evidence of ischemia. The determination of whether a patient is at risk for an ischemic event can be performed by any method known in the art, such as by examining the patient or the patient's medical history. In a particular embodiment, the patient has had a prior ischemic event. Thus, the patient can be at risk of a first or subsequent ischemic event. Examples of patients at risk for an ischemic event include patients with known hypercholesterolemia, EKG changes associated with ischemia (e.g., peaked or inverted T-waves or ST segment elevations or depression in an appropriate clinical context), abnormal EKG not associated with active ischemia, elevated CKMB, clinical evidence of ischemia (e.g., crushing sub-sternal chest pain or arm pain, shortness of breath and/or diaphoresis), prior history of myocardial infarction, elevated serum cholesterol, sedentary lifestyle, angiographic evidence of partial coronary artery obstruction, echocardiographic evidence of myocardial damage, or any other evidence of a risk for a future ischemic event. Examples of ischemic events include, without limitation, myocardial infarction (MI) and neurovascular ischemia, such as a cerebrovascular accident (CVA).

In another embodiment, the subject of treatment is an organ that is to be transplanted. In a particular embodiment, a pharmaceutical composition of the disclosure can be administered prior to reperfusion of the organ in a transplant recipient. In a particular embodiment, a pharmaceutical composition of the disclosure can be administered prior to removal of the organ from the donor, for example through the perfusion cannulas used in the organ removal process. If the organ donor is a live donor, for example a kidney donor, the compounds or pharmaceutical compositions of the disclosure can be administered to the organ donor. In a particular embodiment, the compounds or pharmaceutical compositions of the disclosure are administered by storing the organ in a solution comprising the compound or pharmaceutical composition. For example, a compound or pharmaceutical composition of the disclosure can be included in the organ preservation solution, such as the University of Wisconsin "UW" solution, which is a solution comprising hydroxyethyl starch substantially free of ethylene glycol, ethylene chlorohydrin and acetone (see U.S. Pat. No. 4,798,824). In a particular embodiment, a pharmaceutical composition of the disclosure that is administered is such that ischemia/reperfusion injury to the tissues of the organ is reduced upon reperfusion in the recipient of transplanted organ. In a particular embodiment, the method reduces tissue necrosis (the size of infarct) in at-risk tissues.

Ischemia/reperfusion injury can damage tissues other than those of the myocardium and the disclosed subject matter embraces methods of treating or preventing such damage. In various embodiments, the ischemia/reperfusion injury is non-myocardial. In particular embodiments, the method reduces injury from ischemia/reperfusion in the tissue of the brain, liver, gut, kidney, bowel, or any part of the body other than the myocardium. In another embodiment, the patient is at risk for such injury. Selecting a person at risk for non-myocardial ischemia could include a determination of the indicators used to assess risk for myocardial ischemia. However, other factors can indicate a risk for ischemia/reperfusion in other tissues. For example, surgery patients often experience surgery related ischemia. Thus, patients scheduled for surgery could be considered at risk for an ischemic event. The following risk factors for stroke (or a subset of these risk factors) could demonstrate a patient's risk for ischemia of brain tissue: hypertension, cigarette smoking, carotid artery stenosis, physical inactivity, diabetes mellitus, hyperlipidemia, transient ischemic attack, atrial fibrillation, coronary artery disease, congestive heart failure, past myocardial infarction, left ventricular dysfunction with mural thrombus, and mitral stenosis. Ingall, *Postgrad. Med.* 107(6):34-50 (2000). Further, complications of untreated infectious diarrhea in the elderly can include myocardial, renal, cerebrovascular and intestinal ischemia. Slotwiner-Nie et al., *Gastroenterol. Clin. N. Amer.* 30(3):625-635 (2001). Alternatively, patients could be selected based on risk factors for ischemic bowel, kidney and/or liver disease. For example, treatment would be initiated in elderly patients at risk of hypotensive episodes (such as surgical blood loss). Thus, patients presenting with such an indication would be considered at risk for an ischemic event. In another embodiment, the patient has any one or more of the conditions listed herein, such as diabetes mellitus and hypertension. Other conditions that can result in ischemia, such as cerebral arteriovenous malformation, could demonstrate a patient's risk for an ischemic event.

Pulmonary Hypertension

In another embodiment, a compounds or pharmaceutical composition of the disclosure can be used to prevent or delay the onset and/or development of pulmonary hypertension. In one such embodiment, a compounds or pharmaceutical composition of the disclosure can be used to prevent or delay the onset and/or development of pulmonary arterial hypertension (PAH).

In another embodiment, the disclosed subject matter provides a method of reducing mean pulmonary arterial pressure (MPAP), comprising administering an effective amount of a compound or a pharmaceutical composition disclosed herein to a patient in need thereof. In another embodiment, the MPAP is reduced by up to about 50%. In another embodiment, the MPAP is reduced by up to about 25%. In another embodiment, the MPAP is reduced by up to about 20%. In another embodiment, the MPAP is reduced by up to about 15%. In another embodiment, the MPAP is reduced by up to 10%. In another embodiment, the MPAP is reduced by up to about 5%. In another embodiment, the MPAP is reduced to be from about 12 mmHg to about 16 mmHg. In another embodiment, the MPAP is reduced to be about 15 mmHg.

Administration Modes, Regimens and Dose Levels

The compounds and pharmaceutical compositions of the disclosure can be administered via parenteral (e.g., subcutaneous, intramuscular, intravenous or intradermal) administration. In certain embodiments, the compound or pharmaceutical composition is administered by intravenous infusion. In other embodiments, the compounds and pharmaceutical compositions of the disclosure can be administered by oral administration.

When a pharmaceutical composition comprising a compound of the present disclosure is administered, dosages are expressed based on the amount of active pharmaceutical ingredient, i.e., the amount of nitroxyl donor compound(s) of the disclosure present in the pharmaceutical composition.

In a variety of embodiments, including various oral administration embodiments, the compounds or pharmaceutical compositions of the disclosure are administered according to a weight-based daily dosing regimen, either as a single daily dose (QD) or in multiple divided doses administered, e.g., twice a day (BID), three times a day (TID), or four times a day (QID).

In certain embodiments, the N-hydroxymethanesulfonamide nitroxyl donating compound or pharmaceutical composition of the disclosure is administered in a dose of at least about 0.5 mg/kg/d, at least about 0.75 mg/kg/d, at least about 1.0 mg/kg/d, at least about 1.5 mg/kg/d, at least about 2 mg/kg/d, at least about 2.5 mg/kg/d, at least about 3 mg/kg/d, at least about 4 mg/kg/d, at least about 5 mg/kg/d, at least about 7.5 mg/kg/d, at least about 10 mg/kg/d, at least about 12.5 mg/kg/d, at least about 15 mg/kg/d, at least about 17.5 mg/kg/d, at least about 20 mg/kg/d, at least about 25 mg/kg/d, at least about 30 mg/kg/d, at least about 35 mg/kg/d, at least about 40 mg/kg/d, at least about 45 mg/kg/d, at least about 50 mg/kg/d, at least about 60 mg/kg/d, at least about 70 mg/kg/d, at least about 80 mg/kg/d, at least about 90 mg/kg/d, or at least about 100 mg/kg/d.

In certain embodiments, the N-hydroxymethanesulfonamide nitroxyl donating compound or pharmaceutical composition of the disclosure is administered at a dose of no more than about 100 mg/kg/d, no more than about 100 mg/kg/d, no more than about 90 mg/kg/d, no more than about 80 mg/kg/d, no more than about 80 mg/kg/d, no more than about 75 mg/kg/d, no more than about 70 mg/kg/d, no more than about 60 mg/kg/d, no more than about 50 mg/kg/d, no more than about 45 mg/kg/d, no more than about 40 mg/kg/d, no more than about 35 mg/kg/d, no more than about 30 mg/kg/d.

In a variety of embodiments, the dose is from about 0.001 mg/kg/d to about 10,000 mg/kg/d. In certain embodiments, the dose is from about 0.01 mg/kg/d to about 1,000 mg/kg/d. In certain embodiments, the dose is from about 0.01 mg/kg/d to about 100 mg/kg/d. In certain embodiments, the dose is from about 0.01 mg/kg/d to about 10 mg/kg/d. In certain embodiments, the dose is from about 0.1 mg/kg/d to about 1 mg/kg/d. In certain embodiments, the dose is less than about 1 g/kg/d.

In certain embodiments, a compound or pharmaceutical composition of the disclosure is administered in a dose range in which the low end of the range is any amount from about 0.1 mg/kg/day to about 90 mg/kg/day and the high end of the range is any amount from about 1 mg/kg/day to about 100 mg/kg/day (e.g., from about 0.5 mg/kg/day to about 2 mg/kg/day in one series of embodiments and from about 5 mg/kg/day to about 20 mg/kg/day in another series of embodiment).

In particular embodiments, the compound or pharmaceutical composition of the disclosure is administered in a dose range of about 3 to about 30 mg/kg, administered from once a day (QD) to three times a day (TID).

In certain embodiments, compounds or pharmaceutical compositions of the disclosure are administered according to a flat (i.e., non-weight-based) dosing regimen, either as a single daily dose (QD) or in multiple divided doses administered, e.g., twice a day (BID), three times a day (TID), or four times a day (QID).

In various embodiments, the compound or pharmaceutical composition of the disclosure is administered at a dose of at least about 0.01 grams/day (g/d), at least about 0.05 g/d, at least about 0.1 g/d, at least about 0.5 g/d, at least about 1 g/d, at least about 1.5 g/d, at least about 2.0 g/d, at least about 2.5 g/d, at least about 3.0 g/d, or at least about 3.5 g/d.

In various embodiments, the compound or pharmaceutical composition of the disclosure is administered at a dose of no more than about 5 g/d, no more than about 4.5 g/d, no more than about 4 g/d, no more than about 3.5 g/d, no more than about 3 g/d, no more than about 2.5 g/d, or no more than about 2 g/d.

In certain embodiments, the compound or pharmaceutical composition of the disclosure is administered in a dose of about 0.01 grams per day to about 4.0 grams per day. In certain embodiments, a compound or pharmaceutical composition of the disclosure can be administered at a dose in which the low end of the range is any amount from about 0.1 mg/day to about 400 mg/day and the high end of the range is any amount from about 1 mg/day to about 4000 mg/day. In certain embodiments, the compound or pharmaceutical composition is administered in a dose of about 5 mg/day to about 100 mg/day. In various embodiments, the compound or pharmaceutical composition is administered at a dose of from about 150 mg/day to about 500 mg/day.

The dosing interval for parenteral or oral administration can be adjusted according to the needs of the patient. For longer intervals between administrations, extended release or depot formulations can be used.

For intravenous administration, the dose can usefully be expressed per unit time, either as a fixed amount per unit time or as a weight-based amount per unit time.

In various embodiments, a compound or pharmaceutical composition of the disclosure is administered intravenously in an amount of at least about 0.1 µg/kg/min, at least about 0.2 µg/kg/min, at least about 0.3 µg/kg/min, at least about 0.4 µg/kg/min, at least about 0.5 µg/kg/min, at least about 1 µg/kg/min, at least about 2.5 µg/kg/min, at least about 5 µg/kg/min, at least about 7.5 µg/kg/min, at least about 10 µg/kg/min, at least about 11 µg/kg/min, at least about 12 µg/kg/min, at least about 13 µg/kg/min, at least about 14 µg/kg/min, at least about 15 µg/kg/min, at least about 16 µg/kg/min, at least about 17 µg/kg/min, at least about 18 µg/kg/min, at least about 19 µg/kg/min, at least about 20 µg/kg/min, at least about 21 µg/kg/min, at least about 22 µg/kg/min, at least about 23 µg/kg/min, at least about 24 µg/kg/min, at least about 25 µg/kg/min, at least about 26 µg/kg/min, at least about 27 µg/kg/min, at least about 28 µg/kg/min, at least about 29 µg/kg/min, at least about 30 µg/kg/min, at least about 31 µg/kg/min, at least about 32 µg/kg/min, at least about 33 µg/kg/min, at least about 34 µg/kg/min, at least about 35 µg/kg/min, at least about 36 µg/kg/min, at least about 37 µg/kg/min, at least about 38 µg/kg/min, at least about 39 µg/kg/min, or at least about 40 µg/kg/min.

In various embodiments, the compound or pharmaceutical composition of the present disclosure is administered intravenously in an amount of no more than about 100 µg/kg/min, no more than about 90 µg/kg/min, no more than about 80 µg/kg/min, no more than about 70 µg/kg/min, no more than about 60 µg/kg/min, no more than about 50 µg/kg/min, no more than about 49 µg/kg/min, no more than about 48 µg/kg/min, no more than about 47 µg/kg/min, no more than about 46 µg/kg/min, no more than about 45 µg/kg/min, no more than about 44 µg/kg/min, no more than about 43 µg/kg/min, no more than about 42 µg/kg/min, no more than about 41 µg/kg/min, no more than about 40 µg/kg/min, no more than about 39 µg/kg/min, no more than about 38 µg/kg/min, no more than about 37 µg/kg/min, no more than about 36 µg/kg/min, no more than about 35 µg/kg/min, no more than about 34 µg/kg/min, no more than about 33 µg/kg/min, no more than about 32 µg/kg/min, no more than about 31 µg/kg/min, or no more than about 30 µg/kg/min In some embodiments, the compound or pharmaceutical composition of the present disclosure is administered intravenously in an amount ranging from about 0.1 µg/kg/min to about 100 µg/kg/min, about 1 µg/kg/min to about 100 µg/kg/min, about 2.5 µg/kg/min to about 100 µg/kg/min, about 5 µg/kg/min to about 100 µg/kg/min, about 10 µg/kg/min to about 100 µg/kg/min, about 1.0 µg/kg/min to about 80 µg/kg/min, from about 10.0 µg/kg/min to about 70 µg/kg/min, from about 20 µg/kg/min to about 60 µg/kg/min, from about 15 µg/kg/min to about 50 µg/kg/min, from about 0.01 µg/kg/min to about 1.0 µg/kg/min, from about 0.01 µg/kg/min to about 10 µg/kg/min, from about 0.1 µg/kg/min to about 1.0 µg/kg/min, from about 0.1 µg/kg/min to about 10 µg/kg/min, from about 1.0 µg/kg/min to about 5 µg/kg/min, from about 70 µg/kg/min to about 100 µg/kg/min, or from about 80 µg/kg/min to about 90 µg/kg/min.

In particular embodiments, the compound or pharmaceutical composition of the present disclosure is administered intravenously in an amount ranging from about 10 µg/kg/min to about 50 µg/kg/min, about 20 µg/kg/min to about 40 µg/kg/min, about 25 µg/kg/min to about 35 µg/kg/min, or about 30 µg/kg/min to about 40 µg/kg/min. In particular embodiments, a compound or pharmaceutical composition of the present disclosure is administered intravenously in an amount of from about 20 µg/kg/min to about 30 µg/kg/min.

A compound or pharmaceutical composition as disclosed herein can be administered prior to, at substantially the same time with, or after administration of an additional therapeutic agent. The administration regimen can include pretreatment and/or co-administration with the additional therapeutic agent. In such case, the compound or pharmaceutical composition and the additional therapeutic agent can be administered simultaneously, separately, or sequentially.

Examples of administration regimens include without limitation: administration of each compound, pharmaceutical composition or therapeutic agent in a sequential manner; and co-administration of each compound, pharmaceutical composition or therapeutic agent in a substantially simultaneous manner (e.g., as in a single unit dosage form) or in multiple, separate unit dosage forms for each compound, pharmaceutical composition or therapeutic agent.

It will be appreciated by those in the art that the "effective amount" or "dose" ("dose level") will depend on various factors such as the particular administration mode, administration regimen, compound, and pharmaceutical composition selected, as well as the particular condition and patient being treated. For example, the appropriate dose level can vary depending upon the activity, rate of excretion and potential for toxicity of the specific compound or pharmaceutical composition employed; the age, body weight, general health, gender and diet of the patient being treated; the frequency of administration; the other therapeutic agent(s) being co-administered; and the type and severity of the condition.

Kits Comprising the Compounds or Pharmaceutical Compositions

The disclosure provides kits comprising a compound or a pharmaceutical composition disclosed herein. In a particular embodiment, the kit comprises a compound or a pharmaceutical composition disclosed herein, each in dry form, and a pharmaceutically acceptable liquid diluent.

In particular embodiments, either a compound in dry form or a pharmaceutical composition in dry form contains about 2.0% or less water by weight, about 1.5% or less water by weight, about 1.0% or less water by weight, about 0.5% or less water by weight, about 0.3% or less water by weight, about 0.2% or less water by weight, about 0.1% or less water by weight, about 0.05% or less water by weight, about 0.03% or less water by weight, or about 0.01% or less water by weight.

Pharmaceutically acceptable liquid diluents are known in the art and include but are not limited to sterile water, saline solutions, aqueous dextrose, glycerol, glycerol solutions, and the like. Other examples of suitable liquid diluents are disclosed by Nairn, "Solutions, Emulsions, Suspensions and Extracts," pp. 721-752 in *Remington: The Science and Practice of Pharmacy*, 20th Ed. (Lippincott Williams & Wilkins, Baltimore, Md., 2000).

In one embodiment, the kit further comprises instructions for using the compound or pharmaceutical composition. The instructions can be in any appropriate form, such as written or electronic form. In another embodiment, the instructions can be written instructions. In another embodiment, the instructions are contained in an electronic storage medium (e.g., magnetic diskette or optical disk). In another embodiment, the instructions include information as to the compound or pharmaceutical composition and the manner of administering the compound or pharmaceutical composition to a patient. In another embodiment, the instructions relate to a method of use disclosed herein (e.g., treating, preventing and/or delaying onset and/or development of a condition selected from cardiovascular diseases, ischemia/reperfusion injury, pulmonary hypertension and other conditions responsive to nitroxyl therapy).

In another embodiment, the kit further comprises suitable packaging. Where the kit comprises more than one compound or pharmaceutical composition, the compounds or pharmaceutical compositions can be packaged patiently in separate containers, or combined in one container when cross-reactivity and shelf life permit.

Should there be doubt over the agreement of a depicted chemical structure and a chemical name, the depicted chemical structure governs.

EXAMPLES

The following examples are presented for illustrative purposes and should not serve to limit the scope of the disclosed subject matter.

Synthesis of Compounds

The compounds disclosed herein can be made according to the methods disclosed below or by procedures known in the art. Starting materials for the reactions can be commercially available or can be prepared by known procedures or obvious modifications thereof. For example, some of the starting materials are available from commercial suppliers such as Sigma-Aldrich (St. Louis, Mo.). Others can be prepared by procedures or obvious modifications thereof disclosed in standard reference texts such as *March's Advanced Organic Chemistry* (John Wiley and Sons) and *Larock's Comprehensive Organic Transformations* (VCH Publishers).

Example 1

Preparation of N-Hydroxy-1-(2-nitrophenyl)methanesulfonamide (1)

To a solution of aqueous hydroxylamine (0.7 mL of a 50% solution, 10.61 mmol) in tetrahydrofuran (6 mL) and water (1 mL) cooled to −5° C. was slowly added (2-nitrophenyl)methanesulfonyl chloride (1.0 g, 4.2 mmol) maintaining a reaction temperature of less than 10° C. The reaction was maintained at this temperature until complete consumption of the sulfonyl chloride was observed by LC-MS (about 5 min.), after which time the reaction was diluted with dichloromethane (20 mL) and the organic portion was separated, washed with water (2×5 mL), dried over sodium sulfate, filtered and concentrated under reduced pressure to provide the N-hydroxysulfonamide as an off white solid, further washing with saturated sodium bicarbonate solution (10 mL) was required to remove sulfinic acid impurities. Trituration was carried out using heptanes:DCM (9:1 v:v) to provide the title compound as an off white solid (0.31 g, 31.9% yield). LC-MS $t_R$=1.38 min, [M−H]$^-$=231; $^1$H NMR (500 MHz, DMSO-d$_6$) δ ppm 9.77 (s, 1H), 9.44 (s, 1H), 8.05 (dd, J=8.1, 1.1 Hz, 1H), 7.77 (td, J=7.6, 1.2 Hz, 1H), 7.66 (td, J=8.0, 1.4 Hz, 1H), 7.62 (dd, J=7.7, 1.2 Hz, 1H), 4.92 (s, 2H).

Examples 2-21, 23 and 25-29

Preparation of Compounds 2 to 21, 23 and 25 to 29

The following compounds were synthesised according to the general method detailed below.

To a solution of aqueous hydroxylamine (2.5 equivalents of a 50% solution) in tetrahydrofuran (6 vol) and water (1 vol mL) cooled to −5° C. was slowly added the representative benzylic sulfonyl chloride (1 equivalent), maintaining a reaction temperature of less than 10° C. The reaction was maintained at this temperature until substantially complete consumption of the sulfonyl chloride was observed by TLC (about 5 min.), after which time the reaction was diluted with dichloromethane (30 vol) and the organic portion was separated, washed with water (2×5 vol), and ammonium chloride (10 vol), dried over sodium sulfate, filtered and concentrated under reduced pressure to provide the N-hydroxysulfonamide as a white solid. Trituration was carried out using heptane to provide the title compound.

Example 2

1-(4-Chlorophenyl)-N-hydroxymethanesulfonamide (2)

Synthesis was carried out from (4-chlorophenyl)methanesulfonyl chloride according to the general method. (0.735 g, 75% yield). LC-MS $t_R$=1.66 min, [M−H]$^-$=220; $^1$H NMR (500 MHz, DMSO-d$_6$) δ 14.46 (d, J=3.1 Hz, 1H), 13.99 (d, J=3.1 Hz, 1H), 12.25-12.13 (m, 4H), 9.20 (s, 2H).

Example 3

1-(3-Chlorophenyl)-N-hydroxymethanesulfonamide (3)

Synthesis was carried out from (3-chlorophenyl)methanesulfonyl chloride according to the general method. (0.76 g, 69% yield). LC-MS $t_R$=1.55 min, [M−H]$^-$=220; $^1$H NMR (250 MHz, DMSO-d$_6$) δ 9.70 (s, 1H), 9.27 (s, 1H), 7.48-7.29 (m, 4H), 4.46 (s, 2H).

Example 4

1-(2-Chlorophenyl)-N-hydroxymethanesulfonamide (4)

Synthesis was carried out from (2-chlorophenyl)methanesulfonyl chloride according to the general method. (1.14 g, 67% yield). LC-MS $t_R$=1.48 min, [M−H]$^-$=220; $^1$H NMR (250 MHz, DMSO-d$_6$) δ 9.74 (s, 1H), 9.37 (s, 1H), 7.58-7.32 (m, 4H), 4.59 (s, 2H).

Example 5

N-Hydroxy-1-(3-methylphenyl)methanesulfonamide (5)

Synthesis was carried out from (3-methylphenyl)methanesulfonyl chloride according to the general method. (0.53 g, 58% yield). LC-MS $t_R$=1.04 min, [M−H]$^-$=200; $^1$H NMR (250 MHz, DMSO-d$_6$) δ 9.66 (d, J=3.3 Hz, 1H), 9.18 (d, J=3.3 Hz, 1H), 7.31-7.23 (m, 1H), 7.18 (s, 3H), 4.35 (s, 2H), 2.31 (s, 3H).

Example 6

1-(4-Fluorophenyl)-N-hydroxymethanesulfonamide (6)

Synthesis was carried out from (4-fluorophenyl)methanesulfonyl chloride according to the general method. (0.17 g, 35% yield). LC-MS $t_R$=0.94 min, [M−H]$^-$=204; $^1$H NMR (250 MHz, Chloroform-d) δ 7.43 (t, 2H), 7.12 (t, J=8.6 Hz, 2H), 6.57 (s, 1H), 6.33 (s, 1H), 4.46 (s, 2H).

A second batch of material was obtained by concentrating the filtrate, then re-dissolved in dichloromethane and filtered to give a second crop of 1-(4-fluorophenyl)-N-hydroxymethanesulfonamide (0.15 g, 31.8% yield). $^1$H NMR (250 MHz, chloroform-d) δ 7.44 (dd, J=8.7, 5.2 Hz, 2H), 7.12 (t, J=8.6 Hz, 2H), 6.58 (s, 1H), 6.39 (s, 1H), 4.46 (s, 2H).

Example 7

N-Hydroxy-1-[2-(trifluoromethyl)phenyl]methanesulfonamide (7)

Synthesis was carried out from [2-(trifluoromethyl)phenyl]methanesulfonyl chloride according to the general method. (0.59 g, 62% yield). LC-MS $t_R$=1.1 min, [M−H]$^-$=254; $^1$H NMR (250 MHz, Chloroform-d) δ 9.82 (d, J=3.2 Hz, 1H), 9.45 (d, J=3.2 Hz, 1H), 7.83-7.55 (m, 4H), 4.60 (s, 2H).

Example 8

1-(2,4-Difluorophenyl)-N-hydroxymethanesulfonamide (8)

Synthesis was carried out from (2,4-difluorophenyl)methanesulfonyl chloride according to the general method. (0.57 g, 59% yield). LC-MS $t_R$=0.95 min, [M−H]$^-$=222; $^1$H NMR (250 MHz, DMSO-d$_6$) δ 9.71 (d, J=3.3 Hz, 1H), 9.35 (d, J=3.3 Hz, 1H), 7.57-7.42 (m, 1H), 7.30 (td, J=9.8, 2.6 Hz, 1H), 7.14 (td, J=8.6, 1.8 Hz, 1H), 4.44 (s, 2H).

Example 9

1-(2,5-Difluorophenyl)-N-hydroxymethanesulfonamide (9)

Synthesis was carried out from (2,5-difluorophenyl)methanesulfonyl chloride according to the general method. (0.44 g, 48% yield). LC-MS $t_R$=0.93 min, [M−H]$^-$=222; $^1$H NMR (250 MHz, DMSO-$d_6$) δ 9.75 (s, 1H), 9.40 (s, 1H), 7.35-7.23 (m, 3H), 4.47 (s, 2H).

Example 10

1-(2,5-Dichlorophenyl)-N-hydroxymethanesulfonamide (10)

Synthesis was carried out from (2,5-dichlorophenyl)methanesulfonyl chloride according to the general method. (0.34 g, 35% yield). LC-MS $t_R$=1.16 min, [M−H]$^-$=254/256; 1H NMR (250 MHz, DMSO-$d_6$) δ 9.80 (d, J=3.2 Hz, 1H), 9.47 (d, J=3.2 Hz, 1H), 7.66-7.40 (m, 3H), 4.60 (s, 2H).

Example 11

1-(2,4-Dichlorophenyl)-N-hydroxymethanesulfonamide (11)

Synthesis was carried out from (2,4-dichlorophenyl)methanesulfonyl chloride according to the general method. (0.48 g, 50% yield). LC-MS $t_R$=1.19 min, [M−H]$^-$=254; $^1$H NMR (250 MHz, DMSO-$d_6$) δ 9.74 (s, 1H), 9.33 (s, 1H), 7.62 (t, J=1.9 Hz, 1H), 7.43 (d, J=1.9 Hz, 2H), 4.51 (s, 2H).

Example 12

1-(3,4-Dichlorophenyl)-N-hydroxymethanesulfonamide (12)

Synthesis was carried out from (3,4-dichlorophenyl)methanesulfonyl chloride according to the general method. (0.61 g, 61% yield). LC-MS $t_R$=1.18 min, [M−H]$^-$=254; $^1$H NMR (250 MHz, DMSO-$d_6$) δ 9.72 (d, J=3.2 Hz, 1H), 9.28 (d, J=3.2 Hz, 1H), 7.72-7.59 (m, 2H), 7.37 (dd, J=8.3, 2.0 Hz, 1H), 4.49 (s, 2H).

Example 13

1-(3-Fluorophenyl)-N-hydroxymethanesulfonamide (13)

Synthesis was carried out from (3-fluorophenyl)methanesulfonyl chloride according to the general method. (0.71 g, 68% yield). LC-MS $t_R$=0.93 min, [M−H]$^-$=204; $^1$H NMR (500 MHz, DMSO-$d_6$) δ 9.76 (s, 1H), 9.27 (d, J=3.1 Hz, 1H), 7.42 (q, J=8.0, 7.2 Hz, 1H), 7.20 (dd, J=12.9, 8.6 Hz, 3H), 4.45 (s, 2H).

Example 14

1-(2-Fluorophenyl)-N-hydroxymethanesulfonamide (14)

Synthesis was carried out from (2-fluorophenyl)methanesulfonyl chloride according to the general method. (0.61 g, 59% yield). LC-MS $t_R$=0.91 min, [M−H]$^-$=204; $^1$H NMR (500 MHz, DMSO-$d_6$) δ 9.75 (d, J=3.1 Hz, 1H), 9.38 (d, J=3.1 Hz, 1H), 7.50-7.37 (m, 2H), 7.31-7.18 (m, 2H), 4.46 (s, 2H).

Example 15

1-(3-Bromophenyl)-N-hydroxymethanesulfonamide (15)

Synthesis was carried out from (3-bromophenyl)methanesulfonyl chloride according to the general method. (0.64 g, 66% yield). LC-MS $t_R$=1.09 min, [M−H]$^-$=264; $^1$H NMR (500 MHz, DMSO-$d_6$) δ 9.73 (s, 1H), 9.30 (s, 1H), 7.60-7.53 (m, 2H), 7.42-7.32 (m, 2H), 4.45 (s, 2H).

Example 16

1-(4-Bromophenyl)-N-hydroxymethanesulfonamide (16)

Synthesis was carried out from (4-bromophenyl)methanesulfonyl chloride according to the general method. (0.66 g, 69% yield). LC-MS $t_R$=1.11 min, [M+H]$^+$=267; $^1$H NMR (500 MHz, DMSO-$d_6$) δ 9.72 (s, 1H), 9.24 (s, 1H), 7.63-7.55 (m, 2H), 7.36-7.29 (m, 2H), 4.42 (s, 2H).

Example 17

N-Hydroxy-1-[3-(trifluoromethyl)phenyl]methanesulfonamide (17)

Synthesis was carried out from [3-(trifluoromethyl)phenyl]methanesulfonyl chloride according to the general method. (0.69 g, 70% yield). LC-MS $t_R$=1.14 min, [M−H]$^-$=254; $^1$H NMR (500 MHz, DMSO-$d_6$) δ 9.78 (s, 1H), 9.35 (s, 1H), 7.77-7.72 (m, 2H), 7.71-7.61 (m, 2H), 4.59 (s, 2H).

Example 18

N-Hydroxy-1-[4-(trifluoromethyl)phenyl]methanesulfonamide (18)

Synthesis was carried out from [4-(trifluoromethyl)phenyl]methanesulfonyl chloride according to the general method. (0.48 g, 46% yield). LC-MS $t_R$=1.18 min, [M−H]$^-$=254; $^1$H NMR (500 MHz, DMSO-$d_6$) δ 9.78 (s, 1H), 9.32 (s, 1H), 7.77 (d, J=8.2 Hz, 2H), 7.61 (d, J=8.1 Hz, 2H), 4.56 (s, 2H).

Example 19

1-(2-Chloro-6-fluorophenyl)-N-hydroxymethanesulfonamide (19)

Synthesis was carried out from (2-chloro-6-fluorophenyl)methanesulfonyl chloride according to the general method. (0.65 g, 67% yield). LC-MS $t_R$=1.59 min, [M−H]$^-$=238; $^1$H NMR (500 MHz, DMSO-$d_6$) δ 9.79 (d, J=3.3 Hz, 1H), 9.50 (d, J=3.3 Hz, 1H), 7.47 (td, J=8.2, 6.0 Hz, 1H), 7.41 (d, J=8.0 Hz, 1H), 7.34-7.26 (m, 1H), 4.63-4.59 (m, 2H).

Example 20

1-(3,5-Difluorophenyl)-N-hydroxymethanesulfonamide (20)

Synthesis was carried out from (3,5-difluorophenyl)methanesulfonyl chloride according to the general method. (0.42 g, 44% yield). LC-MS $t_R$=1.50 min, [M−H]⁻=222; ¹H NMR (500 MHz, DMSO-$d_6$) δ 9.75 (d, J=3.2 Hz, 1H), 9.30 (d, J=3.2 Hz, 1H), 7.26 (tt, J=9.5, 2.3 Hz, 1H), 7.15-7.05 (m, 2H), 4.51 (s, 2H).

Example 21

1-(2,6-Dichlorophenyl)-N-hydroxymethanesulfonamide (21)

Synthesis was carried out from (2,6-dichlorophenyl) methanesulfonyl chloride according to the general method. (0.78 g, 74% yield). LC-MS $t_R$=1.08 min, [M−H]⁻=255; ¹H NMR (250 MHz, DMSO-$d_6$) δ 9.78 (s, 1H), 9.46 (s, 1H), 7.58-7.50 (m, 2H), 7.41 (dd, J=9.0, 7.0 Hz, 1H), 4.79 (s, 2H).

Example 22

Preparation of 1-1,2-Benzoxazol-3-yl-N-hydroxymethanesulfonamide (22)

To a solution of aqueous hydroxylamine (0.71 ml of a 50% solution, 10.79 mmol) in tetrahydrofuran (6 mL) and water (1 mL) cooled to −5° C. was slowly added 1,2-benzoxazol-3-ylmethanesulfonyl chloride (1 g, 4.32 mmol) maintaining a reaction temperature of less than 10° C. The reaction was maintained at this temperature until complete consumption of the sulfonyl chloride was observed by LC-MS (about 5 min.), after which time the reaction was diluted with ethyl acetate (20 mL) and the organic portion was separated, washed with water (2×5 mL), dried over sodium sulfate, filtered and concentrated under reduced pressure to provide the N-hydroxysulfonamide as an orange solid. Trituration was carried out using heptanes:DCM to provide the title compound as a fawn-colored solid (0.05 g, 5% yield). LC-MS $t_R$=0.98 min, [M−H]⁻=227; ¹H NMR (500 MHz, DMSO-$d_6$) δ 9.88 (d, J=3.2 Hz, 1H), 9.55 (d, J=3.2 Hz, 1H), 7.95 (d, J=8.0 Hz, 1H), 7.79 (d, J=8.5 Hz, 1H), 7.72-7.67 (m, 1H), 7.45 (t, J=7.5 Hz, 1H), 4.99 (s, 2H).

Example 23

Preparation of N-hydroxy-1-(4-methanesulfonylphenyl)methanesulfonamide (31)

Sodium (4-methanesulfonylphenyl)methanesulfonate

To 1-(bromomethyl)-4-methanesulfonylbenzene (10 g, 40.14 mmol) in water (0.74 M) was added disodium sulfite (5.06 g, 40.14 mmol) and the reaction mixture was heated at reflux for 4.5 hours before being allowed to cool to room temperature. The resulting slurry was filtered and the resulting filtrate was concentrated in vacuo to yield the sulfonate as a white solid. The solid was washed with heptanes (100 mL), filtered and dried to give the title compound as a white solid (14.4 g, 91% yield). 1H NMR (500 MHz, Deuterium Oxide) δ 8.08-7.94 (m, 2H), 7.74 (d, J=8.4 Hz, 2H), 4.35 (s, 2H), 3.32 (s, 3H).

(4-Methanesulfonylphenyl)methanesulfonyl chloride

To a stirred suspension of sodium (4-methanesulfonylphenyl)methanesulfonate (12.5 g, 32.6 mmol) in DCE (40 mL) at 0° C. was added oxalyl chloride (4.65 ml, 48.89 mmol) and DMF (1.7 mL) over 10 minutes. The temperature was measured internally to ensure the rate of addition of DMF did not give rise to an increase in temperature above 5° C. The reaction was allowed to warm to room temperature and stirring continued for 20 hours, after this time, the resulting off-white precipitate was isolated by filtration and washed with DCM (50 mL) to afford the title compound as a white solid (7.85 g, 90% yield). 1H NMR (500 MHz, DMSO-d6) δ 7.84-7.76 (m, 2H), 7.55 (d, J=8.4 Hz, 2H), 3.84 (s, 2H), 3.18 (s, 3H).

N-Hydroxy-1-(4-methanesulfonylphenyl)methane-sulfonamide

Synthesis was carried out from (4-methanesulfonylphenyl)methanesulfonyl chloride according to the general method. (8.79 g, 44% yield), LC-MS $t_R$=0.56 min, [M+H]⁺=265.90; ¹H NMR (250 MHz, DMSO-$d_6$) δ 9.78 (d, J=2.6 Hz, 1H), 9.33 (d, J=2.7 Hz, 1H), 7.94 (d, J=8.3 Hz, 2H), 7.64 (d, J=8.3 Hz, 2H), 4.57 (s, 2H), 3.22 (s, 3H).

Example 24

1-(3,5-Dichlorophenyl)-N-hydroxymethanesulfonamide (35)

Synthesis was carried out from (3,5-dichlorophenyl) methanesulfonyl chloride according to the general method. (1.48 g, 50% yield), LC-MS $t_R$=1.16 min, [M−H]⁻=253.85/255.85, ¹H NMR (500 MHz, DMSO-$d_6$) δ 9.77 (d, J=3.3 Hz, 1H), 9.41 (d, J=3.3 Hz, 1H), 7.70 (d, J=1.9 Hz, 1H), 7.53-7.47 (m, 2H), 4.58 (s, 2H).

Example 25

N-Hydroxy-2-phenylethane-1-sulfonamide (36)

Synthesis was carried out from 2-phenylethane-1-sulfonyl chloride according to the general method. (0.54 g, 57% yield), LC-MS $t_R$=1.05 min, [M−H]⁻=199.85, ¹H NMR (250 MHz, DMSO-$d_6$) δ 9.61 (d, J=3.3 Hz, 1H), 9.27 (d, J=3.3 Hz, 1H), 7.37-7.18 (m, 5H), 3.43-3.34 (m, 2H), 3.05-2.94 (m, 2H).

Example 26

N-Hydroxy-1-(4-methylphenyl)methanesulfonamide (37)

Synthesis was carried out from (4-methylphenyl)methanesulfonyl chloride according to the general method. (0.52 g, 52% yield), LC-MS $t_R$=1.00 min, [M−H]⁻=199.85, ¹H NMR (250 MHz, DMSO-$d_6$) δ 9.65 (d, J=3.3 Hz, 1H), 9.16 (d, J=3.3 Hz, 1H), 7.22 (q, J=8.1 Hz, 4H), 4.34 (s, 2H), 2.30 (s, 3H).

Example 27

1-(3-Cyanophenyl)-N-hydroxymethanesulfonamide (38)

Synthesis was carried out from (3-cyanophenyl)methanesulfonyl chloride according to the general method. (0.53 g, 54% yield), LC-MS $t_R$=0.82 min, [M−H]⁻=210.85, ¹H NMR (250 MHz, DMSO-$d_6$) δ 9.65 (d, J=3.3 Hz, 1H), 9.16 (d, J=3.3 Hz, 1H), 7.22 (q, J=8.1 Hz, 4H), 4.34 (s, 2H), 2.30 (s, 3H).

Example 28

1-(4-tert-Butylphenyl)-N-hydroxymethanesulfonamide (39)

Synthesis was carried out from (4-tert-butylphenyl)methanesulfonyl chloride according to the general method. (0.59 g, 60% yield), LC-MS $t_R$=1.24 min, [M−H]$^-$=241.90, $^1$H NMR (250 MHz, DMSO-d$_6$) δ 9.66 (s, 1H), 9.19 (s, 1H), 7.40 (d, J=8.4 Hz, 2H), 7.29 (d, J=8.4 Hz, 2H), 4.35 (s, 2H), 1.28 (s, 9H).

Example 29

Nitroxyl Production as Determined Via N$_2$O Quantification

Nitrous oxide (N$_2$O) is produced via the dimerization and dehydration of HNO, and is the most common marker for nitroxyl production (Fukuto et al., *Chem. Res. Toxicol.* 18:790-801 (2005)). Nitroxyl, however, can also be partially quenched by oxygen to provide a product that does not produce N$_2$O (see Mincione et al., *J. Enzyme Inhibition* 13:267-284 (1998); and Scozzafava et al., *J. Med. Chem.* 43:3677-3687 (2000)). Using either nitrous oxide gas or Angeli's salt (AS) as a standard, the relative amounts of N$_2$O released from N-hydroxymethanesulfonamide nitroxyl donating compounds was examined via gas chromatography (GC) headspace analysis.

A procedure for determining the relative amounts of N$_2$O released from N-hydroxymethanesulfonamide nitroxyl donating compounds is as follows. GC was performed on an Agilent gas chromatograph equipped with a split injector (10:1 splitting), microelectron capture detector, and a HP-MOLSIV 30 m×0.32 mm×25 μm molecular sieve capillary column. Helium was used as the carrier (4 mL/min) gas and nitrogen was used as the make-up (20 mL/min) gas. The injector oven and the detector oven were kept at 200° C. and 325° C., respectively. All nitrous oxide analyses were performed with the column oven held at a constant temperature of 200° C.

All gas injections were made using an automated headspace analyzer. Vial pressurization was 15 psi. The analyzer's sample oven, sampling valve, and transfer line were kept at 40° C., 45° C., and 50° C., respectively. The oven stabilization, vial pressurization, loop fill, loop equilibration, and sample injection times were 1.00 min., 0.20 min., 0.20 min., 0.05 min., and 1.00 min., respectively.

All determinations used a batch of nominal 20 mL headspace vials with volumes pre-measured for sample uniformity (actual vial volume varied by ≤2.0% relative standard deviation (n=6)). The average vial volume for the batch was determined from six randomly-selected vials by calculating the weight difference between the capped and sealed empty (i.e., air-filled) vial and the capped and sealed deionized water-filled vial using the known density of deionized water, then averaging. Blanks were prepared by sealing and capping two vials then purging each for 20 seconds with a gentle argon stream. Nitroxyl standards were prepared by sealing and capping four vials then purging each for 1 minute with a gentle stream, from a gas cylinder, of a 3000 ppm nitroxyl standard.

CXL-1020 (N-hydroxy-2-methanesulfonylbenzene-1-sulfonamide) "standards" were prepared by, in duplicate, accurately weighing 10±0.5 mg of CXL-1020 and adding it to each 4 mL vial. Using an auto pipette, 1 mL of argon-purged anhydrous DMF (Sigma-Aldrich) was added to each 4 mL vial to form a CXL-1020 stock solution for each sample and the vials were capped and shaken and/or sonicated to insure complete dissolution upon visual observation. Using an auto pipette, 20 mL vials were charged with 5 mL of PBS (purged for at least 30 min. with argon prior to use), purged with argon for at least 20 sec., and sealed with a rubber septum. Using a 50 μL syringe, 50 μL of the CXL-1020 stock solution was injected into each 20 mL vial containing the PBS.

Samples were prepared as follows. In duplicate, 18±1 mg of each sample was accurately weighed into each 4 mL vial. Using an auto pipette, 1 mL of argon-purged anhydrous DMF was added to each 4 mL vial to form a sample stock solution for each sample and the vials were capped and shaken and/or sonicated to insure complete sample dissolution upon visual observation. Using an auto pipette, 20 mL vials were charged with 5 mL of PBS (purged for at least 30 min. with argon prior to use), purged with argon for at least 20 sec., and sealed with a rubber septum. The vials were equilibrated for at least 10 min. at 37° C. in a dry block heater. Thereafter, using a 50 μL syringe, 50 μL of a sample stock solution was injected into each 20 mL vial containing the PBS. The vials were then held at 37° C. in the dry block heater for a time period such that the sum of the time spent in the dry block heater plus the time spent in the automated headspace analyzer oven before sample injection equaled the desired incubation time.

The sequence for auto-injection was as follows: blank replicate 1, blank replicate 2, N$_2$O standard replicate 1, N$_2$O standard replicate 2, CXL-1020 standard replicate 1, CXL-1020 standard replicate 2, sample 1 replicate 1, sample 1 replicate 2, sample 2 replicate 1, sample 2 replicate 2, etc., concluding with N$_2$O standard replicate 3, and N$_2$O standard replicate 4. An EXCEL spreadsheet is used for inputting data thus determined and calculating, for each sample, the relative N$_2$O yield in percent for each incubation time. The results obtained are provided in Table 2.

TABLE 2

Results of N$_2$O Headspace Analysis

| Compound No. | Name | Relative N$_2$O Yield (90 minute incubation) |
|---|---|---|
| 1 | N-Hydroxy-1-(2-nitrophenyl) methanesulfonamide | 37 |
| 2 | 1-(4-Chlorophenyl)-N-hydroxymethanesulfonamide | 24 |

Another procedure for determining the relative amounts of N$_2$O released from N-hydroxymethanesulfonamide nitroxyl donating compounds is as follows. GC is performed on a Varian CP-3800 instrument equipped with a 1041 manual injector, electron capture detector, and a 25 m 5 Å molecular sieve capillary column. Grade 5.0 nitrogen is used as both the carrier (8 mL/min) and the make-up (22 mL/min) gas. The injector oven and the detector oven are kept at 200° C. and 300° C., respectively. All nitrous oxide analyses are performed with the column oven held at a constant temperature of 150° C. All gas injections are made using a 100 μL gas-tight syringe with a sample-lock. Samples are prepared in 15 mL amber headspace vials with volumes pre-measured for sample uniformity (actual vial volume ranges from 15.19 to 15.20 mL). Vials are charged with 5 mL of PBS containing diethylenetriamine pentaacetic anhydride (DTPA), purged with argon, and sealed with a rubber septum. The vials are equilibrated for at least 10 minutes at 37° C. in a dry block heater. A 10 mM stock solution of AS is prepared in 10 mM sodium hydroxide, and solutions of the nitroxyl donors are prepared in either acetonitrile or methanol and used immediately after preparation. From these stock solutions, 50 μL is introduced into individual thermally-equilibrated headspace vials using a 100 µL gas-tight syringe with a sample-lock to provide final substrate concentrations of 0.1 mM. Substrates are then incubated for 90 minutes or 360 minutes. The headspace (60 µL) is then sampled and injected five successive times into the GC apparatus using the gas-tight syringe with a sample lock. This procedure is repeated for two or more vials per donor.

Example 30

In Vitro Stability of N-Hydroxymethanesulfonamide Nitroxyl Donors in Plasma

Certain compounds from Table 1 were tested for their stability in plasma. The assay system comprised (i) PBS, or plasma from rat, dog or human (at least 3 donors, male, pooled) at pH 7.4, and (ii) for tests conducted in plasma, an anticoagulant (sodium heparin or sodium citrate). Each test compound (5 µM) was incubated in PBS or plasma at 37° C. on a THERMOMIXER® with shaking Three samples (n=3) were taken at each of seven sampling time points: 0, 10, 30, 60, 90, 180 and 360 minutes. The samples were immediately combined with 3 volumes (i.e., 3 times the volume of PBS or plasma) of acetonitrile containing 1% formic acid and an internal standard to terminate the reaction. AB SCIEX API 3000 LC-MS/MS analysis of the test compounds was performed without a standard curve. Half-lives ($T_{1/2}$) of the test compounds were determined from graphs of the percent remaining values using the peak area response ratio. The half-lives determined are provided in Table 3.

TABLE 3

Half-lives ($T_{1/2}$)

| Compound No. | Compound | $T_{1/2}$ (minutes) Rat | $T_{1/2}$ (minutes) Dog | $T_{1/2}$ (minutes) Human |
|---|---|---|---|---|
| 1 | N-Hydroxy-1-(2-nitrophenyl)methanesulfonamide | N/A | 26 | N/A |
| 2 | 1-(4-Chlorophenyl)-N-hydroxymethanesulfonamide | 114 | 62 | 102 |
| 3 | 1-(3-Chlorophenyl)-N-hydroxymethanesulfonamide | 40 | 70 | 52 |
| 4 | 1-(2-Chlorophenyl)-N-hydroxymethanesulfonamide | 38 | 36 | 28 |
| 5 | N-Hydroxy-1-(3-methylphenyl)methanesulfonamide | 61 | 55 | 81 |
| 6 | 1-(4-Fluorophenyl)-N-hydroxymethanesulfonamide | N/A | 34 | N/A |
| 7 | N-Hydroxy-1-[2-(trifluoromethyl)phenyl]methanesulfonamide | N/A | 25 | N/A |
| 8 | 1-(2,4-Difluorophenyl)-N-hydroxymethanesulfonamide | 36 | 46 | 31 |
| 9 | 1-(2,5-Difluorophenyl)-N-hydroxymethanesulfonamide | N/A | 30 | N/A |
| 10 | 1-(2,5-Dichlorophenyl)-N-hydroxymethanesulfonamide | 12 | 27 | 12 |
| 11 | 1-(2,4-Dichlorophenyl)-N-hydroxymethanesulfonamide | N/A | 45 | N/A |
| 12 | 1-(3,4-Dichlorophenyl)-N-hydroxymethanesulfonamide | 54 | 60 | 34 |
| 13 | 1-(3-Fluorophenyl)-N-hydroxymethanesulfonamide | N/A | 42 | N/A |
| 14 | 1-(2-Fluorophenyl)-N-hydroxymethanesulfonamide | N/A | 31 | N/A |
| 15 | 1-(3-Bromophenyl)-N-hydroxymethanesulfonamide | N/A | 45 | N/A |
| 16 | 1-(4-Bromophenyl)-N-hydroxymethanesulfonamide | N/A | 42 | N/A |
| 17 | N-Hydroxy-1-[3-(trifluoromethyl)phenyl]methanesulfonamide | N/A | 29 | N/A |
| 18 | N-Hydroxy-1-[4-(trifluoromethyl)phenyl]methanesulfonamide | 42 | 74 | 33 |
| 20 | 1-(3,5-Difluorophenyl)-N-hydroxymethanesulfonamide | N/A | 33 | N/A |
| 22 | 1-1,2-Benzoxazol-3-yl-N-hydroxymethanesulfonamide | 18 | 21 | 25 |
| 23 | N-Hydroxy-1-(4-methanesulfonylphenyl)methanesulfonamide | 63 | 46 | 82 |
| 25 | 1-(3,5-Dichlorophenyl)-N-hydroxymethanesulfonamide | 38 | 27 | 16 |
| 28 | 1-(3-Cyanophenyl)-N-hydroxymethanesulfonamide | 48 | 26 | 37 |
| 29 | 1-(4-tert-Butylphenyl)-N-hydroxymethanesulfonamide | 139 | 93 | 109 |

Example 31

Solubility of N-Hydroxymethanesulfonamide Nitroxyl Donors

The solubilities of the N-hydroxymethanesulfonamide nitroxyl donating compounds are measured by visual assessment at 100 μg/mL and 1000 μg/mL in a pH 4 buffer. The buffer is prepared by mixing 660 mL of Solution A (10.5023 g of citric acid dissolved in 1 L of water) and 450 mL of Solution B (14.7010 g of sodium citrate tribasic dihydrate dissolved in 1 L of water). The pH of the buffer is about 4 as measured by pH meter.

Each compound is shaken for about 5 minutes in the pH 4 buffer solution prepared above at two concentration points (100 μg/mL and 1000 μg/mL) and the solubility is observed visually.

Additionally, a sample of a compound of the disclosure are prepared in water to determine the approximate solubility of the compound in the absence of excipients (e.g., CAPTISOL®).

Example 32

Melting Points of N-Hydroxymethanesulfonamide Nitroxyl Donors

The melting points of certain compounds from Table 1 were determined on a METTLER TOLEDO 50 instrument with a start temperature of 80° C. at a rate of 5° C./min. to an end temperature of 300° C. The results that were obtained are provided in Table 4.

TABLE 4

Melting Points of Nitroxyl Donors

| Compound No. | Name | Melting Point (° C.) |
|---|---|---|
| 1 | N-hydroxy-1-(2-nitrophenyl)methanesulfonamide | 163 |
| 2 | 1-(4-Chlorophenyl)-N-hydroxymethanesulfonamide | 144 |
| 3 | 1-(3-Chlorophenyl)-N-hydroxymethanesulfonamide | 150 |
| 4 | 1-(2-chlorophenyl)-N-hydroxymethanesulfonamide | 124 |
| 5 | N-Hydroxy-1-(3-methylphenyl)methanesulfonamide | 98 |
| 6 | 1-(4-Fluorophenyl)-N-hydroxymethanesulfonamide | 158 |
| 7 | N-Hydroxy-1-[2-(trifluoromethyl)phenyl]methanesulfonamide | 123 |
| 8 | 1-(2,4-Difluorophenyl)-N-hydroxymethanesulfonamide | 166 |
| 9 | 1-(2,5-Difluorophenyl)-N-hydroxymethanesulfonamide | 125 |
| 10 | 1-(2,5-Dichlorophenyl)-N-hydroxymethanesulfonamide | 158 |
| 11 | 1-(2,4-Dichlorophenyl)-N-hydroxymethanesulfonamide | 158 |
| 12 | 1-(3,4-Dichlorophenyl)-N-hydroxymethanesulfonamide | 175 |
| 13 | 1-(3-Fluorophenyl)-N-hydroxymethanesulfonamide | 109 |
| 14 | 1-(2-Fluorophenyl)-N-hydroxymethanesulfonamide | 118 |
| 15 | 1-(3-Bromophenyl)-N-hydroxymethanesulfonamide | 161 |
| 16 | 1-(4-Bromophenyl)-N-hydroxymethanesulfonamide | 160 |
| 17 | N-Hydroxy-1-[3-(trifluoromethyl)phenyl]methanesulfonamide | 132 |
| 18 | N-Hydroxy-1-[4-(trifluoromethyl)phenyl]methanesulfonamide | 156 |
| 19 | 1-(2-Chloro-6-fluorophenyl)-N-hydroxymethanesulfonamide | 127 |
| 20 | 1-(3,5-Difluorophenyl)-N-hydroxymethanesulfonamide | 136 |
| 21 | 1-(2,6-Dichlorophenyl)-N-hydroxymethanesulfonamide | 140 |
| 22 | 1-1,2-Benzoxazol-3-yl-N-hydroxymethanesulfonamide | 143 |
| 23 | N-Hydroxy-1-(4-methanesulfonylphenyl)methanesulfonamide | 170 |
| 25 | 1-(3,5-Dichlorophenyl)-N-hydroxymethanesulfonamide | 167 |
| 26 | N-Hydroxy-2-phenylethane-1-sulfonamide | 117 |
| 27 | N-Hydroxy-1-(4-methylphenyl)methanesulfonamide | 129 |
| 28 | 1-(3-Cyanophenyl)-N-hydroxymethanesulfonamide | 156 |
| 29 | 1-(4-tert-Butylphenyl)-N-hydroxymethanesulfonamide | 138 |

Example 33

Solid-State Stability of N-Hydroxymethanesulfonamide Nitroxyl Donors

Solid, powdered samples of compound 2 (1-(4-chlorophenyl)-N-hydroxymethanesulfonamide) were sealed in double polyethylene bags and stored at 40° C., 70% relative humidity (RH) for up to 3 months. After 2 weeks, 1 month, 2 months, and 3 months of storage, the samples were analyzed for visual appearance and/or purity, as determined by high performance liquid chromatography (HPLC). The HPLC measurement conditions were as follows:

Column: PrimeSep AB, 150×4.6 mm, 5 μm
Injection Volume: 10 μL
Detection Wavelength: 220 nm
Mobile Phase A: 0.3% Trifluoroacetic acid (TFA) in deionized water (DI-H$_2$O)
Mobile Phase B: 0.2% TFA in acetonitrile
Diluent: Acetonitrile
Gradient:

| Time (min) | % A | % B |
|---|---|---|
| 0 | 95 | 5 |
| 5 | 95 | 5 |
| 20 | 50 | 50 |
| 25 | 50 | 50 |
| 25.1 | 95 | 5 |
| 30 | 95 | 5 |

Flow Rate: 1.0 mL/min
Column Temperature: 30° C.

The results that were obtained are provided in Table 5.

TABLE 5

Solid-State Stability of N-Hydroxymethanesulfonamide Nitroxyl Donors

| Test | 0 Weeks | 2 Weeks | 1 Month | 2 Months | 3 Months |
|---|---|---|---|---|---|
| Appearance | White solid | White solid | White solid | Off white light yellow solid | Off white light yellow solid |
| HPLC | Purity: 98.912% RRT[1] 0.88 0.368% RRT 1.23 0.087% RRT 1.35 0.633% | N/A | Purity: 95.579% RRT 0.88 0.966% RRT 1.54 1.959% RRT 1.76 0.502% | Purity: 82.665% RRT 0.88 3.600% RRT 1.53 6.432% RRT 1.77 3.234% | Purity: 76.661% RRT 0.88 4.108% RRT 1.50 10.123% RRT 1.77 3.165% |

[1]RRT = relative retention time

It will be apparent to those in the art that specific embodiments of the disclosed subject matter may be directed to one or more of the above- and below-indicated embodiments in any combination.

While the invention has been disclosed in some detail by way of illustration and example for purposes of clarity of understanding, it is apparent to those in the art that various changes may be made and equivalents may be substituted without departing from the true spirit and scope of the invention. Therefore, the description and examples should not be construed as limiting the scope of the invention.

All references, publications, patents, and patent applications disclosed herein are hereby incorporated by reference in their entirety.

What is claimed is:

1. A compound of formula (I):

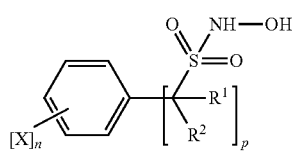

or a pharmaceutically acceptable salt thereof, wherein:
each X is independently selected from the group consisting of halo, —OH, —NO$_2$, —C≡N, (C$_1$-C$_6$)alkyl, (C$_1$-C$_6$)perhaloalkyl, (C$_1$-C$_6$)alkoxy, (C$_1$-C$_6$)perhaloalkoxy, (C$_6$-C$_{14}$)aryl, (C$_6$-C$_{14}$)aryloxy, (C$_4$-C$_7$)heterocycloalkyl, (5- or 6-membered)heteroaryl, —SH, —SR', —S(O)R', —S(O)OH, —S(O)OR', —SO$_2$NHOH, —SO$_2$NH$_2$, —NH$_2$, —NHR', —NR'R'' cycloalkoxy, —C(O)OH, —C(O)OR', —C(O)NH$_2$, C(O)NHR', and —C(O)NR'R''; wherein said aryl, heterocycloalkyl and heteroaryl are unsubstituted or substituted with 1, 2, 3,4 or 5 substituents selected from R$^4$;
each R$^4$ is independently selected from the group consisting of halo, —OH, —C≡N, —NO$_2$, —SH, =O, =S, =N—(C$_1$-C$_4$)alkyl, (C$_1$-C$_6$)alkyl, (C$_2$-C$_6$)alkenyl, (C$_2$-C$_6$)alkynyl, (C$_1$-C$_6$)alkoxy, (C$_2$-C$_6$)alkenyloxy, (C$_2$-C$_6$)alkynyloxy, (C$_6$-C$_{14}$)aryl, (C$_3$-C$_6$)cycloalkyl, (5- or 6-membered)heteroaryl, (C$_4$-C$_7$)heterocycloalkyl, —C(O)H, —C(O)NH$_2$, —C(O)OH, —NH—C(O)—NH$_2$, —NH—C(S), —NH$_2$, —SC≡N, —SO$_2$NH$_2$, —COR', —C(O)OR', C(O)NHR', —C(O)NR'R'', —NH$_2$, —NHR', —NR'R'', —SR', —S(O)R', —S(O)OR', and —OR';
wherein R' and R'' are independently selected from (C$_1$-C$_6$)alkyl, (C$_2$-C$_6$)alkynyl, (C$_6$-C$_{14}$)aryl, (C$_3$-C$_6$)cycloalkyl, (5- or 6-membered)heteroaryl and (C$_4$-C$_7$)heterocycloalkyl;
n is 0, 1 or 2;
p is 1; and
R$^1$ and R$^2$ are independently selected from H, halo and (C$_1$-C$_6$)alkyl optionally substituted with one or more independently selected halo(s), or R$^1$ and R$^2$ together with the carbon to which each is attached form (C$_3$-C$_6$)cycloalkyl or (C$_4$-C$_7$)heterocycloalkyl;
provided that:
(a) if n is 0, then R$^1$ and R$^2$ are not H;
(b) if n is 1 and X is COOH, then R$^1$ and R$^2$ are not H; and
(c) if n is 2 and each X is methyl, then R$^1$ and R$^2$ are not H.

2. The compound of claim 1, wherein
each X is independently selected from the group consisting of halo, —OH, —NO$_2$, —C≡N, (C$_1$-C$_6$)perhaloalkyl, (C$_1$-C$_6$)alkoxy, (C$_1$-C$_6$)perhaloalkoxy, (C$_6$-C$_{14}$)aryl, (C$_6$-C$_{14}$)aryloxy, (C$_4$-C$_7$)heterocycloalkyl, (5- or 6-membered)heteroaryl, (C$_6$-C$_{14}$)aryloxy, —SH, —SR', —S(O)R', —S(O)OH, —S(O)OR', —SO$_2$NHOH, —SO$_2$NH$_2$, —NH$_2$, —NHR', —NR'R'', cycloalkoxy, —C(O)OR', —C(O)NH$_2$, C(O)NHR', —C(O)NR'R''; wherein said aryl, heterocycloalkyl and heteroaryl are unsubstituted or substituted with 1, 2, 3, 4 or 5 substituents selected from R$^4$.

3. The compound of claim 1, wherein
each X is independently selected from (C$_1$-C$_6$)alkyl, halo, —NO$_2$, —C≡N, and S(O)OR, wherein said alkyl is optionally substituted with one or more independently selected halo(s) and R is H or (C$_1$-C$_6$)alkyl.

4. The compound of claim 1, wherein
each X is independently selected from (C$_1$-C$_6$)alkyl, halo, —NO$_2$, and S(O)OR, wherein said alkyl is optionally substituted with one or more independently selected halo(s);
n is 1 or 2;
R is H or (C$_1$-C$_6$)alkyl;
R$^1$ and R$^2$ are independently selected from H and (C$_1$-C$_6$)alkyl optionally substituted with one or more independently selected halo(s), or R$^1$ and R$^2$ together with the carbon to which each is attached form (C$_3$-C$_6$)cycloalkyl.

5. The compound of claim 1, wherein n is 0.
6. The compound of claim 1, wherein n is 1.
7. The compound of claim 1, wherein n is 2.
8. The compound of claim 1, wherein at least one X is (C$_1$-C$_6$)alkyl.
9. The compound of claim 6, wherein X is (C$_1$-C$_6$)alkyl.
10. The compound of claim 7, wherein each X is (C$_1$-C$_6$)alkyl.
11. The compound of claim 1, wherein at least one X is (C$_1$-C$_6$)alkyl substituted with one or more independently selected halo(s).
12. The compound of claim 11, wherein at least one X is methyl substituted with one or more independently selected halo(s).
13. The compound of claim 6, wherein X is (C$_1$-C$_6$)perhaloalkyl.
14. The compound of claim 6, wherein X is perhalomethyl.
15. The compound of claim 6, wherein X is perfluoromethyl.
16. The compound of claim 7, wherein each X is independently (C$_1$-C$_6$)perhaloalkyl.
17. The compound of claim 7, wherein each X is independently perhalomethyl.
18. The compound of claim 7, wherein each X is perfluoromethyl.
19. The compound of claim 1, wherein at least one X is halo.
20. The compound of claim 6, wherein X is halo.
21. The compound of claim 20, wherein X is bromo, chloro or fluoro.
22. The compound of claim 20, wherein X is bromo.
23. The compound of claim 20, wherein X is chloro.
24. The compound of claim 20, wherein X is fluoro.
25. The compound of claim 7, wherein each X is independently halo.
26. The compound of claim 25, wherein each X is independently selected from bromo, chloro and fluoro.
27. The compound of claim 25, wherein each X is bromo.
28. The compound of claim 25, wherein each X is chloro.
29. The compound of claim 25, wherein each X is fluoro.
30. The compound of claim 1, wherein at least one X is nitro.

31. The compound of claim 6, wherein X is nitro.
32. The compound of claim 7, wherein each X is nitro.
33. The compound of claim 1, wherein at least one X is cyano.
34. The compound of claim 6, wherein X is cyano.
35. The compound of claim 7, wherein each X is cyano.
36. The compound of claim 1, wherein at least one X is S(O)OR'.
37. The compound of claim 6, wherein X is S(O)OR'.
38. The compound of claim 6, wherein X is S(O)OH.
39. The compound of claim 37, wherein R' is $(C_1-C_6)$alkyl.
40. The compound of claim 37, wherein R' is methyl.
41. The compound of claim 7, wherein each X is independently S(O)OR'.
42. The compound of claim 7, wherein each X is independently S(O)OH.
43. The compound of claim 41, wherein R' is $(C_1-C_6)$alkyl.
44. The compound of claim 41, wherein R' is methyl.
45. The compound of claim 1, wherein at least one of $R^1$ and $R^2$ is H.
46. The compound of claim 1, wherein each of $R^1$ and $R^2$ is H.
47. The compound of claim 1, wherein $R^1$ is H and $R^2$ is $(C_1-C_6)$alkyl optionally substituted with one or more independently selected halo(s).
48. The compound of claim 1, wherein $R^1$ is H and $R^2$ is $(C_1-C_6)$alkyl.
49. The compound of claim 1, wherein $R^1$ is H and $R^2$ is methyl.
50. The compound of claim 1, wherein each of $R^1$ and $R^2$ is $(C_1-C_6)$alkyl optionally substituted with one or more independently selected halo(s).
51. The compound of claim 1, wherein each of $R^1$ and $R^2$ is $(C_1-C_6)$alkyl substituted with one or more independently selected halo(s).
52. The compound of claim 1, wherein each of $R^1$ and $R^2$ is methyl optionally substituted with one or more independently selected halo(s).
53. The compound of claim 1, wherein each of $R^1$ and $R^2$ is methyl substituted with halo.
54. The compound of claim 1, wherein each of $R^1$ and $R^2$ is methyl substituted with fluoro.
55. The compound of claim 1, wherein each of $R^1$ and $R^2$ is $(C_1-C_6)$alkyl.
56. The compound of claim 1, wherein each of $R^1$ and $R^2$ is methyl.
57. The compound of claim 1, wherein at least one of $R^1$ and $R^2$ is halo.
58. The compound of claim 1, wherein each of $R^1$ and $R^2$ is halo.
59. The compound of claim 1, wherein at least one of $R^1$ and $R^2$ is fluoro.
60. The compound of claim 1, wherein each of $R^1$ and $R^2$ is fluoro.
61. The compound of claim 1, wherein $R^1$ and $R^2$ together with the carbon to which each is attached form $(C_3-C_6)$cycloalkyl.
62. The compound of claim 1, wherein $R^1$ and $R^2$ together with the carbon to which each is attached form cyclopropyl.
63. The compound of claim 1, wherein $R^1$ and $R^2$ together with the carbon to which each is attached form $(C_4-C_7)$heterocycloalkyl.
64. The compound of claim 1, wherein $R^1$ and $R^2$ together with the carbon to which each is attached form oxetanyl.
65. The compound of claim 1, which is selected from:
N-hydroxy-1-(2-nitrophenyl)methanesulfonamide,
1-(4-chlorophenyl)-N-hydroxymethanesulfonamide,
1-(3-chlorophenyl)-N-hydroxymethanesulfonamide,
1-(2-chlorophenyl)-N-hydroxymethanesulfonamide,
N-hydroxy-1-(3-methylphenyl)methanesulfonamide,
1-(4-fluorophenyl)-N-hydroxymethanesulfonamide,
N-hydroxy-1-[2-(trifluoromethyl)phenyl]methanesulfonamide,
1-(2,4-difluorophenyl)-N-hydroxymethanesulfonamide,
1-(2,5-difluorophenyl)-N-hydroxymethanesulfonamide,
1-(2,5-dichlorophenyl)-N-hydroxymethanesulfonamide,
1-(2,4-dichlorophenyl)-N-hydroxymethanesulfonamide,
1-(3,4-dichlorophenyl)-N-hydroxymethanesulfonamide,
1-(3-fluorophenyl)-N-hydroxymethanesulfonamide,
1-(2-fluorophenyl)-N-hydroxymethanesulfonamide,
1-(3-bromophenyl)-N-hydroxymethanesulfonamide,
1-(4-bromophenyl)-N-hydroxymethanesulfonamide,
N-hydroxy-1-[3-(trifluoromethyl)phenyl]methanesulfonamide,
N-hydroxy-1-[4-(trifluoromethyl)phenyl]methanesulfonamide,
1-(2-chloro-6-fluorophenyl)-N-hydroxymethanesulfonamide,
1-(3,5-difluorophenyl)-N-hydroxymethanesulfonamide,
1-(2,6-dichlorophenyl)-N-hydroxymethanesulfonamide,
1-(4-chlorophenyl)-N-hydroxyethanesulfonamide,
2-(4-chlorophenyl)-N-hydroxypropane-2sulfonamide,
1-(4-chlorophenyl)-N-hydroxypropane-1sulfonamide,
1-(4-chlorophenyl)-1,1-difluoro-N-hydroxymethanesulfonamide,
N-hydroxy-1-(4-(methylsulfonyl)phenyl)methanesulfonamide,
1-(3,5-dichlorophenyl)-N-hydroxymethanesulfonamide,
N-hydroxy-1-(4-methylphenyl)methanesulfonamide,
1-(3-cyanophenyl)-N-hydroxymethanesulfonamide,
1-(4-tert-butylphenyl)-N-hydroxymethanesulfonamide,
N-hydroxy-2-phenylpropane-2-sulfonamide,
1,1-difluoro-N-hydroxy-1-phenylmethanesulfonamide,
N-hydroxy-1-phenylcyclopropane-1-sulfonamide,
N-hydroxy-3-phenyloxetane-3-sulfonamide,
and
pharmaceutically acceptable salts thereof.
66. The compound of claim 4, which is selected from:
N-hydroxy-1-(2-nitrophenyl)methanesulfonamide,
1-(4-chlorophenyl)-N-hydroxymethanesulfonamide,
1-(3-chlorophenyl)-N-hydroxymethanesulfonamide,
1-(2-chlorophenyl)-N-hydroxymethanesulfonamide,
N-hydroxy-1-(3-methylphenyl)methanesulfonamide,
1-(4-fluorophenyl)-N-hydroxymethanesulfonamide,
N-hydroxy-1-[2-(trifluoromethyl)phenyl]methanesulfonamide,
1-(2,4-difluorophenyl)-N-hydroxymethanesulfonamide,
1-(2,5-difluorophenyl)-N-hydroxymethanesulfonamide,
1-(2,5-dichlorophenyl)-N-hydroxymethanesulfonamide,
1-(2,4-dichlorophenyl)-N-hydroxymethanesulfonamide,
1-(3,4-dichlorophenyl)-N-hydroxymethanesulfonamide,
1-(3-fluorophenyl)-N-hydroxymethanesulfonamide,
1-(2-fluorophenyl)-N-hydroxymethanesulfonamide,
1-(3-bromophenyl)-N-hydroxymethanesulfonamide,
1-(4-bromophenyl)-N-hydroxymethanesulfonamide,
N-hydroxy-1-[3-(trifluoromethyl)phenyl]methanesulfonamide,
N-hydroxy-1-[4-(trifluoromethyl)phenyl]methanesulfonamide,
1-(2-chloro-6-fluorophenyl)-N-hydroxymethanesulfonamide, 1-(3,5-difluorophenyl)-N-hydroxymethanesulfonamide,
1-(2,6-dichlorophenyl)-N-hydroxymethanesulfonamide,
and pharmaceutically acceptable salts thereof.

67. A pharmaceutical composition comprising a compound of claim 1, and at least or pharmaceutically acceptable excipient.

68. The pharmaceutical composition of claim 67, wherein the pharmaceutical composition is suitable for intravenous administration.

69. The pharmaceutical composition of claim 67, wherein the pharmaceutical composition has a pH of about 5.5 to about 6.5.

70. The pharmaceutical composition of claim 67, wherein the pharmaceutical composition has a pH of from about 6 to about 6.5.

71. The pharmaceutical composition of claim 67, wherein the pharmaceutical composition has a pH of about 6.

72. A method of treating a cardiovascular disease, comprising administering an effective amount of a compound of claim 1 to a patient in need thereof.

73. The method of claim 72, wherein the cardiovascular disease is heart failure.

74. The method of claim 72, wherein the cardiovascular disease is acute decompensated heart failure.

75. The method of claim 72, wherein the compound is administered intravenously.

76. The method of claim 72, wherein the compound is administered at a dose of from about 20 μg nitroxyl donor/kg/minute to about 30 μg nitroxyl donor/kg/minute.

77. The method of claim 72, wherein the compound is administered orally.

* * * * *